(12) United States Patent
Misaghi et al.

(10) Patent No.: US 10,975,168 B2
(45) Date of Patent: Apr. 13, 2021

(54) METHODS OF MAKING FUCOSYLATED AND AFUCOSYLATED FORMS OF A PROTEIN

(71) Applicant: Genentech, Inc., South San Francisco, CA (US)

(72) Inventors: Shahram Misaghi, Clayton, CA (US); John B. Lowe, San Francisco, CA (US); Bradley Richard Snedecor, Portola Valley, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/968,214

(22) Filed: May 1, 2018

(65) Prior Publication Data

US 2018/0251572 A1    Sep. 6, 2018

Related U.S. Application Data

(63) Continuation of application No. PCT/US2016/059922, filed on Nov. 1, 2016.

(60) Provisional application No. 62/249,828, filed on Nov. 2, 2015, provisional application No. 62/338,280, filed on May 18, 2016.

(51) Int. Cl.
*C07K 16/44* (2006.01)
*C07K 14/435* (2006.01)
*G01N 33/68* (2006.01)

(52) U.S. Cl.
CPC ............ *C07K 16/44* (2013.01); *C07K 14/435* (2013.01); *G01N 33/6854* (2013.01); *C07K 2317/41* (2013.01); *C07K 2317/52* (2013.01); *C07K 2317/732* (2013.01); *C07K 2319/00* (2013.01)

(58) Field of Classification Search
CPC .. C07K 16/44; C07K 14/435; C07K 2317/41; C07K 2317/52; C07K 2317/732; C07K 2319/00; C07K 16/00; G01N 33/6854; C12N 9/0006; C12N 9/88; C12N 15/85; C12N 2510/02; C12P 21/005; C12Y 101/01271; C12Y 402/01047
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland |
| 4,927,762 A | 5/1990 | Darfler |
| 4,965,195 A | 10/1990 | Namen |
| 4,968,607 A | 11/1990 | Dower |
| 5,122,469 A | 6/1992 | Mather |
| 5,500,362 A | 3/1996 | Robinson |
| 5,821,337 A | 10/1998 | Carter |
| 6,037,525 A | 3/2000 | Thompson |
| 6,177,612 B1 | 1/2001 | Jordan |
| 6,239,328 B1 | 5/2001 | Thompson |
| 6,245,974 B1 | 6/2001 | Michalowski |
| 6,388,066 B1 | 5/2002 | Bruce |
| 7,129,062 B2 | 10/2006 | Mermod |
| 7,259,010 B2 | 8/2007 | Kim |
| 7,326,567 B2 | 2/2008 | Saha |
| 7,422,874 B2 | 9/2008 | Kim |
| 7,923,221 B1 | 4/2011 | Cabilly |
| 2003/0157108 A1* | 8/2003 | Presta ............... C07K 16/2896 424/145.1 |
| 2007/0020260 A1* | 1/2007 | Presta ............... C07K 16/2896 424/133.1 |
| 2008/0095762 A1* | 4/2008 | Presta ............... C07K 16/2896 424/130.1 |
| 2009/0208500 A1* | 8/2009 | Joly .................. C07K 16/00 424/134.1 |
| 2009/0285830 A1* | 11/2009 | Adams ............... C07K 16/242 424/158.1 |
| 2010/0304436 A1* | 12/2010 | Chen .................. C07K 16/00 435/69.6 |
| 2014/0005368 A1* | 1/2014 | Helman .............. C07K 16/00 530/388.22 |
| 2018/0171028 A1* | 6/2018 | Chatterjee ........... C12N 15/907 |

FOREIGN PATENT DOCUMENTS

| | | | |
|---|---|---|---|
| EP | 0367566 A1 | 5/1990 | |
| EP | 0367566 B1 | 5/1990 | |
| EP | 0460846 A1 | 12/1991 | |
| EP | 0460846 B1 | 12/1991 | |
| WO | WO8700195 A1 | 1/1987 | |
| WO | WO9003430 A1 | 4/1990 | |
| WO | WO-2012120500 A2 * | 9/2012 | ............ C07K 16/00 |
| WO | WO2013013013 A2 | 1/2013 | |
| WO | WO2013013013 A3 | 5/2014 | |
| WO | WO-2015026846 A1 * | 2/2015 | ........... C12N 5/0018 |
| WO | WO-2016075662 A2 * | 5/2016 | ...... C12Y 402/01047 |

OTHER PUBLICATIONS

Ripka J, Stanley P. Lectin-resistant CHO cells: selection of four new pea lectin-resistant phenotypes. Somat Cell Mol Genet. Jan. 1986;12(1):51-62.*
Ripka J, Adamany A, Stanley P. Two Chinese hamster ovary glycosylation mutants affected in the conversion of GDP-mannose to GDP-fucose. Arch Biochem Biophys. Sep. 1986;249(2):533-45.*
Imai-Nishiya H, Mori K, Inoue M, Wakitani M, et. al. Double knockdown of alpha 1,6-fucosyltransferase (FUT8) and GDP-mannose 4,6-dehydratase (GMD) in antibody-producing cells: a new strategy for generating fully non-fucosylated therapeutic antibodies with enhanced ADCC. BMC Biotechnol. Nov. 30, 2007;7:84.*
Ayukawa T, Matsumoto K, Ishikawa HO, Ishio A, Yamakawa T, Aoyama N, Suzuki T, Matsuno K. Rescue of Notch signaling in cells incapable of GDP-L-fucose synthesis by gap junction transfer of GDP-L-fucose in *Drosophila*. Proc Natl Acad Sci U S A. Sep. 18, 2012;109(38):15318-23. Epub Sep. 4, 2012.*

(Continued)

*Primary Examiner* — Rachel B Gill
(74) *Attorney, Agent, or Firm* — Morrison & Foerster LLP

(57) ABSTRACT

The present application relates to methods of producing a protein in fucosylated and afucosylated forms at a predetermined ratio.

21 Claims, 22 Drawing Sheets

Specification includes a Sequence Listing.

(56) References Cited

OTHER PUBLICATIONS

Taupin P. Cell lines expressing mutant FX proteins to generate proteins with reduced rate of fucosylation: WO2010/141478. Expert Opin Ther Pat. Jul. 2011;21(7):1143-6. doi: 10.1517/13543776.2011. 581228. Epub May 10, 2011.*
Adames, J.M. et al. (Dec. 12, 1985). "The c-myc Oncogene Driven by Immunoglobulin Enhancers Induces Lymphoid Malignancy in Transgenic Mice," Nature 318:533-538.
Aldrich, T.L. et al. (2003, e-pub, Jul. 19, 2003). "Ease Vectors for Rapid Stable Expression of Recombinant Antibodies," Biotechnol. Prog. 19(5):1433-1438.
Alexander, W.S. et al. (Apr. 1987). "Expression of the C-myc Oncogene Under Control of an Immunoglobulin Enhancer in Eµ-myc Transgenic Mice," Mol. Cell. Biol. 7(4):1436-1444.
Baenzinger, J.U. (1984). "The Oligosaccharides of Plasma Glycoproteins: Synthesis, Structure, and Function," Chapter 5 in The Plasma Proteins: Structure, Function and Genetic Control, Putnam, F. W. ed. 2nd Edition, vol. 4, Academic Press, New York, pp. 271-315.
Balaguer, E. et al. (Aug. 1, 2006, e-pub, Jun. 29, 2006). "Glycoprotein Characterization Combining Intact Protein and Glycan Analysis by Capillary Electrophoresis-Electrospray Ionization-Mass Spectrometry," Anal, Chem. 78 (15):5384-5393.
Barnes, D. et al. (Mar. 1, 1980). "Methods for Growth of Cultured Cells in Serum-Free Medium," Anal. Biochem. 102(2):255-270.
Becker, D.J. (2002). "Genetic and Biochemical Determinants of Fucosylated Glycan Express," Thesis from the University of Michigan, UMI No. 3121891, 144 pages.
Becker, D.J. et al. (Jul. 2003, e-pub. Mar. 19, 2003). "Fucose: Biosynthesis and Biological Function in Mammals," Glycobiology 13(7):41R-53R.
Becker, D.J. et al. (Oct. 8, 1999). "Leukocyte Adhesion Deficiency Type II," Biochim. Biphys. Acta 1455 (2-3):193-204.
Benoist, C. et al, (Mar. 26, 1981). "In Vivo Sequence Requirements of the SV40 Early Promotor Region," Nature 290:304-310.
Brinster, R.L. et al. (Mar. 4, 1982). "Regulation of Metallothionein—Thymidine Kinase Fusion Plasmids Injected Into Mouse Eggs," Nature 296:39-42.
Capel, P.J. et al. (Feb. 1994). "Heterogeneity of Human IgG Fc receptors," Immunomethods 4(1):25-34.
Carter, P.J. (May 15, 2011, e-pub. Mar. 1, 2011). "Introduction to Current and Future Protein Therapeutics: A Protein Engineering Perspective," Exp. Cell Res. 317:1261-1269.
Certified Priority Document, dated Mar. 21, 2016, for PCT Application No. PCT/IB2015/058777, filed on Nov. 15, 2014, 13 pages.
Cheng, Z.J. et al. (Dec. 2014, e-pub. Jul. 31, 2014). "Development of a Robust Reporter-Based ADCC Assay With Frozen, Thaw-and-Use Cells to Measure Fc Effector Function of Therapeutic Antibodies," J. Immunol. Methods 414:69-81.
Clynes, R. et al. (Jan. 1998). "Fc Receptors are Required in Passive and Active Immunity to Melanoma," Proc. Natl. Acad. Sci. U.S.A. 95:652-656.
Cong, L. et al. (Feb. 2013). "Multiplex genome engineering using CRISPR/Cas systems," Science 339:819-823.
Cosman, D. et al. (Dec. 20/27, 1984). "Cloning, Sequence and Expression of Human Interleukin-2 Receptor," Nature 312:768-771.
Czajkowsky, D.M. et al. (Oct. 2012)."Fc-Fusion Proteins: New Developments and Future Perspectives," EMBO Mol. Med. 4(10):1015-1028.
Davies, J. et al. (Aug. 2001). "Expression of GnTIII in a Recombinant Anti-CD20 CHO Production Cell Line: Expression of Antibodies With Altered Glycoforms Leads to an Increase in ADCC Through Higher Affinity for FC gamma RIII," Biotechnol. Bioeng. 74(4):288-294.
Daëron, M. (1997). "Fc receptor biology," Ann. Rev. Immunol. 15:203-234.
De Haas, M. et al. (Oct. 1995). "Fc Gamma receptors of Phagocytes," J. Lab. Clin. Med. 126:330-341.

Deboer, H.A. et al. (Jan. 1983). "The Tac Promoter: a Functional Hybrid Derived From the trp and lac Promoters," Proc. Natl. Acad. Sci. U.S.A. 80(1):21-25.
Doench, J.G. et al. (Dec. 2014). "Rational Design of Highly Active sgRNAs for CRISPR-Cas9-Mediated Gene Inactivation," Nat. Biotechnol. 32(12)1262-1267, 18 pages.
Flatman, S. et al. (2007, e-pub, Dec. 11, 2006). "Process analytics for Purification of Monoclonal Antibodies," J. Chromatogr. B. 848:79-87.
Gaj, T. et al. (Jul. 2013, e-pub. May 9, 2013). "ZFN, TALEN, and CRISPR/Cas-Based Methods for Genome Engineering," Trends Biotechnol. 31(7):397-405.
Gazzano-Santoro, H. et al. (Mar. 28, 1997). "A Non-Radioactive Complement-Dependent Cytotoxicity Assay for Anti-CD20 Monoclonal Antibody," J. Immunol, Methods 202:163-171.
Gluzman, Y. et al. (Jan. 1981). "SV40-Transformed Simian Cells Support the Replication of Early SV40 Mutants," Cell 23(1):175-182.
Grosschedl, R. et al. (Oct. 1984). "Introduction of a µ Immunoglobulin Gene Into the Mouse Germ Line: Specific Expression in Lymphoid Cells and Synthesis of Functional Antibody," Cell 38(3):647-658.
Guss, B. et al. (Jul. 1986). "Structure of the IgG-Binding Regions of Streptococcal Protein G," EMBO J. 5 (7):1567-1575.
Guyer, R.L. et al, (Aug. 1976), "Immunoglobulin Binding by Mouse Intestinal Epithelial Cell Receptors," J. Immunol. 117(2):587-593.
Ham, R.J, et al. (1979). "Media and Growth Requirements," Meth. Enz. 58:44-93.
Hammer, R.E. et al. (Jan. 2, 1987). "Diversity of Alpha-Fetoprotein Gene Expression in Mice is Generated by a Combination of Separate Enhancer Elements," Science 235:53-58.
Hanahan, D. (May 9, 1985). "Heritable Formation of Pancreatic β-Cell Tumours in Transgenic Mice Expressing Recombinant Insulin/Simian Virus 40 Oncogenes," Nature 315:115-122.
Hu, Z. et al. (Jul.-Aug. 2013, e-pub. Apr. 18, 2013). "Chinese Hamster Ovary K1 Host Cell Enables Stable Cell Line Development for Antibody Molecules Which Are Difficult to Express in DUXB11-Derived Dihydrofolate Reductase Deficient Host Cell," Biotechnol. Progr. 29(4):980-985.
Huse, K. et al. (May 2002), "Purification of Antibodies by Affinity Chromatography," J. Biochem, Bioph. Meth. 51 (3):217-231.
International Preliminary Report on Patentability dated May 8, 2018, for PCT Application No. PCT/US2016/059922, filed on Nov. 1, 2016, 9 pages.
International Search Report dated Jan. 30, 2017, for PCT Application No. PCT/US2016/059922, filed on Nov. 1, 2016, 7 pages.
Intra, J. et al. (May 1, 2007, e-pub, Nov. 11, 2006). "Comparative and Phylogenetic Analysis of α-L-Fucosidase Genes," Gene 392(1-2):34-46.
Jefferis, R. et al. (Jun. 1998). "IgG-Fc-Mediated Effector Functions: Molecular Definition of Interaction Sites for Effector Ligands and the Role of Glycosylation," Immunol. Rev. 163:59-76.
Jilani, S.M. et al. (May 2003). "Selective Binding of Lectins to Embryonic Chicken Vasculature," J. Histochem. Cystochem. 51(5):597-604.
Jones. "Analysis of Polypeptides and Proteins," Adv. Drug Delivery Rev. 10:29-90, (1993).
Kabat, E.V. et al. (1991). Sequences of Proteins Immunological Interest, 5th Ed. Public Health Service, National Institutes of Health Bethesda, MD, pp. iii-xix.
Kanda, Y. et al. (Jun. 19, 2007). "Establishment of a GDP-Mannose 4,6-Dehydratase (GMD) Knockout Host Cell Line: A New Strategy for Generating Completely Non-Fucosylated Recombinant Therapeutics," Journal of Biotechnology 130(3):300-310.
Kelsey, G.D. et al. (Apr. 1987). "Species-and Tissue-Specific Expression of Human alpha 1-Antitrypsin in Transgenic Mice," Genes and Devel. 1(2):161-171.
Kim, J-K. et al, (1994). "Localization of the Site of the Murine IgGI Molecule That is Involved in Binding to the Murine Intestinal Fc Receptor," Eur. J. Immunol. 24:2429-2434.
Kim, T.K. et al. (2010). "Mammalian Cell Transfection: The Present and the Future," Anal. Bioanal Chem. 397:3173-3178.

(56) References Cited

OTHER PUBLICATIONS

Kollias, G. et al. (Jul. 4, 1986). "Regulated Expression of Human A γ-, β-, and Hybrid γβ-Globin Genes in Transgenic Mice: Manipulation of the Developmental Expression Patterns," Cell 46(1):89-94.
Krumlauf, R. et al. (Jul. 1985). "Developmental Regulation of Alpha-Fetoprotein Genes in Transgenic Mice," Mol. Cell. Biol. 5(7):1639-1648.
Leder, A. et al. (May 23, 1986). "Consequences of Widespread Deregulation of the c-myc Gene in Transgenic Mice: Multiple Neoplasms and Normal Development," Cell 45:485-495.
Li, F. et al. (Sep./Oct. 2010). "Cell Culture Processes for Monoclonal Antibody Production," Mabs 2(5):466-477.
Lindmark, R. et al. (1983). "Binding of Immunoglobulins to Protein A and Immunoglobulin Levels in Mammalian Sera," J. Immunol. Meth. 62:1-13.
Louie, S. et al. (Sep. 26, 2016). "FX Knockout CHO Hosts Can Express Desired Ratios of Fucosylated or Afucosylated Antibodies With High Titers and Comparable Product Quality," Biotechnology and Bioengineering 9999:1-13.
MacDonald, R.J. (Jan.-Feb. 1987). "Expression of the Pancreatic Elastase I Gene in Transgenic Mice," Hepatology 7(1):42S-51S.
Magram, J. et al. (May 23, 1985). "Developmental Regulation of a Cloned Adult β-Globin Gene in Transgenic Mice," Nature 315(6017):338-340.
Mali, P. et al. (Oct. 2013). "Cas9 as a versatile tool for engineering biology," Nat. Methods 10(10):957-963, 16 pages.
Malphettes, L. et al. (Apr. 8, 2010). "Highly Efficient Deletion of FUT8 in CHO Cell Lines Using Zinc-Finger Nucleases Yields Cells That Produce Completely Nonfucosylated Antibodies," Biotechnology and Bioengineering 106(5):774-783.
Mason, A.J. et al. (Dec. 12, 1986). "The Hypogonadal Mouse: Reproductive Functions Restored by Gene Therapy," Science 234:1372-1378.
McMahan, C.J. et al. (Oct. 1991). "A Novel IL-1 Receptor, Cloned From B cells by Mammalian Expression, is Expressed in Many Cell Types," EMBO J. 10(10):2821-2832.
Miller, A.S. et al. (Nov. 30, 2012, e-pub. Aug. 14, 2012). "Development of an ELISA Based Bridging Assay as a Surrogate Measure of ADCC," J. Immunol. Methods 385(1-2):45-50.
Misaghi, S. et al. (Nov.-Dec. 2014, e-pub. Aug. 16, 2014). "It's Time to Regulate: Coping With Product-Induced Nongenetic Clonal Instability in CHO Cell Lines Via Regulated Protein Expression," Biotechnol. Progr. 30 (6):1432-1440.
Mulloy, B. et al. (2009). "Structural Analysis of Glycans," Chapter 47 in Essentials of Glycobiology, 2nd Ed., Cummings, V.A. ed., Cold Spring Harbor Laboratory Press, Cold Spring Harbor, New York, 22 pages.
Ohyama, C. et al. (Jun. 5, 1998). "Molecular Cloning and Expression of GDP-D-mannose-4,6-dehydratase, a Key Enzyme for Fucose Metabolism Defective in Lec13 Cells," J. Biol. Chem. 273(23):14582-14587.
Okeley, N.M. et al. (Apr. 2, 2013). "Development of Orally Active Inhibitors of Protein and Cellular Fucosylation," Proc. Natl. Acad. Sci. U.S.A. 110(14):5404-5409.
Ornitz, D.M. et al. (1985). "Elastase I Promoter Directs Expression of Human Growth Hormone and SV 40 T Antigen Genes to Pancreatic Acinar Cells in Transgenic Mice," Cold Spring Harbor Symp. Quant, Biol. 50:399-409.
O'Keefe, E.P. (Jun. 6, 2013, last updated Aug. 8, 2018). siRNAs and shRNAs: Tools for Protein Knockdown by Gene Silencing, Mater. Methods 3:1-12.
Peipp, M. et al. (Sep. 15, 2008, e-pub. Jun. 19, 2008). "Antibody Fucosylation Differentially impacts Cytotoxicity Mediated by NK and PMN Effector Cells," Blood 112(6):2390-2399.
Pinkert, C.A. et al. (1987). "An Albumin Enhancer Located 10 kb Upstream Functions Along With its Promoter to Direct Efficient, Liver-Specific Expression in Transgenic Mice," Genes and Devel. 1:268-276.
Protocol Online. (May 29, 2004). "Rules of siRNA Design for RNA Interference (RNAi)," located at www.protocol-online.org/prot/

Protocols/Rules-of-siRNA-design-for-RNA-interference-RNAi-3210.html, last visited on May 2, 2019, 2 pages.
Raju, T.S. et al. (May 2000). "Species-Specific Variation in Glycosylation of IgG: Evidence for the Species-Specific Sialylation and Branch-Specific Galactosylation and Importance for Engineering Recombinant Glycoprotein Therapeutics," Glycobiology 10(5):477-486.
Rasmussen, B. et al. (1998). "Isolation, Characterization and Recombinant Protein Expression in Veggie-CHO: A Serum-free CHO Host Cell Line," Cytotechnology 28(1-3):31-42.
Ravetch, J.V. et al. (1991). "Fc Receptors," Annu. Rev. Immuno. 9:457-492.
Ravetch, J.V. et al. (2001). "IgG Fc Receptors," Annu. Rev. Immunol. 19:275-290.
Readhead, C. et al. (Feb. 27, 1987). "Expression of A Myelin Basic Protein Gene in Transgenic Shiverer Mice: Correction of the Dysmyelinating Phenotype," Cell 48:703-713.
Reynolds, A. et al. (Mar. 2004, e-pub. Feb. 1, 2004). "Rational siRNA Design for RNA Interference," Nat, Biotechnol. 22(3):326-330.
Rudd, P.M. et al. (Mar. 23, 2001). "Glycosylation and the Immune System," Science 291:2370-2376.
Sambrook, J. et al. (1989). Molecular Cloning: A Laboratory Manual, 2nd ed., Cold Spring Harbor Laboratory, Cold Spring Harbor, NY, Table of Contents, v-xxxii, 29 pages.
Seth, A et al. (2010, e-pub. Nov. 10, 2010). Core Fucosylation Is Required for Midline Patterning During Zebrafish Development, Dev. Dynamics 239:3380-3390.
Shatz, W. et al. (Nov./Dec. 2013, e-pub. Aug. 29, 2013). Knobs-Into-Holes Antibody Production in Mammalian Cell Lines Reveals That Asymmetric Afucosylation is Sufficient for Full Antibody-Dependent Cellular Cytotoxicity, mAbs 5(6):872-881.
Shields, R.L. et al. (Jul. 26, 2002, e-pub. May 1, 2002). "Lack of Fucose on Human IgG1 N-Linked Oligosaccharide Improves Binding to Human FcγRIII and Antibody-dependent Cellular Toxicity," J. Biol. Chem. 277:26733-26740.
Silva, G.et al. (2011). "Meganucleases and Other Tools for Targeted Genome Engineering: Perspectives and Challenges for Gene Therapy," Curr. Gene Ther. 11(1):11-27
Smith, P.L. et al. (Aug. 19, 2002). "Conditional Control of Selectin Ligand Expression and Global Fucosylation Events in Mice With a Targeted Mutation at the FX Locus," J. Cell Biol. 158(4):801-815.
Swift, G.H. et al. (Oct. 1984), "Tissue-Specific Expression of the Rat Pancreatic Elastase I Gene in Transgenic Mice," Cell 38:639-646.
Szabo, Z. et al. (Mar. 15, 2010). "Rapid Release of N-Linked Glycans From Glycoproteins By Pressure Cycling Technology," Anal. Chem. 82:2588-2593.
Tada, M. et al. (Apr. 21, 2014). :"Development of a Cell-Based Assay Measuring the Activation of FcεRIIa for the Characterization of Therapeutic Monoclonal Antibodies," PloS One 9(4):e95787, 1-9.
Thomsen, D.L. et al. (Feb. 1984). "Promoter-Regulatory Region of the Major Immediate Early Gene of Human Cytomegalovirus," Proc. Natl. Acad. Sci. U.S.A. 81:659-663.
Umaña, P. et al. (Feb. 1999). "Engineered Glycoforms of an Antineuro-Blastoma IgG 1 With Optimized Antibody-Dependent Cellular Cytotoxic Activity," Nat. Biotechnol. 17:176-180.
Von Horsten, H.H. et al. (2010, e-published on Jul. 15, 2010). "Production of Non-Fucosylated Antibodies by Co-Expression of Heterologous GDP-6-Deoxy-D-Lyxo-4-Hexulose Reductase," Glycobiology 20(12):1607-1618.
Wagner, M.J. et al. (Mar. 1981). "Nucleotide sequence of the thymidine kinase gene of herpes simplex virus type 1," Proc. Natl. Acad. Sci. U.S.A. 78(3):1444-1445.
Written Opinion dated Jan. 30, 2017, for PCT Application No. PCT/US2016/059922, filed on Nov. 1, 2016, 8 pages.
Wurm, F.M. (Nov. 2014, e-published on Nov. 4, 2004). "Production of recombinant protein therapeutics in cultivated mammalian cells," Nat. Biotechnol. 22(11):1393-1398.
Xu, X. et al. (Aug. 2011, e-pub. Jul. 31, 2011). "The Genomic Sequence of the Chinese Hamster Ovary (CHO) K1 Cell Line," Nat. Biotechnol. 29(8):735-741.

(56) References Cited

OTHER PUBLICATIONS

Yamamoto, T. et al. (Dec. 1980). "Identification of a functional promoter in the long terminal repeat of Rous sarcoma virus," Cell 22:787-797.
Yamane-Ohnuki, N. et al. (Sep. 5, 2004, e-pub. Aug. 6, 2004). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnol. Bioeng, 87(5):614-622.
Certified Priority Document, dated Jun. 30, 2016, for PCT Application No. PCT/162016/052774, filed on May 13, 2016, 14 pages.

\* cited by examiner

FIG. 6C

| Glycan type | G-1 | G0 | G1 | G1' | G2 | Man5 | G0-1-F | G0-F | G1-F | G1'-F | G2-F |
|---|---|---|---|---|---|---|---|---|---|---|---|
| FXKO3-5 | n/a | n/a | n/a | n/a | n/a | 5.1 | 6.2 | 70.2 | 11.0 | 5.1 | 1.9 |
| FXKO3-7 | n/a | n/a | n/a | n/a | n/a | 4.7 | 5.0 | 68.2 | 13.3 | 6.1 | 2.3 |
| FXKO3-11 | n/a | n/a | n/a | n/a | n/a | 5.2 | 5.4 | 73.1 | 9.6 | 4.9 | 1.6 |
| CHO-K1 | 9.5 | 64.6 | 11.8 | 4.0 | 1.5 | 3.7 | n/a | 1.4 | n/a | n/a | n/a |
| FXKO3-5 +Fucose | 5.2 | 64.8 | 14.8 | 4.8 | 2.3 | 3.2 | n/a | 1.8 | n/a | n/a | n/a |
| FXKO3-7 +Fucose | 3.7 | 63.2 | 18.2 | 5.6 | 2.9 | 2.3 | n/a | 1.4 | n/a | n/a | n/a |
| FXKO3-11 +Fucose | 4.1 | 69.0 | 13.8 | 4.3 | 2.3 | 3.1 | n/a | 1.2 | n/a | n/a | n/a |

| Fucose concentration (mM) | G0-F | G1-F | G2-F | Man5 | G0 | G1 | G2 |
|---|---|---|---|---|---|---|---|
| 0 | 67.3 | 14.3 | 1 | 2.8 | 0 | 0 | 0 |
| 0.01 | 54.5 | 11.6 | 0.8 | 2.9 | 13.4 | 4 | 0.4 |
| 0.025 | 32 | 7.1 | 0.5 | 2.9 | 34.4 | 11 | 1.3 |
| 0.05 | 16.5 | 5.2 | 0.4 | 2.2 | 48.4 | 18.3 | 2.3 |
| 1 | 3 | 1.3 | 0 | 2.4 | 62.5 | 25.8 | 2.5 |

| Fucose (mM) | G0-F | G1-F | G2-F | Man5 | G0 | G1 | G2 |
|---|---|---|---|---|---|---|---|
| 0 | 73.6 | 9.5 | 0.9 | 2.9 | 0.2 | 0.5 | 0 |
| 0.01 | 54.9 | 7.6 | 0.8 | 3 | 17.8 | 3 | 0.5 |
| 0.02 | 29.4 | 4.7 | 0.4 | 2.3 | 46.7 | 7.4 | 1 |
| 0.03 | 9.6 | 2.1 | 0.2 | 3.3 | 67.5 | 10.5 | 1.4 |
| 0.05 | 3.2 | 0.9 | 0.1 | 3.2 | 74.4 | 12.5 | 1.6 |
| 1 | 2.1 | 0.7 | 0 | 2.1 | 76.5 | 14.4 | 1.9 |

| Fucose (mM) | % sum of afucosylated glycans | % relative ADCC Activity |
|---|---|---|
| 1:3 mix (0&1 mM) | 25.4 | 34 |
| 1:1 mix (0&1 mM) | 45.9 | 54 |
| 3:1 mix (0&1 mM) | 66.4 | 85 |

METHODS OF MAKING FUCOSYLATED AND AFUCOSYLATED FORMS OF A PROTEIN

CROSS REFERENCE TO RELATED APPLICATIONS

This application is a continuation of International Application No. PCT/US2016/059922 filed on Nov. 1, 2016, which claims priority to U.S. Provisional Patent Application No. 62/249,828, filed Nov. 2, 2015, and U.S. Provisional Patent Application No. 62/338,280, filed May 18, 2016, the disclosures of which are hereby incorporated herein by reference in their entirety.

SUBMISSION OF SEQUENCE LISTING ON ASCII TEXT FILE

The content of the following submission on ASCII text file is incorporated herein by reference in its entirety: a computer readable form (CFR) of the Sequence Listing (file name: 146392035300SEQLIST.TXT, dated recorded: Mar. 13, 2018, size: 2 KB).

TECHNICAL FIELD

The present application relates to methods of producing fucosylated and afucosylated forms of a protein at a predetermined ratio.

BACKGROUND

Glycoproteins are essential for proper function of all arms of the immune system including the innate and adaptive immune system. Glycoproteins are involved in recognition, binding, signaling, and elimination of threat via complement-dependent cytotoxicity (CDC) and antibody-dependent cell-mediated cytotoxicity (ADCC) (Rudd et al., *Science*, 291, 2001, 2370-2376; and Jefferis et al., *Immunol Rev*, 163, 1998, 59-76). Mammalian expressed antibodies bear a single glycan on $Asn^{297}$ residues of their heavy chain (HC). The presence and composition of the glycan structure influences the receptor binding and effector function of the antibody (Rudd et al., *Science*, 291, 2001, 2370-2376; and Jefferis et al., *Immunol Rev*, 163, 1998, 59-76). For example, variations in glycan composition of the Fc region of an IgG (Fcγ) differentially affect the binding affinity of the Fc region and Fc binding receptors (FcγR). There are three classes of FcγR, namely, FcγRI, FcγRII, and FcγRIII (Jefferis et al., *Immunol Rev*, 163, 1998, 59-76; Ravetch & Bolland, *Annu Rev Immunol*, 19, 2001, 275-290). Differential affinities of an antibody and Fcγ receptors dictate the fate of immune response of the host to a particular antigen and further may be responsible for activation, inhibition, antibody efficacy/half-life, tolerance, and autoimmune response (Ravetch & Bolland, *Annu Rev Immunol*, 19, 2001, 275-290). The affinity of an antibody for different types of receptors can change depending on the presence and composition of the glycans it bears, thus highlighting the importance of oligosaccharide/protein interactions on the biological function of antibodies (Raju et al., *Glycobiology*, 10, 2000, 477-486; Jefferis et al., *Immunol Rev*, 163, 1998, 59-76).

Advances in the therapeutic protein field allow for expression of recombinant proteins in serum free cultures (Wurm, *Nat Biotechnol*, 22, 2004, 1393-1398) and development of an increasing number of protein-based therapeutics, such as antibody-based therapeutics, for treating diseases (Carter, *Exp Cell Res*, 317, 2011, 1261-1269).

Following the expression of proteins in eukaryotic, e g mammalian host cells, the proteins undergo post-translational modifications, often including the enzymatic addition of sugar residues, generally referred to as "glycosylation."

Glycosylation of polypeptides is typically either N-linked or O-linked. N-linked refers to the attachment of the carbohydrate moiety to the side-chain of an asparagine residue. The tripeptide sequences, asparagine (Asn)-X-serine (Ser) and asparagine (Asn)-X-threonine (Thr), wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, fucose, N-acetylglucosamine, or xylose to a hydroxyamino acid, most commonly serine or threonine, although 5-hydroxyproline or 5-hydroxylysine may also be involved in O-linked glycosylation.

Glycosylation patterns for proteins produced by mammals are described in detail in The Plasma Proteins: Structure, Function and Genetic Control, Putnam, F. W., ed., 2nd edition, Vol. 4, Academic Press, New York, 1984, especially pp. 271-315. In this chapter, asparagine-linked oligosaccharides are discussed, including their subdivision into at least three groups referred to as complex, high mannose, and hybrid structures, as well as glycosidically linked oligosaccharides.

In the case of N-linked glycans, there is an amide bond connecting the anomeric carbon (C-1) of a reducing-terminal N-acetylglucosamine (GlcNAc) residue of the oligosaccharide and a nitrogen of an asparagine (Asn) residue of the polypeptide. In animal cells, O-linked glycans are attached via a glycosidic bond between N-acetylgalactosamine (GalNAc), galactose (Gal), fucose, N-acetylglucosamine, or xylose and one of several hydroxyamino acids, most commonly serine (Ser) or threonine (Thr), but also hydroxyproline or hydroxylsine in some cases.

The biosynthetic pathway of O-linked oligosaccharides consists of a step-by-step transfer of single sugar residues from nucleotide sugars by a series of specific glycosyltransferases. The nucleotide sugars which function as the monosaccharide donors are uridine-diphospho-GalNAc (UDP-GalNAc), UDP-GlcNAc, UDP-Gal, guanidine-diphospho-fucose (GDP-Fuc), and cytidine-monophospho-sialic acid (CMP-SA).

In N-linked oligosaccharide synthesis, initiation of N-linked oligosaccharide assembly does not occur directly on the Asn residues of the protein, but involves preassembly of a lipid-linked precursor oligosaccharide which is then transferred to the protein during or very soon after its translation from mRNA. This precursor oligosaccharide $(Glc_3Man_9GlcNAc_2)$ is synthesized while attached via a pyrophosphate bridge to a polyisoprenoid carrier lipid, a dolichol, with the aid of a number of membrane-bound glycosyltransferases. After assembly of the lipid-linked precursor is complete, another membrane-hound enzyme transfers it to sterically accessible Asn residues which occur as part of the sequence -Asn-X-Ser/Thr-.

Glycosylated Asn residues of newly-synthesized glycoproteins transiently carry only one type of oligosaccharide, $Glc_3Man_9GlcNAc_2$. Processing of this oligosaccharide structure generates the great diversity of structures found on mature glycoproteins.

The processing of N-linked oligosaccharides is accomplished by the sequential action of a number of membrane-bound enzymes and includes removal of the three glucose residues, removal of a variable number of mannose residues, and addition of various sugar residues to the resulting trimmed core.

Depending on the mode of action and necessity for effector function, targeted protein or glycan modifications are being employed to enhance clinical potential of the therapeutics antibodies (Carter, *Exp Cell Res,* 317, 2011, 1261-1269). One of these modifications involves expression of recombinant antibodies that do not have fucose molecule on their chitobiose core (N-linked) glycan (afucosylated), which results in increased ADCC due to their stronger affinity for the FcγRIII, usually expressed on peripheral blood monocytes and natural killer cells (Shields et al., *J Biol Chem,* 277, 2002, 26733-26740). The correlation between antibody fucosylation and reduction in ADCC levels has also been studied and documented by several groups (Shields et al., *J Biol Chem,* 277, 2002, 26733-26740; Kanda et al., *J Biotechnol,* 130, 2007, 300-310; and Yamane-Ohunuki et al., *Biotechnol Bioeng,* 87, 2004, 614-622).

Fucosylation of glycans requires synthesis of GDP-fucose via the de novo or salvage pathway. The fucosylation process involves sequential function of several enzymes resulting in addition of a fucose molecule to the first N-acetylglucosamine (GlcNAc) moiety of the reducing end of a glycan (Becker & Lowe, Glycobiology, 13, 2003, 41R-53R). Laboratories of Lowe and Fukuda discovered the two key enzymes of the de novo pathway responsible for production of GDP-fucose from mannose and/or glucose. Specifically, the laboratories discovered, GDP-D-mannose-4,6-dehydratase (GMD) and GDP-keto-6-deoxymannose-3,5-epimerase,4-reductase (FX) (Ohyama et al., *J Biol Chem,* 273, 1998, 14582-14587; Smith et al., *J Cell Biol,* 158, 2002, 801-815; and Becker, Genetic and Biochemical Determination of Fucosylated Glycan Expression, 2002, Thesis from The University of Michigan, UMI3121891). In the absence of fucose, GMD and FX convert mannose and/or glucose to GDP-fucose. In turn, GDP-fucose, is transported into the Golgi complex where nine fucosyl-transferases (FUT1-9) act in concert to fucosylate the first GlcNAc molecule of a glycan (Becker & Lowe, Glycobiology, 13, 2003, 41R-53R). In the presence of fucose, however, fucose-kinase and GDP-fucose pyrophosphorylase can convert fucose into GDP-fucose, bypassing the need for de novo synthesis of GDP-fucose by GMD and FX enzymes (Becker & Lowe, Glycobiology, 13, 2003, 41R-53R).

Many strategies other than FX knockout (KO) have been utilized to increase the percent afucosylated antibody species expressed by the CHO cell lines in order to enhance ADCC effector function, however, their usage is usually accompanied with particular setbacks. For example, over expression of β(1,4)-N-acetylglucosaminyltransferase III (GNTIII) has been shown to reduce the levels of fucosylated antibodies through increasing levels of bisecting GlcNAc (attachment of a third GlcNAc to the $1^{st}$ mannose of the glycan) intermediate species (Umana et al., *Nat Biotechnol,* 17, 1999, 176-180; Davies et al., *Biotechnol Bioeng,* 74, 2001, 288-294). However, these glycan species are not commonly present on antibodies and maintaining them at a consistent and reproducible levels can be challenging, jeopardizing product quality and consistency in a manufacturing setting. Additionally, reduction in expression levels of recombinant GNTIII over time, due to silencing or DNA copy number loss, makes it difficult to reproducibly express predictable levels of afucosylated antibodies for manufacturing purposes. Likewise, over expression of prokaryotic GDP-6-deoxy-D-lyxo-4-hexulose reductase (RMD) enzyme (von Horsten et al., *Glycobiology,* 20, 2010, 1607-1618), or any approach that utilizes over expression in order to increase percent afucosylated antibody species, could suffer such setbacks. Using knockdown strategies (Imai-Nishiya et al., *BMC Biotechnol,* 7, 2007, *1-13), or commercially available inhibitors of fucosylation pathway is challenging due to knockdown stability or off-target activities of inhibitors that may result in product heterogeneity. Not to mention the cost associated with utilizing chemical inhibitors of fucosylation in a manufacturing setting. Treatment of antibody products post expression or purification with fucosidases (Intra et al., *Gene,* 392, 2007, 34-46) is also inefficient, resulting in lack of product quality inconsistency and complicates manufacturing process due to additional step(s) required for removal of these enzymes.

Utilization of a GMD KO host for expression of afucosylated antibodies has been suggested (Kanda et al., *J Biotechnol,* 130, 2007, 300-310), but such host has not been widely utilized and the reported specific productivity of this host is not very high (Kanda et al., *J Biotechnol,* 130, 2007, 300-310).

FUT8 KO host on the other hand has been widely used to generate clones that can express afucosylated antibodies suitable for manufacturing purposes (Yamane-Ohunuki et al., *Biotechnol Bioeng,* 87, 2004, 614-622; and Malphettes et al., *Biotechnol Bioeng,* 106, 2010, 774-783). Nevertheless, utilizing the FUT8 KO host is not without its shortcomings and challenges. Generally, analysis of antibody function in vivo and in vitro is required to determine necessity and efficacy of afucosylated versus wild type (fucosylated) antibodies. Since FUT8 KO host is only capable of expressing afucosylated antibodies, a parallel cell line development (CLD) effort needs to be undertaken in order to express wild type antibodies for comparison purposes, doubling the required CLD efforts. Furthermore, large numbers of afucosylated and wild type antibody expressing clones need to be screened in order to obtain clones with comparable product quality attributes to ensure that any observed advantages is only due to lack of fucosylation. Additionally, it has been observed that FUT8 KO hosts have growth issues and may require longer suspension adaptation time, increasing the CLD timelines with possible implications for lower titers (Malphettes et al., *Biotechnol Bioeng,* 106, 2010, 774-783).

Thus, there exists a need in the art for a cell line, and methods of culturing said cell line, capable of producing afucosylated and fucosylated forms of a protein at a desired ratio, and compositions comprising the protein thereof.

The disclosures of all publications, patents, patent applications and published patent applications referred to herein are hereby incorporated herein by reference in their entirety.

BRIEF SUMMARY OF THE INVENTION

The present application in some embodiments provides methods of producing a protein, wherein the protein is produced in fucosylated and afucosylated forms at a predetermined ratio, the methods comprising: culturing a host cell engineered to express the protein in a culture medium, wherein the host cell comprises substantially no GDP-keto-6-deoxymannose-3,5-epimerase,4-reductase (FX) activity or substantially no GDP-D-mannose-4,6-dehydratase (GMD) activity, and wherein the culture medium comprises a fucose source in an amount sufficient to produce the fucosylated and afucosylated forms of the protein at the predetermined ratio. In some embodiments, the predetermined ratio is about 50:1 to about 1:50 (including, for example, about 50:5.5, about 50:12.5, about 50:21.5, about 50:33.5, about 50:50, about 50:75, about 50:116.5, about 50:200, or about 50:450).

In some embodiments, there are provided methods of producing a protein having an enhanced ADCC function mediated both by NK cells and PMN cells, the methods comprising: culturing a host cell engineered to express the protein in a culture medium, wherein the host cell comprises substantially no FX activity or substantially no GMD activity, and wherein the culture medium comprises a fucose source in an amount sufficient to produce fucosylated and afucosylated forms of the protein at a ratio that provides the enhanced ADCC function. In some embodiments, the ADCC function is determined by an ADCC assay. In some embodiments, the ADCC function is determined by a FCγRIII binding assay.

In some embodiments, there are provided methods of adjusting a level of fucosylation of a protein produced by a host cell engineered to produce the protein, the methods comprising: culturing the host cell in an initial culture medium, wherein the host cell comprises substantially no FX activity or substantially no GMD activity, and wherein the culture medium comprises a fucose source; determining the level of fucosylation of the protein; and adjusting the amount of the fucose source in the culture medium such that the protein is produced at a predetermined level of fucosylation. In some embodiments, determining the level of fucosylation of the protein comprises determining the fucosylated form of the protein. In some embodiments, determining the level of fucosylation of the protein comprises determining the afucosylated form of the protein. In some embodiments, adjusting the amount of the fucose source comprises increasing amount of the fucose source when the level of fucosylation is low. In some embodiments, adjusting the amount of the fucose source comprises decreasing amount of the fucose source when the level of fucosylation is high.

In some embodiments according to (or as applied to) any of the embodiments above, the method comprises culturing the host cell in a culture medium free of the fucose source prior to culturing the host cell in the culture medium comprising the fucose source. In some embodiments according to (or as applied to) any of the embodiments above, the method comprises culturing the host cell in a culture medium, wherein the fucose source is present in the culture medium at the beginning of the culturing step. In some embodiments according to (or as applied to) any of the embodiments above, the method comprises culturing the host cell in a culture medium, wherein the fucose source is added to the culture medium during the culturing step. In some embodiments, the fucose source is added to the culture medium via bolus addition. In some embodiments, the fucose source is added to the culture medium via continuous feeding.

In some embodiments according to (or as applied to) any of the embodiments above, the method comprises culturing the host cell in a culture medium, wherein the amount of the fucose source in the culture medium during the culturing step is between about 0.01 mM and about 1 mM.

In some embodiments according to (or as applied to) any of the embodiments above, the method comprises culturing the host cell in a culture medium, wherein the culturing step is carried out at lower than about 37° C.

In some embodiments according to (or as applied to) any of the embodiments above, the method comprises culturing the host cell in a culture medium, wherein the culture medium further comprises a glucose source or a mannose source.

In some embodiments according to (or as applied to) any of the embodiments above, the method further comprises isolating the protein from the cell culture.

In some embodiments according to (or as applied to) any of the embodiments above, the fucose source is a fucose. In some embodiments, the fucose is L-fucose. In some embodiments, the fucose is L-fucose-1-phosphate. In some embodiments according to (or as applied to) any of the embodiments above, the fucose source is GDP-fucose.

In some embodiments, there are provided methods of characterizing a protein in an afucosylated form, the methods comprising: comparing the biological activity of the afucosylated protein with a fucosylated form of the protein, wherein the afucosylated and fucosylated forms of the protein are produced by the same host cell engineered to produce the protein, and wherein the host cell comprises substantially no FX activity or substantially no GMD activity. In some embodiments, the afucosylated form of the protein is produced by the host cell in a first cell culture free of a fucose source. In some embodiments, the fucosylated form of the protein is produced by the host cell in a second cell culture comprising a fucose source.

In some embodiments, the method of characterizing a protein in an afucosylated form comprises comparing the biological activity in vitro. In some embodiments, the method of characterizing a protein in an afucosylated form comprises comparing the biological activity in vivo. In some embodiments, the ADCC function is determined by an ADCC assay. In some embodiments, the ADCC function is determined by a FCγRIII binding assay.

In some embodiments according to (or as applied to) any of the embodiments above, the fucosylated form of the protein is determined at a glycan structure level. In some embodiments, PNGase F is used to cleave a glycan structure from the protein. In some embodiments, the fucosylated form of the protein is determined at a glycan structure level, wherein the fucosylated form of the protein is determined by capillary electrophoresis (CE).

In some embodiments according to (or as applied to) any of the embodiments above, the fucosylated form of the protein is determined at a protein level. In some embodiments, the fucosylated form of the protein is determined at a protein level, wherein the fucosylated form of the protein is determined by mass spectrometry (MS).

In some embodiments according to (or as applied to) any of the embodiments above, the protein is an Fc-containing protein. In some embodiments, the Fc-containing protein comprises an antibody heavy chain or a fragment thereof. In some embodiments, the Fc-containing protein is a full length antibody. In some embodiments, the full length antibody is a monoclonal antibody. In some embodiments, the Fc-containing protein is a Fc-containing fusion protein. In some embodiments, the Fc-containing fusion protein is an immunoadhesin.

In some embodiments according to (or as applied to) any of the embodiments above, the host cell is a eukaryotic cell. In some embodiments, the host cell is a mammalian cell. In some embodiments, the mammalian cell is a Chinese hamster ovary (CHO) cell.

In some embodiments according to (or as applied to) any of the embodiments above, the host cell comprises no more than 20% FX or GMD activity as compared to a host cell comprising a wild type FX or GMD gene, respectively, without inactivation.

In some embodiments according to (or as applied to) any of the embodiments above, the FX or GMD gene in the host cell is inactivated. In some embodiments, the FX or GMD gene is inactivated by siRNA. In some embodiments, the FX or GMD gene is inactivated by shRNA. In some embodiments, there is provided a method wherein the FX or GMD gene is inactivated by a sequence deletion. In some embodiments, there is provided a method wherein the FX or GMD gene is inactivated by a sequence addition or substitution. In some embodiments, the FX or GMD gene is inactivated using a clustered, regularly interspaced, short palindromic repeats (CRISPR) system. In some embodiments, the FX or GMD gene is inactivated using a transcription activator-like effector nuclease (TALEN) system. In some embodiments, the FX or GMD gene is inactivated using a zinc-finger nuclease (ZFN) system. In some embodiments, the FX or GMD gene is inactivated using a meganuclease system.

In some embodiments according to (or as applied to) any of the embodiments above, the host cell comprises substantially no FX activity.

In some embodiments according to (or as applied to) any of the embodiments above, the fucose source is a fucose. In some embodiments, the fucose is L-fucose. In some embodiments, the fucose is L-fucose-1-phosphate. In some embodiments according to (or as applied to) any of the embodiments above, the fucose source is GDP-fucose.

Also, provided herein are compositions comprising the protein produced by any one of the methods described herein.

In some embodiments, there are provided compositions comprising a protein having an enhanced ADCC function mediated both by NK cells and PMN cells, wherein the composition comprise afucosylated and fucosylated forms of the protein at a ratio that provides the enhanced ADCC function.

In some embodiments, the composition comprises a fucosylated form of the protein comprising fucose at the reducing end of a glycan structure. In some embodiments, the composition is a pharmaceutical composition. In some embodiments, the composition is a cell culture medium. In some embodiments, the composition is a cell lysate. In some embodiments, the composition is a eluate from a protein purification column.

Also provided herein are cell cultures comprising: a host cell engineered to express a protein, wherein the host cell comprises substantially no FX activity or substantially no GMD activity; and a culture medium comprising a fucose source at about 0.01 mM to about 1 mM.

Also provided herein are methods of treating a disease in an individual in need thereof comprising: administering to the individual a pharmaceutical composition described herein. In some embodiments, the composition is administered parenterally. In some embodiments, the composition is administered intravenously or subcutaneously. In some embodiments, the composition is administered locally. In some embodiments, the composition is administered topically.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE FIGURES

FIG. 2A shows a workflow for inactivating FX.

FIG. 2B shows PCR analysis of Pool-3, Pool-9, and a control for detection of deleted FX alleles. Wild type (WT; inside) and knockout (KO; outside) primers were used in separate reactions. CHO-K1 cells transfected with only gRNA (no Cas9) were used as a control.

FIG. 4A shows PCR analysis of the FX gene using wild type (WT) and knockout (KO) primers. FIG. 4B shows Western blot analysis of FX protein. Note that in the FX blot panel the lower band denoted by asterisk (*) is a non-specific band that is present in all samples. Actin blot is used as loading control.

FIG. 5A shows FACS analysis of clone 3. FIG. 5B shows FACS analysis of clone 5. FIG. 5C shows FACS analysis of clone 6. FIG. 5D shows FACS analysis of clone 7. FIG. 5E shows FACS analysis of clone 9. FIG. 5F shows FACS analysis of clone 11.

FIGS. 6A-6C show the process for producing an antibody using FXKO cell lines and analysis of the glycan structures produced by said FXKO cell lines. FIG. 6A shows a schematic of transfection and pool selection to express antibody-A from pools of FXKO hosts 3-5, 3-7, and 3-11, in presence or absence of fucose in media. CHO-K1 host was used as control. FIG. 6B shows a representative electropherogram profile of antibody-A, expressed by FXKO clone 3-11, subjected to capillary electrophoresis. FIG. 6C shows glycan species detected by capillary electrophoresis from different pools, in presence or absence of fucose. Lack of fucosylation is denoted by "—F". Lower level glycan species are not shown. G0=fucosylated chitobiose core glycan, G1=one galactose on one of the GlcNac branches, G-1=chitobiose core glycan lacking one branched GlcNAc, G1'=positional isomer of G1, G1-1=chitobiose core glycan lacking one branched GlcNAc with one galactose on the remaining branched GlcNAc, G2=two galactoses, one on each branched GlcNAc, Man5=GlcNAc-GlcNAc-5×(mannose), G0-1=chitobiose core glycan lacking one branched GlcNAc, G0-1-F=afucosylated chitobiose core glycan lacking one branched GlcNAc, G0-F=afucosylated chitobiose core glycan, G1-F=afucosylated chitobiose core glycan with one galactose on one of the GlcNAc branches, G1'-F=positional isomer of G1-F, G2-F=afucosylated chitobiose core glycan with two galactoses, one on each branched GlcNAc.

FIG. 7A shows the titer (g/L) of the antibody. FIG. 7B shows the specific productivity (pg/cell-day) of the clones.

FIG. 7C shows the growth of the clones. FIG. 7D shows the percentage of glycan structures that are G0-F (afucosylated chitobiose core glycan) produced by the clones.

FIG. 7E shows the percentage of glycan structures that are G1-F (afucosylated chitobiose core glycan with one galactose on one of the GlcNAc branches) produced by the clones. FIG. 7F shows the percentage of glycan structures that are G0-1-F (afucosylated chitobiose core glycan lacking one branched GlcNAc) produced by the clones.

FIG. 8A shows the percentage of charge variants of purified antibody-A produced by FXKO clones, cultured in either the absence of fucose of the presence of 1 mM fucose, as compared to a CHO-K1 host control. FIG. 8B shows the percentage of aggregation of purified antibody-A produced by FXKO clones, cultured in either the absence of fucose of the presence of 1 mM fucose, as compared to a CHO-K1 host control. FIG. 8C shows the titer (g/L) of antibody-B produced by FXKO clones cultured in the either the absence of fucose of the presence of 1 mM fucose. FIG. 8D shows the percentage of major glycoforms of antibody-B produced by FXKO clones cultured in the either the absence of fucose of the presence of 1 mM fucose. G0=fucosylated chitobiose core glycan, G1=one galactose on one of the GlcNac branches, Man5=GlcNAc-GlcNAc-5×(mannose), G0-F=afucosylated chitobiose core glycan, G1-F=afucosylated chitobiose core glycan with one galactose on one of the GlcNAc branches. FIG. 8E shows the percentage of charge variants of purified antibody-B produced by FXKO clones cultured in either the absence of fucose of the presence of 1 mM fucose. FIG. 8F shows the percentage of aggregation of purified antibody-B produced by FXKO clones cultured in either the absence of fucose of the presence of 1 mM fucose.

FIG. 9A shows the percentage of major glycoforms of antibody-B produced by FXKO clone-1 cultured in a range of fucose concentrations (0-1 mM). FIG. 9B shows the percentage of major glycoforms of antibody-B produced by FXKO clone-2 cultured in a range of fucose concentrations (0-1 mM). G0=fucosylated chitobiose core glycan, G1=one galactose on one of the GlcNac branches, Man5=GlcNAc-GlcNAc-5×(mannose), G0-F=afucosylated chitobiose core glycan, G1-F=afucosylated chitobiose core glycan with one galactose on one of the GlcNAc branches. FIG. 9C shows the titer (g/L) of antibody-B produced by FXKO clone-1 and -2 cultured in a range of fucose concentrations (0-1 mM). FIG. 9D shows the percentage of aggregation of antibody-B produced by FXKO clone-1 and -2 cultured in a range of fucose concentrations (0-1 mM). FIG. 9E shows the percentage of charge variants of antibody-B produced by FXKO clone-1 and -2 cultured in a range of fucose concentrations (0-1 mM).

FIG. 10A shows the ratios of afucosylated to fucosylated glycoforms of antibody-B (IgG1) produced by a FXKO clone cultured in production media with the indicated concentrations of fucose. FIG. 10B shows results from an FcγRIII binding assay of the purified antibody-B antibodies at a non-saturating concentration of 10 µg/ml. FIG. 10C shows the ratios of afucosylated to fucosylated glycan species of antibody-C(IgG1) produced by a FXKO clone cultured in production media with the indicated concentrations of fucose. FIG. 10D shows the % ADCC activity results from an NK-cell based ADCC assay of antibody-C antibodies purified from different fucose-feeding cultures. FIG. 10E shows the percent sum of afucosylated glycans and percent relative ADCC activity of antibody mixtures prepared from cultures with 0 and 1 mM fucose feed.

FIG. 10F shows % ADCC activity relative to the percent sum of afucosylated glycan species. FIG. 10G shows ADCC dose response curves for antibody-C samples with different ratios of fucosylated to afucosylated glycans.

DETAILED DESCRIPTION OF THE INVENTION

Figure 1:
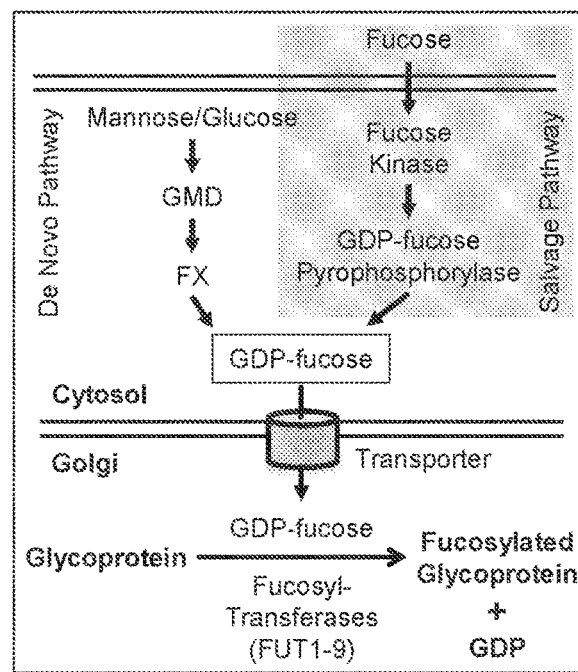
FIG. 1 shows an overview of the fucosylation pathway including the de novo and salvage pathways for generating GDP-fucose. GDP-keto-6-deoxymannose-3,5-epimerase,4-reductase (FX) and GDP-D-mannose-4,6-dehydratase (GMD) are members of the de novo pathway.

The present application utilizes the principle that a GDP-keto-6-deoxymannose-3,5-epimerase,4-reductase knockout (FXKO) cell is capable of producing both fucosylated and afucosylated forms of an antibody when cultured in a culture medium comprising varying amounts of fucose. It was found that titration of fucose in the production media allows for the production of an antibody with a desired ratio of fucosylated and afucosylated glycan forms without any change to the antibody titer or product quality. Clones of the FXKO host cell expressed the target antibody with relatively high specific productivities and good growth profiles.

The present application thus provides methods for producing fucosylated and afucosylated proteins from the same FXKO host cell. This is advantageous as it allows for the production of fucosylated and afucosylated forms of a protein with similar product qualities. In turn, comparison of fucosylated and afucosylated proteins with similar product qualities allows for the determination of whether or not the lack of fucose on an afucosylated protein is indeed responsible for observed changes in biological function (e.g., enhanced ADCC function). In contrast to FUT8 knock out host cells, capable of producing either a wild type or afucosylated form of a protein, the FXKO host obviates the need for undertaking two separate cell line development (CLD) efforts. Furthermore, the use of a single host cell to produce both fucosylated and afucosylated forms of a protein averts the need for screening many colonies to possibly identify clones with comparable product qualities.

Additionally, FXKO clones may be utilized to express any antibody or Fc-containing polypeptide with a therapeutically relevant ratio of fucosylated and afucosylated glycoforms. It has been reported that while afucosylated antibodies enhance ADCC-mediated cell death via mononulcear cells (such as NK cells), polymorphonuclear (PMN) cells preferentially recognize and kill their targets via binding to antibodies with fucosylated glycans (Peipp et al., *Blood*, 112, 2008, 2390-2399). Thus, use of a FXKO host cell, and titration of the correct amount of fucose into the culture medium, can be used to produce a desired ratio of fucosylated and afucosylated forms of an antibody, which in principle should be efficient in enhancing ADCC-mediated cell death by both mononuclear and PMN cells. Furthermore, the capability of adjusting the ratio of fucosylated and afucosylated forms of a protein allows for production of a protein with a maximum level of ADCC function while minimizing any possible ADCC-linked toxicity.

Thus, the present application, in one aspect provides a method of producing a protein in fucosylated and afucosylated forms at a predetermined ratio comprising culturing a host cell with substantially no FX activity or substantially no GMD activity, wherein the culture medium comprises a fucose source in an amount sufficient to produce the fucosylated and afucosylated forms of the protein at the predetermined ratio. The present application, in another aspect, provides a method of producing a protein having an enhanced ADCC function mediated by both NK cells and PMN cells, wherein the host cell comprises substantially no FX activity or substantially no GMD activity, and wherein the culture medium comprises a fucose source in an amount sufficient to produce fucosylated and afucosylated forms of the protein at a ratio that provides the enhanced ADCC function. The present application, in another aspect, provides a method of adjusting a level of protein fucosylation comprising culturing a host cell with substantially no FX activity or substantially no GMD activity, determining the level of fucosylation of the protein, and adjusting the amount of fucose in the culture media such that the protein is produced at a predetermined level of fucosylation. The present application, in another aspect, provides a method of characterizing a protein in an afucosylated form comprising comparing the biological activity of the afucosylated protein with a fucosylated form of the protein, wherein the afucosylated and fucosylated forms of the protein are produced by the same host cell engineered to produce the protein, and wherein the host cell comprises substantially no FX activity or substantially no GMD activity. The present application, in another aspect, provides a composition comprising the protein produced by any of the methods described above. The present application, in another aspect, provides a method of treating a disease comprising administering a pharmaceutical composition comprising the protein. The present application, in another aspect, provides a cell culture comprising the host cell with substantially no FX activity or substantially no GMD activity and a fucose source at about 0.01 mM to about 1 mM.

Definitions

A fucosylated form of a protein, as used herein, refers to a glycan structure having a fucose moiety.

An afucosylated form of a protein, as used herein, refers to a glycan structure lacking a fucose moiety.

"Fc-containing protein," as used herein, refers to a protein (e.g., an antibody or a Fc-containing fusion protein) comprising a Fc domain. In some embodiments, the Fc-containing protein comprises one or more protein subunits. In some embodiments, the Fc-containing protein comprises one or more polypeptides.

"Fc domain," as used herein, refers to a Fc region of an immunoglobulin heavy chain or a C-terminal fragment thereof. The term includes wild type Fc domains and variant Fc domains. In some embodiments, the human IgG heavy chain Fc domain extends from Cys226, or from Pro230, to the carboxyl-terminus of the heavy chain (amino acid number is according to the EU numbering system, also called the EU index, as described in Kabat et al., *Sequences of Proteins of Immunological Interest*, 5th Ed. Public Health Service, National Institutes of Health, Bethesda, Md., 1991). In some embodiments, the term includes a C-terminal fragment of an immunoglobulin heavy chain and one or more constant regions. In some embodiments, for IgG, the Fc domain may comprise immunoglobulin domains CH2 and CH3 and the hinge between CH1 and CH2.

As used herein, "Fc-containing fusion protein" refers to a protein comprising a Fc domain fused to at least one other heterologous protein unit or polypeptide.

The term "heavy chain" used herein refers to an immunoglobulin heavy chain.

Antibodies are glycoproteins, with glycosylation in the Fc region. Thus, for example, the Fc region of an IgG immunoglobulin is a homodimer comprising interchain disulfide-bonded hinge regions, glycosylated CH2 domains bearing N-linked oligosaccharides at asparagine 297 (Asn-297), and non-covalently paired CH3 domains. Glycosylation plays an important role in effector mechanisms mediated FcγRI, FcγRII, FcγRIII, and C1q. Thus, antibody fragments of the present invention must include a glycosylated Fc region and an antigen-binding region.

The term "antibody" herein is used in the broadest sense and encompasses various antibody structures, including but not limited to monoclonal antibodies, polyclonal antibodies, multi specific antibodies (e.g., bispecific antibodies), and antibody fragments so long as they comprise a Fc domain.

The terms "full length antibody," is used herein to refer to an antibody having a structure substantially similar to a native antibody structure or having heavy chains that contain an Fc region as defined herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "chimeric" antibody refers to an antibody in which a portion of the heavy and/or light chain is derived from a particular source or species, while the remainder of the heavy and/or light chain is derived from a different source or species.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., $C_H2$ and/or $C_H3$ sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG1, IgG2, IgG3, or IgG4 subtypes, IgA (including IgA1 and IgA2), IgE, IgD, or IgM.

The term "therapeutic antibody" refers to an antibody that is used in the treatment of disease. A therapeutic antibody may have various mechanisms of action. A therapeutic antibody may bind and neutralize the normal function of a target associated with an antigen. For example, a monoclonal antibody that blocks the activity of the of protein needed for the survival of a cancer cell causes the cell's death. Another therapeutic monoclonal antibody may bind and activate the normal function of a target associated with an antigen. For example, a monoclonal antibody can bind to a protein on a cell and trigger an apoptosis signal. Yet another monoclonal antibody may bind to a target antigen expressed only on diseased tissue; conjugation of a toxic payload (effective agent), such as a chemotherapeutic or radioactive agent, to the monoclonal antibody can create an agent for specific delivery of the toxic payload to the diseased tissue, reducing harm to healthy tissue. A "biologically functional fragment" of a therapeutic antibody will exhibit at least one if not some or all of the biological functions attributed to the intact antibody, the function comprising at least specific binding to the target antigen.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and mediates slower catabolism, thus longer half-life.

"Effector function" refers to those biological activities attributable to the Fc region of an antibody, which vary with the antibody isotype. Examples of antibody effector functions include: C1q binding and complement-dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g., from blood or PBMCs as described herein.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *PNAS (USA)* 95:652-656 (1998).

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., *J. Immunol. Methods* 202:163 (1996), may be performed.

"Host cell," as used herein, refers to a cell capable of producing a protein or polypeptide product. In some embodiments, the host cell can produce a Fc-containing protein.

As used herein, "substantially no FX activity" or "substantially no GMD activity" refers to a reduction of an activity level of FX or GMD, respectively, as compared to a host cell comprising wild type FX or GMD, respectively, without a reduction of the activity level, by at least about 80%, 85%, 90%, 95%, or 100%. In some embodiments, the activity level is reduced by about 80% to 100%, about 85% to 100%, about 90% to 100%, or about 95% to 100%. In some embodiments, the activity level is reduced by at least 95%. In some embodiments, the activity level is reduced by 100%. In some embodiments, the activity level of the enzyme is no more than 20%, as compared to a host cell comprising a wild type enzyme without a reduction of the activity level of the enzyme. In some embodiments, the activity level of the enzyme is no more than 15%, as compared to a host cell comprising a wild type enzyme without a reduction of the activity level of the enzyme. In some embodiments, the activity level of the enzyme is no more than 10%, as compared to a host cell comprising a wild type enzyme without a reduction of the activity level of the enzyme. In some embodiments, the activity level of the enzyme is no more than 5%, as compared to a host cell comprising a wild type enzyme without a reduction of the activity level of the enzyme.

The phrases "disruption of the gene" and "gene disruption" refer to a mutation of the native, endogenous DNA sequence and/or the promoter region of a gene so as to decrease or prevent expression of that gene in the cell as compared to the wild type or naturally occurring sequence of the gene.

The term "knockout" refers to an alteration in the nucleic acid sequence of a gene that reduces the biological activity of the polypeptide normally encoded therefrom by at least 80% compared to the unaltered gene. The alteration, for example, may be an insertion, substitution, deletion, frameshift mutation, or missense mutation.

The term "knockdown" refers to techniques by which the expression of one or more genes is reduced, either through genetic modification (a change in the DNA of one of the organism's chromosomes) or by treatment with a reagent such as a short DNA or RNA oligonucleotide with a sequence complementary to either an mRNA transcript or a gene. If genetic modification of DNA is done, the result is a "knockdown organism" or "knockdown host cell".

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "isolated" protein is one which has been separated from a component of its natural environment. In some embodiments, a protein is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For example, for review of methods for assessment of antibody purity, see, e.g., Flatman et al., *J. Chromatogr. B* 848:79-87 (2007).

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The methods of the invention contemplate any one or more of these aspects of treatment.

The term "individual" refers to a mammal and includes, but is not limited to, human, bovine, horse, feline, canine, rodent, or primate. In some embodiments, the individual is a human.

A "therapeutically effective amount" is at least the minimum concentration required to effect a measurable improvement of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically, but not necessarily, since a prophylactic dose is used in subjects prior to or at the earlier stage of disease, the prophylactically effective amount can be less than the therapeutically effective amount.

It is understood that aspects and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X."

As used herein and in the appended claims, the singular forms "a," "or," and "the" include plural referents unless the context clearly dictates otherwise.

Methods of Producing Fucosylated and Afucosylated Forms of a Protein

The present application, in some aspects, provides methods of producing a protein, wherein the protein is produced in fucosylated and afucosylated forms at a predetermined ratio, wherein the methods comprise culturing any host cell comprising substantially no FX activity or substantially no GMD activity as described in the embodiments herein in a culture medium, and wherein the culture medium comprises a fucose source in an amount sufficient to produce the fucosylated and afucosylated forms of the protein at the predetermined ratio. In some embodiments, there is provided a method of producing a protein, wherein the protein is produced in fucosylated and afucosylated forms at a predetermined ratio, comprising culturing a host cell having FX or GMD gene disruption, and wherein the culture medium comprises a fucose source in an amount sufficient to produce the fucosylated and afucosylated forms of the protein at the predetermined ratio. In some embodiments, there is provided a method of producing an Fc-containing protein, wherein the Fc-containing protein is produced in fucosylated and afucosylated forms at a predetermined ratio, comprising culturing a host cell comprising substantially no FX activity or substantially no GMD activity in a culture medium, wherein the culture medium comprises a fucose source in an amount sufficient to produce the fucosylated and afucosylated forms of the Fc-containing protein at the predetermined ratio. In some embodiments, there is provided a method of producing an Fc-containing protein, wherein the Fc-containing protein is produced in fucosylated and afucosylated forms at a predetermined ratio, comprising culturing a host cell having FX or GMD gene disruption in a culture medium, wherein the culture medium comprises a fucose source in an amount sufficient to produce the fucosylated and afucosylated forms of the Fc-containing protein at the predetermined ratio. In some embodiments, there is provided a method of producing an antibody, wherein the antibody is produced in fucosylated and afucosylated forms at a predetermined ratio, comprising culturing a host cell having substantially no FX activity or substantially no GMD activity in a culture medium, wherein the culture medium comprises a fucose source in an amount sufficient to produce the fucosylated and afucosylated forms of the antibody at the predetermined ratio. In some embodiments, there is provided a method of producing an antibody, wherein the antibody is produced in fucosylated and afucosylated forms at a predetermined ratio, comprising culturing a host cell having FX or GMD gene disruption in a culture medium, wherein the culture medium comprises a fucose source in an amount sufficient to produce the fucosylated and afucosylated forms of the antibody at the predetermined ratio. In some embodiments, the host cell comprises substantially no FX activity. In some embodiments, the host cell comprises substantially no GMD activity. In some embodiments, the host cell comprises substantially no FX activity or substantially no GMD activity. In some embodiments, the host cell is a mammalian cell. In some embodiments, the host cell is a CHO cell. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, there is provided a method of producing a protein, wherein the protein is produced in fucosylated and afucosylated forms at a predetermined ratio, comprising culturing a host cell having substantially no FX activity, wherein the culture medium comprises a fucose source in an amount sufficient to produce the fucosylated and afucosylated forms of the protein at the predetermined ratio. In some embodiments, there is provided a method of producing a protein, wherein the protein is produced in fucosylated and afucosylated forms at a predetermined ratio, comprising culturing a host cell having FX gene disruption, wherein the culture medium comprises a fucose source in an amount sufficient to produce the fucosylated and afucosylated forms of the protein at the predetermined ratio. In some embodiments, there is provided a method of producing an Fc-containing protein, wherein the Fc-containing protein is produced in fucosylated and afucosylated forms at a predetermined ratio, comprising culturing a host cell comprising substantially no FX activity in a culture medium, wherein the culture medium comprises a fucose source in an amount sufficient to produce the fucosylated and afucosylated forms of the Fc-containing protein at the predetermined ratio. In some embodiments, there is provided a method of producing an Fc-containing protein, wherein the Fc-containing protein is produced in fucosylated and afucosylated forms at a predetermined ratio, comprising culturing a host cell having FX gene disruption in a culture medium, wherein the culture medium comprises a fucose source in an amount sufficient to produce the fucosylated and afucosylated forms of the Fc-containing protein at the predetermined ratio. In some embodiments, there is provided a method of producing an antibody, wherein the antibody is produced in fucosylated and afucosylated forms at a predetermined ratio, comprising culturing a host cell having substantially no FX activity in a culture medium, wherein the culture medium comprises a fucose source in an amount sufficient to produce the fucosylated and afucosylated forms of the antibody at the predetermined ratio. In some embodiments, there is provided a method of producing an antibody, wherein the antibody is produced in fucosylated and afucosylated forms at a predetermined ratio, comprising culturing a host cell having FX gene disruption in a culture medium, wherein the culture medium comprises a fucose source in an amount sufficient to produce the fucosylated and afucosylated forms of the antibody at the predetermined ratio. In some embodiments, the host cell is a mammalian cell. In some embodiments, the host cell is a CHO cell. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, the predetermined ratio of fucosylated and afucosylated forms of a protein is about 50:1 to about 1:50, about 50:2.5 to about 1:50, about 50:5.5 to about 1:50, about 50:8.5 to about 1:50, about 50:12.5 to about 1:50, about 50:15.5 to about 1:50, about 50:21.5 to about 1:50, about 50:27 to about 1:50, about 50:33.5 to about 1:50, about 50:41 to about 1:50, about 50:50 to about 1:50, about 50:61 to about 1:50, about 50:75 to about 1:50, about 50:93 to about 1:50, about 50:116.5 to about 1:50, about 50:150 to about 1:50, about 50:200 to about 1:50, about 50:283.5 to about 1:50, about 50:450 to about 1:50, or about 50:950 to about 1:50.

In some embodiments, the predetermined ratio of fucosylated and afucosylated forms of a protein is about 50:1 to about 2.5:50, about 50:1 to about 5.5:50, about 50:1 to about 8.5:50, about 50:1 to about 12.5:50, about 50:1 to about 15.5:50, about 50:1 to about 21.5:50, about 50:1 to about 27:50, about 50:1 to about 33.5:50, about 50:1 to about 41:50, about 50:1 to about 50:50, about 50:1 to about 61:50, about 50:1 to about 75:50, about 50:1 to about 93:50, about 50:1 to about 116.5:50, about 50:1 to about 150:50, about 50:1 to about 200:50, about 50:1 to about 283.5:50, about 50:1 to about 450:50, or about 50:1 to about 950:50.

In some embodiments, the predetermined ratio of fucosylated and afucosylated forms of a protein is about 50:2.5 to about 2.5:50, about 50:5.5 to about 5.5:50, about 50:8.5 to about 8.5:50, about 50:12.5 to about 12.5:50, about 50:15.5 to about 15.5:50, about 50:15.5 to about 21.5:50, about 50:27 to about 27:50, about 50:33.5 to about 33.5:50, or about 50:41 to about 41:50.

In some embodiments, the predetermined ratio of fucosylated and afucosylated forms of a protein is about 12.5:50 to about 2.5:50, about 12.5:50 to about 5.5:50, about 12.5:50 to about 8.5:50, about 12.5:50 to about 12.5:50, or about 12.5:50 to about 15.5:50.

In some embodiments, the predetermined ratio of fucosylated and afucosylated forms of a protein is about 21.5:50 to about 2.5:50, about 21.5:50 to about 5.5:50, about 21.5:50 to about 8.5:50, about 21.5:50 to about 12.5:50, or about 21.5:50 to about 15.5:50.

In some embodiments, the predetermined ratio of fucosylated and afucosylated forms of a protein is about 33.5:50 to about 2.5:50, about 33.5:50 to about 5.5:50, about 33.5:50 to about 8.5:50, about 33.5:50 to about 12.5:50, about 33.5:50 to about 15.5:50, about 33.5:50 to about 21.5:50, or about 33.5:50 to about 27:50.

In some embodiments, the predetermined ratio of fucosylated and afucosylated forms of a protein is about 50:50 to about 2.5:50, about 50:50 to about 5.5:50, about 50:50 to about 8.5:50, about 50:50 to about 12.5:50, about 50:50 to about 15.5:50, about 50:50 to about 21.5:50, about 50:50 to about 27:50, about 50:50 to about 33.5:50, or about 50:50 to about 41:50.

In some embodiments, the predetermined ratio of fucosylated and afucosylated forms of a protein is about 75:50 to about 2.5:50, about 75:50 to about 5.5:50, about 75:50 to about 8.5:50, about 75:50 to about 12.5:50, about 75:50 to about 15.5:50, about 75:50 to about 21.5:50, about 75:50 to about 27:50, about 75:50 to about 33.5:50, about 75:50 to about 41:50, about 75:50 to about 50:50, or about 75:50 to about 61:50.

In some embodiments, the predetermined ratio of fucosylated and afucosylated forms of a protein is about 116.5:50 to about 2.5:50, about 116.5:50 to about 5.5:50, about 116.5:50 to about 8.5:50, about 116.5:50 to about 12.5:50, about 116.5:50 to about 15.5:50, about 116.5:50 to about 21.5:50, about 116.5:50 to about 27:50, about 116.5:50 to about 33.5:50, about 116.5:50 to about 41:50, about 116.5:50 to about 50:50, about 116.5:50 to about 61:50, about 116.5:50 to about 75:50, or about 116.5:50 to about 93:50.

In some embodiments, the predetermined ratio of fucosylated and afucosylated forms of a protein is about 200:50 to about 2.5:50, about 200:50 to about 5.5:50, about 200:50 to about 8.5:50, about 200:50 to about 12.5:50, about 200:50 to about 15.5:50, about 200:50 to about 21.5:50, about 200:50 to about 27:50, about 200:50 to about 33.5:50, about 200:50 to about 41:50, about 200:50 to about 50:50, about 200:50 to about 61:50, about 200:50 to about 75:50, about 200:50 to about 93:50, about 200:50 to about 116.5:50, or about 200:50 to about 150:50.

In some embodiments, the predetermined ratio of fucosylated and afucosylated forms of a protein is about 50:1, about 50:2.5, about 50:5.5, about 50:8.5, about 50:12.5, about 50:15.5, about 50:21.5, about 50:27, about 50:33.5, about 50:41, about 50:50, about 50:61, about 50:75, about 50:93, about 50:116.5, about 50:150, about 50:200, about 50:283.5, about 50:450, or about 50:950.

The amount of a fucose source in a culture medium comprising the fucose source in an amount sufficient to produce the fucosylated and afucosylated forms of the protein at the predetermined ratio is largely dependent on components of the system, such as the type of host cell, number of host cells, protein production rate, and the predetermined ratio of fucosylated and afucosylated forms of a protein. In some embodiments, the fucose source is between about 0.01 mM and about 1 mM. In some embodiments, the fucose source is between about 0.01 mM and about 0.1 mM, about 0.01 mM and about 0.09 mM, about 0.01 mM and about 0.08 mM, about 0.01 mM and about 0.07 mM, about 0.01 mM and about 0.06 mM, about 0.01 mM and about 0.05 mM, about 0.01 mM and about 0.04 mM, about 0.01 mM and about 0.03 mM, about 0.01 mM and about 0.02 mM, about 0.02 mM and about 0.1 mM, about 0.02 mM and about 0.09 mM, about 0.02 mM and about 0.08 mM, about 0.02 mM and about 0.08 mM, about 0.02 mM and about 0.07 mM, about 0.02 mM and about 0.06 mM, about 0.02 mM and about 0.05 mM, about 0.02 mM and about 0.04 mM, about 0.02 mM and about 0.03 mM, about 0.03 mM and about 0.1 mM, about 0.03 mM and about 0.09 mM, about 0.03 mM and about 0.08 mM, about 0.03 mM and about 0.07 mM, about 0.03 mM and about 0.06 mM, about 0.03 mM and about 0.05 mM, about 0.03 mM and about 0.04 mM, about 0.04 mM and about 0.1 mM, about 0.04 mM and about 0.09 mM, about 0.04 mM and about 0.08 mM, about 0.04 mM and about 0.07 mM, about 0.04 mM and about 0.6 mM, about 0.04 mM and about 0.05 mM, about 0.05 mM and about 0.1 mM, about 0.05 mM and about 0.09 mM, about 0.05 mM and about 0.08 mM, about 0.05 mM and about 0.07 mM, about 0.05 mM and about 0.06 mM, about 0.06 mM and about 0.1 mM, about 0.06 mM and about 0.09 mM, about 0.06 mM and about 0.08 mM, about 0.06 mM and about 0.07 mM, about 0.07 mM and about 0.1 mM, about 0.07 mM and about 0.09 mM, about 0.07 mM and about 0.08 mM, about 0.08 mM and about 0.1 mM, about 0.08 mM and about 0.9 mM, or about 0.09 mM and about 0.1 mM. In some embodiments, the fucose source is about 0.01 mM, about 0.02 mM, about 0.03 mM, about 0.04 mM, about 0.05 mM, about 0.06 mM, about 0.07 mM, about 0.08 mM, about 0.09 mM, about 0.1 mM, about 0.11 mM, about 0.12 mM, about 0.13 mM, about 0.14 mM, about 0.15 mM, about 0.16 mM, about 0.17 mM, about 0.18 mM, about 0.19 mM, about 0.2 mM, about 0.3 mM, about 0.4 mM, about 0.5 mM, about 0.6 mM, about 0.7 mM, about 0.8 mM, about 0.9 mM, or about 1 mM.

Also provided herein are methods of producing a protein having an enhanced ADCC function mediated both by NK cells and PMN cells, the methods comprising: culturing a host cell engineered to express the protein in a culture medium, wherein the host cell comprises substantially no FX activity or substantially no GMD activity, and wherein the culture medium comprises a fucose source in an amount sufficient to produce fucosylated and afucosylated forms of the protein at a ratio that provides the enhanced ADCC function. In some embodiments, there is provided a method of producing a protein having an enhanced ADCC function mediated both by NK cells and PMN cells comprising culturing a host cell having FX or GMD gene disruption, wherein the culture medium comprises a fucose source in an amount sufficient to produce fucosylated and afucosylated forms of a protein at a ratio that provides the enhanced ADCC function. In some embodiments, there is provided a method of producing a Fc-containing protein having an enhanced ADCC function mediated both by NK cells and PMN cells comprising culturing a host cell having substantially no FX activity or substantially no GMD activity, wherein the culture medium comprises a fucose source in an amount sufficient to produce fucosylated and afucosylated forms of a protein at a ratio that provides the enhanced ADCC function. In some embodiments, there is provided a method of producing a Fc-containing protein having an enhanced ADCC function mediated both by NK cells and PMN cells comprising culturing a host cell having substantially no FX activity or substantially no GMD activity and engineered to express the Fc-containing protein in a culture medium, wherein the culture medium comprises a fucose source in an amount sufficient to produce fucosylated and afucosylated forms of the Fc-containing protein at a ratio that provides the enhanced ADCC function. In some embodiments, there is provided a method of producing a Fc-containing protein having an enhanced ADCC function mediated both by NK cells and PMN cells comprising culturing a host cell having FX or GMD gene disruption and engineered to express the Fc-containing protein in a culture medium, wherein the culture medium comprises a fucose source in an amount sufficient to produce fucosylated and afucosylated forms of the Fc-containing protein at a ratio that provides the enhanced ADCC function. In some embodiments, there is provided a method of producing an antibody having an enhanced ADCC function mediated both by NK cells and PMN cells comprises culturing a host cell engineered to express the antibody in a culture medium, wherein the host cell comprises substantially no FX activity or substantially no GMD activity, and wherein the culture medium comprises a fucose source in an amount sufficient to produce fucosylated and afucosylated forms of the antibody at a ratio that provides the enhanced ADCC function. In some embodiments, there is provided a method comprising culturing a host cell having FX or GMD gene disruption and engineered to express an antibody in a culture medium, wherein the culture medium comprises a fucose source in an amount sufficient to produce fucosylated and afucosylated forms of the antibody at a ratio that provides the enhanced ADCC function. In some embodiments, the host cell comprises substantially no FX activity. In some embodiments, the host cell comprises substantially no GMD activity. In some embodiments, the host cell comprises substantially no FX and GMD activity. In some embodiments, the host cell is a mammalian cell. In some embodiments, the host cell is a CHO cell. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, there is provided a method of producing a protein having an enhanced ADCC function mediated both by NK cells and PMN cells comprising culturing a host cell having substantially no FX activity, wherein the culture medium comprises a fucose source in an amount sufficient to produce fucosylated and afucosylated forms of a protein at a ratio that provides the enhanced ADCC function. In some embodiments, there is provided a method of producing a protein having an enhanced ADCC function mediated both by NK cells and PMN cells comprising culturing a host cell having FX gene disruption, wherein the culture medium comprises a fucose source in an amount sufficient to produce fucosylated and afucosylated forms of a protein at a ratio that provides the enhanced ADCC function. In some embodiments, there is provided a method of producing a Fc-containing protein having an enhanced ADCC function mediated both by NK cells and PMN cells comprising culturing a host cell having substantially no FX activity, wherein the culture medium comprises a fucose source in an amount sufficient to produce fucosylated and afucosylated forms of a protein at a ratio that provides the enhanced ADCC function. In some embodiments, there is provided a method of producing a Fc-containing protein having an enhanced ADCC function mediated both by NK cells and PMN cells comprising culturing a host cell having substantially no FX activity and engineered to express the Fc-containing protein in a culture medium, wherein the culture medium comprises a fucose source in an amount sufficient to produce fucosylated and afucosylated forms of the Fc-containing protein at a ratio that provides the enhanced ADCC function. In some embodiments, there is provided a method of producing a Fc-containing protein having an enhanced ADCC function mediated both by NK cells and PMN cells comprising culturing a host cell having FX gene disruption and engineered to express the Fc-containing protein in a culture medium, wherein the culture medium comprises a fucose source in an amount sufficient to produce fucosylated and afucosylated forms of the Fc-containing protein at a ratio that provides the enhanced ADCC function. In some embodiments, there is provided a method of producing an antibody having an enhanced ADCC function mediated both by NK cells and PMN cells comprises culturing a host cell engineered to express the antibody in a culture medium, wherein the host cell comprises substantially no FX activity, and wherein the culture medium comprises a fucose source in an amount sufficient to produce fucosylated and afucosylated forms of the antibody at a ratio that provides the enhanced ADCC function. In some embodiments, there is provided a method comprising culturing a host cell having FX gene disruption and engineered to express an antibody in a culture medium, wherein the culture medium comprises a fucose source in an amount sufficient to produce fucosylated and afucosylated forms of the antibody at a ratio that provides the enhanced ADCC function. In some embodiments, the host cell is a mammalian cell. In some embodiments, the host cell is a CHO cell. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, the enhanced ADCC function of a protein is as compared to a protein produced from a wild type host without a reduced level of FX or GMD activity. In some embodiments, the enhanced ADCC function of a protein is as compared to a fucosylated form of the protein. In some embodiments, the enhanced ADCC function of a protein is as compared to a wild type protein. In some embodiments, the ADCC function of a protein is enhanced by about 1-fold, 2-fold, 3-fold, 4-fold, 5-fold, 10-fold, 20-fold, 30-fold, 40-fold, 50-fold, 75-fold, or 100-fold, as compared to a protein produced from a wild type host without a reduced level of FX or GMD activity.

In some embodiments, the ADCC function is determined by an ADCC assay. ADCC assays and methods of determining ADCC function are well known in the art. See, e.g., Tada et al., PLoS One, 9, 2014, e95787; Cheng et al., *J Immunol Methods*, 414, 2014, 69-81. For example, the ADCC function of a protein can be determined by incubating a protein, such as an Fc-containing protein, with an effector cell that expresses a Fc receptor on their surface, such as peripheral blood mononuclear cells (PBMCs) or natural killer cells (NK cells), and target cells. Following engagement of the Fc region of the protein bound to a target disease cell with an Fc receptor, the Fc receptor transduces intracellular signals within the effector cell resulting in elimination of the target cell. Target cell lysis is subsequently measured by release of intracellular label by a scintillation counter or spectrophotometry. Among these methods include chromium-51 release assays, europium release assays, and sulfur-35 release assays. For example, target cell lysis can be assessed, for example, by measuring the release of specific probes from pre-labelled target cells, using $^{51}$Cr or fluorescent dyes, for example, calcein-AM44, carboxyfluorescein succinimidyl ester (CFSE), 2',7'-bis-(2-carboxyethyl)-5-(and-6)-carboxyfluorescein (BCECF) or Europium, or by measuring the release of cytosolic enzymes such as lactate dehydrogenase (LDH) or ATP. Other assay for assessing ADCC function include, for example, a coupled bioluminescent method that measures the release of enzymes naturally present in the target cells (ACELLA™ TOX; Promega). No target cell labeling step is required and no radioactive agents are used.

In some embodiments, the ADCC function of a protein is determined by an ADCC assay, wherein the ADCC assay comprises NK cells. In some embodiments, the ADCC function of a protein is determined by an ADCC assay, wherein the ADCC assay comprises PBMCs. In some embodiments, the ADCC assay is an in vitro assay. In some embodiments, the ADCC assay is an in vivo assay.

In some embodiments, the ADCC function is determined by a FCγIII binding assay. See, e.g., Miller et al., *J Immunol Methods*, 385, 2012, 45-50. Surrogate binding methods may be used for the assessment of ADCC function. Generally, these methods measure complementarity determining region (CDR) binding to the cell surface target antigen, and Fc binding to FcγRs, either separately or simultaneously. Various flow cytometry and plate-based formats can be used for CDR and FcγR binding assays. Recombinant protein receptor binding and C1q binding assays have been developed with a number of platforms, including surface plasmon resonance and enzyme-linked immunosorbent assays. In some embodiments, the ADCC function is determined via an ELISA-based assay.

There are also provided methods of adjusting a level of fucosylation of a protein produced by a host cell engineered to produce the protein, the methods comprising: culturing the host cell in an initial culture medium, wherein the host cell comprises substantially no FX activity or substantially no GMD activity, and wherein the culture medium comprises a fucose source; determining the level of fucosylation of the protein; and adjusting the amount of the fucose source in the culture medium such that the protein is produced in fucosylated and afucosylated forms at a predetermined ratio. In some embodiments, there is provided a method of adjusting a level of fucosylation of a protein produced by a host cell having FX or GMD gene disruption and engineered to produce the protein comprising culturing the host cell in an initial culture medium, and wherein the culture medium comprises a fucose source; determining the level of fucosylation of the protein; and adjusting the amount of the fucose source in the culture medium such that the protein is produced in fucosylated and afucosylated forms at a predetermined ratio. In some embodiments, there is provided a method of adjusting a level of fucosylation of a Fc-containing protein produced by a host cell engineered to produce the protein, comprising culturing the host cell in an initial culture medium, wherein the host cell comprises substantially no FX activity or substantially no GMD activity, and wherein the culture medium comprises a fucose source; determining the level of fucosylation of the Fc-containing protein; and adjusting the amount of the fucose source in the culture medium such that the Fc-containing protein is produced in fucosylated and afucosylated forms at a predetermined ratio. In some embodiments, there is provided a method of adjusting a level of fucosylation of a Fc-containing protein produced by a host cell having FX or GMD gene disruption and engineered to produce the protein, comprising culturing the host cell in an initial culture medium, and wherein the culture medium comprises a fucose source; determining the level of fucosylation of the Fc-containing protein; and adjusting the amount of the fucose source in the culture medium such that the Fc-containing protein is produced in fucosylated and afucosylated forms at a predetermined ratio. In some embodiments, there is provided a method of adjusting a level of fucosylation of an antibody produced by a host cell engineered to produce the antibody, comprising culturing the host cell in an initial culture medium, wherein the host cell comprises substantially no FX activity or substantially no GMD activity, and wherein the culture medium comprises a fucose source; determining the level of fucosylation of the antibody; and adjusting the amount of the fucose source in the culture medium such that the antibody is produced in fucosylated and afucosylated forms at a predetermined ratio. In some embodiments, the method of adjusting a level of fucosylation of an antibody produced by a host cell having FX or GMD gene disruption and engineered to produce the antibody, comprising culturing the host cell in an initial culture medium, wherein the culture medium comprises a fucose source; determining the level of fucosylation of the antibody; and adjusting the amount of the fucose source in the culture medium such that the antibody is produced in fucosylated and afucosylated forms at a predetermined ratio. In some embodiments, the host cell comprises substantially no FX activity. In some embodiments, the host cell comprises substantially no GMD activity. In some embodiments, the host cell comprises substantially no FX and GMD activity. In some embodiments, the host cell is a mammalian cell. In some embodiments, the host cell is a CHO cell. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, there is provided a method of adjusting a level of fucosylation of a protein produced by a host cell having substantially no FX activity and engineered to produce the protein comprising culturing the host cell in an initial culture medium, and wherein the culture medium comprises a fucose source; determining the level of fucosylation of the protein; and adjusting the amount of the fucose source in the culture medium such that the protein is produced in fucosylated and afucosylated forms at a predetermined ratio. In some embodiments, there is provided a method of adjusting a level of fucosylation of a protein produced by a host cell having FX gene disruption and engineered to produce the protein comprising culturing the host cell in an initial culture medium, and wherein the culture medium comprises a fucose source; determining the level of fucosylation of the protein; and adjusting the amount of the fucose source in the culture medium such that the protein is produced in fucosylated and afucosylated forms at a predetermined ratio. In some embodiments, there is provided a method of adjusting a level of fucosylation of a Fc-containing protein produced by a host cell engineered to produce the protein, comprising culturing the host cell in an initial culture medium, wherein the host cell comprises substantially no FX activity, and wherein the culture medium comprises a fucose source; determining the level of fucosylation of the Fc-containing protein; and adjusting the amount of the fucose source in the culture medium such that the Fc-containing protein is produced in fucosylated and afucosylated forms at a predetermined ratio. In some embodiments, there is provided a method of adjusting a level of fucosylation of a Fc-containing protein produced by a host cell having FX gene disruption and engineered to produce the protein, comprising culturing the host cell in an initial culture medium, and wherein the culture medium comprises a fucose source; determining the level of fucosylation of the Fc-containing protein; and adjusting the amount of the fucose source in the culture medium such that the Fc-containing protein is produced in fucosylated and afucosylated forms at a predetermined ratio. In some embodiments, there is provided a method of adjusting a level of fucosylation of an antibody produced by a host cell engineered to produce the antibody, comprising culturing the host cell in an initial culture medium, wherein the host cell comprises substantially no FX activity, and wherein the culture medium comprises a fucose source; determining the level of fucosylation of the antibody; and adjusting the amount of the fucose source in the culture medium such that the antibody is produced in fucosylated and afucosylated forms at a predetermined ratio. In some embodiments, the method of adjusting a level of fucosylation of an antibody produced by a host cell having FX gene disruption and engineered to produce the antibody, comprising culturing the host cell in an initial culture medium, wherein the culture medium comprises a fucose source; determining the level of fucosylation of the antibody; and adjusting the amount of the fucose source in the culture medium such that the antibody is produced in fucosylated and afucosylated forms at a predetermined ratio. In some embodiments, the host cell is a mammalian cell. In some embodiments, the host cell is a CHO cell. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, there is provided a method of determining the level of fucosylation of the protein comprising determining a fucosylated form of the protein. Methods of determining a fucosylated form of a protein are described in the application herein. In some embodiments, determining the level of fucosylation of the protein comprises determining an afucosylated form of the protein. Methods of determining an afucosylated form of a protein are described in the application herein. In some embodiments, determining the level of fucosylation of the protein comprises determining fucosylated and afucosylated forms of the protein.

In some embodiments, the level of fucosylation and/or afucosylation is determined during a culturing step. In some embodiments, the level of fucosylation and/or afucosylation is determined more than one time during culturing of a host cell. In some embodiments, the amount of a fucose source in a culture medium is adjusted after determining a level of fucosylation and/or afucosylation. In some embodiments, the amount of a fucose source is not adjusted after determining a level of fucosylation and/or afucosylation. In some embodiments, the amount of the fucose source is adjusted more than one time during culturing of a host cell.

In some embodiments, there is provided a method of adjusting an amount of a fucose source in an initial culture medium comprising increasing the amount of the fucose source when a level of fucosylation is low. In some embodiments, increasing an amount of a fucose source in an initial culture medium comprises adding a fucose source to the initial culture medium via bolus addition. In some embodiments, increasing an amount of a fucose source in an initial culture medium comprises adding a second culture medium comprising a fucose source to the initial culture medium via bolus addition, wherein the amount of the fucose source in the second culture medium is greater than the amount of fucose in the initial culture medium. In some embodiments, increasing an amount of a fucose source in an initial culture medium comprises adding a fucose source to the initial culture medium via continuous feeding. In some embodiments, increasing an amount of a fucose source in an initial culture medium comprises adding a second culture medium comprising the fucose source to an initial culture medium via continuous feeding, wherein the amount of the fucose source in the second culture medium is greater than the amount of fucose in the initial culture medium.

In some embodiments, there is provided a method of adjusting an amount of a fucose source in an initial culture medium comprising decreasing the amount of a fucose source in the initial culture medium when a level of fucosylation is high. In some embodiments, decreasing an amount of a fucose source in an initial culture medium comprises adding a second culture medium lacking a fucose source. In some embodiments, decreasing the amount of the fucose source in an initial culture medium comprises adding a second culture medium comprising a reduced level of a fucose source as compared to the initial culture medium.

The present application, in some aspects, provides methods of comparing the biological activity of fucosylated and afucosylated forms of a protein comprising: comparing the biological activity of an afucosylated protein with a fucosylated form of the protein, wherein the afucosylated and fucosylated forms of the protein are produced by the same host cell engineered to produce the protein, and wherein the host cell comprises substantially no FX activity or substantially no GMD activity. In some embodiments, there is provided a method comprising comparing the biological activity of an afucosylated protein with a fucosylated form of a protein, wherein the afucosylated and fucosylated forms of the protein are produced by the same host cell having FX or GMD gene disruption and engineered to produce the protein, wherein the host cell comprises substantially no FX activity or substantially no GMD activity. In some embodiments, there is provided a method comprising comparing the biological activity of an afucosylated Fc-containing protein with a fucosylated form of the Fc-containing protein, wherein the afucosylated and fucosylated forms of the Fc-containing protein are produced by the same host cell engineered to produce the Fc-containing protein, and wherein the host cell comprises substantially no FX activity or substantially no GMD activity. In some embodiments, there is provided a method comprising comparing the biological activity of an afucosylated Fc-containing protein with a fucosylated form of the Fc-containing protein, wherein the afucosylated and fucosylated forms of the Fc-containing protein are produced by the same host cell having FX or GMD gene disruption and engineered to produce the Fc-containing protein. In some embodiments, there is provided a method comprising comparing the biological activity of an afucosylated antibody with a fucosylated form of an antibody, wherein the afucosylated and fucosylated forms of the antibody are produced by the same host cell engineered to produce the antibody, and wherein the host cell comprises substantially no FX activity or substantially no GMD activity. In some embodiments, there is provided a method comprising comparing the biological activity of an afucosylated antibody with a fucosylated form of an antibody, wherein the afucosylated and fucosylated forms of the antibody are produced by the same host cell having FX or GMD gene disruption and engineered to produce the antibody. In some embodiments, the host cell comprises substantially no FX activity. In some embodiments, the host cell comprises substantially no GMD activity. In some embodiments, the host cell comprises substantially no FX and GMD activity. In some embodiments, the host cell is a mammalian cell. In some embodiments, the host cell is a CHO cell. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, there is provided a method comprising comparing the biological activity of an afucosylated protein with a fucosylated form of a protein, wherein the afucosylated and fucosylated forms of the protein are produced by the same host cell engineered to produce the protein, wherein the host cell comprises substantially no FX activity. In some embodiments, there is provided a method comprising comparing the biological activity of an afucosylated protein with a fucosylated form of a protein, wherein the afucosylated and fucosylated forms of the protein are produced by the same host cell having FX gene disruption and engineered to produce the protein, wherein the host cell comprises substantially no FX activity. In some embodiments, there is provided a method comprising comparing the biological activity of an afucosylated Fc-containing protein with a fucosylated form of the Fc-containing protein, wherein the afucosylated and fucosylated forms of the Fc-containing protein are produced by the same host cell engineered to produce the Fc-containing protein, and wherein the host cell comprises substantially no FX activity. In some embodiments, there is provided a method comprising comparing the biological activity of an afucosylated Fc-containing protein with a fucosylated form of the Fc-containing protein, wherein the afucosylated and fucosylated forms of the Fc-containing protein are produced by the same host cell having FX gene disruption and engineered to produce the Fc-containing protein. In some embodiments, there is provided a method comprising comparing the biological activity of an afucosylated antibody with a fucosylated form of an antibody, wherein the afucosylated and fucosylated forms of the antibody are produced by the same host cell engineered to produce the antibody, and wherein the host cell comprises substantially no FX activity. In some embodiments, there is provided a method comprising comparing the biological activity of an afucosylated antibody with a fucosylated form of an antibody, wherein the afucosylated and fucosylated forms of the antibody are produced by the same host cell having FX gene disruption and engineered to produce the antibody. In some embodiments, the host cell comprises substantially no FX and GMD activity. In some embodiments, the host cell is a mammalian cell. In some embodiments, the host cell is a CHO cell. In some embodiments, the fucose source is a fucose. In some embodiments, the fucose is L-fucose. In some embodiments, the fucose is L-fucose-1-phosphate. In some embodiments, the fucose source is GDP-fucose.

Production of fucosylated and afucosylated forms of a protein from the same host cell allows for the generation of the forms of the protein with similar product quality attributes and differences of biological activity between the fucosylated and afucosylated forms of the protein to be attributed to the fucosylation status.

In some embodiments, the afucosylated form of a protein is produced by a host cell in a first cell culture free of a fucose source. In some embodiments, the fucosylated form of a protein is produced by a host cell in a second cell culture comprising a fucose source. In some embodiments, there is provided a method comprising: a) producing the afucosylated form of a protein by culturing a host cell in a first cell culture free of a fucose source, b) isolating the afucosylated protein, c) producing the fucosylated form of a protein by culturing the host cell in a second cell culture comprising a fucose source, d) isolating the fucosylated protein, and e) comparing the biological activity of fucosylated and afucosylated forms of the protein. In some embodiments, there is provided a method comprising comparing the biological activity of fucosylated and afucosylated forms of a protein, wherein the fucosylated form of the protein is produced in a first cell culture, and wherein the afucosylated form of the protein is produced in a second cell culture.

In some embodiments, the afucosylated and fucosylated forms of a protein are produced by a host cell in a culture medium comprising a fucose source. In some embodiments, the amount of a fucose source in the culture medium is between about 0.01 mM and about 1 mM. Generally, if afucosylated and fucosylated forms of a protein are produced by a host cell in the same culture medium, it is necessary to separate the fucosylated and afucosylated forms of a protein. Separation of fucosylated and afucosylated forms of a protein can be accomplished using, for example, LCA pull-down techniques. See, e.g., Seth et al., *Dev Dyn*, 239, 2010, 3380-3390; and Jilani et al., *J Histochem Cytochem*, 2003, 51, 597-604.

The biological activity of fucosylated and afucosylated forms of a protein can be compared using isolated fucosylated and afucosylated forms of the protein. In some embodiments, comparing biological activity is carried out in vitro. In some embodiments, comparing biological activity is carried out in vivo. In some embodiments, the biological activity is an ADCC function. In some embodiments, the ADCC function is determined by an ADCC assay. ADCC assays are well known in the art and are described in the application herein. In some embodiments, the ADCC function is determined by a surrogate ADCC assay. Surrogate ADCC assays are well known in the art and are described in the application herein. In some embodiments, the surrogate ADCC assay is a FCγRIII binding assay. In some embodiments, the ADCC function is determined by a FCγRIII binding assay. FCγRIII binding assays are well known in the art and are described in the application herein.

The present application, in some aspects, provides methods of identifying a host cell capable of producing fucosylated and/or afucosylated forms of a protein.

Methods suitable for identifying a host cell capable of producing fucosylated and/or afucosylated forms of a protein are well known in the art. In some embodiments, the identification of a host cell capable of producing a fucosylated protein is determined at the cellular level. In some embodiments, the identification of a host cell capable of producing an afucosylated protein is determined at the cellular level. For example, *lens culinaris* agglutinin (LCA)-based assays can be used to identify a host cell capable of producing fucosylated and/or afucosylated forms of a protein at a cellular level. See, e.g., Okeley et al., *PNAS*, 110, 5404-5409. LCA binds carbohydrates, such as glycans, with a core fucose. Labeled LCA, such as fluorescein (FITC) conjugated LCA (LCA-FITC), can be used to bind fucosylated glycans on a host cell surface. Subsequent use of fluorescence-activated cell sorting (FACS) can be used to identify a host cell that is capable of producing fucosylated and/or afucosylated forms of a protein. In some embodiments, identification of a host cell capable of producing a fucosylated form is performed. In some embodiments, identification of a host cell capable of producing an afucosylated form of a protein is performed. In some embodiments, identification of a host cell capable of producing fucosylated and afucosylated forms of a protein is performed, wherein the host cell is assessed after being cultured in a culture medium comprising fucose, and separately, wherein the host cell is assessed after being cultured in a culture medium lacking fucose.

In some embodiments, the host cell capable of producing a fucosylated form of a protein is identified by fluorescence-activated cell sorting (FACS). In some embodiments, the host cell capable of producing an afucosylated form of a protein is identified by fluorescence-activated cell sorting (FACS). In some embodiments, the host cell capable of producing fucosylated and afucosylated forms of a protein is identified by fluorescence-activated cell sorting (FACS). In some embodiments, the host cell capable of producing a fucosylated form of a protein is identified by a LCA-based assay. In some embodiments, the host cell is stained with a fluorescein (FITC) conjugated lens culinaris agglutinin (LCA). In some embodiments, the host cell capable of producing an afucosylated form of a protein is identified by a LCA-based assay. In some embodiments, the host cell is not stained with a fluorescein (FITC) conjugated lens culinaris agglutinin (LCA).

The present application, in some aspects, provides methods of determining fucosylated and/or afucosylated forms of a protein.

In some embodiments, there is provided a method, wherein the fucosylated form of a protein is determined at a glycan structure level. In some embodiments, there is provided a method, wherein the afucosylated form of a protein is determined at a glycan structure level. As used herein, "glycan structure level" refers to analysis of fucosylation or afucosylation using an isolated glycan structure. Generally, methods of determining fucosylation or afucosylation at the glycan structure level involve cleaving a glycan structure from a protein. Methods for cleaving the glycan structure from a protein are well known in the art. See, e.g., Szabo et al., Anal Chem, 82, 2010, 2588-2593; and Mulloy et al., Essentials of Glycobiology, 2nd Edition, Chapter 47, 2009. In some embodiments, the glycan structure is cleaved via enzymatic cleavage. In some embodiments, the enzyme is specific for an N-linked glycan structure. In some embodiments, PNGase F is used to cleave a glycan structure from a protein.

Isolated glycan structures are then analyzed to determine the composition of the glycan structure, for example, presence or absence of fucosylation. Methods of analyzing glycan structures are well known in the art. See, e.g., Mulloy et al., Essentials of Glycobiology, 2nd Edition, Chapter 47, 2009. Generally, glycan structure mixtures will be separated, for example, by capillary electrophoresis or high-pressure liquid chromatography. Subsequent analytical methods are then used to identify types of glycan structures present in a mixture of glycan structures.

In some embodiments, there is provided a method, wherein the fucosylated form of a glycan structure is determined by capillary electrophoresis (CE). In some embodiments, there is provided a method, wherein the afucosylated form of a glycan structure is determined by CE. In some embodiments, there is provided a method, wherein the fucosylated form of a glycan structure is determined by mass spectrometry (MS). In some embodiments, there is provided a method, wherein the afucosylated form of a glycan structure is determined by MS. In some embodiments, there is provided a method, wherein the fucosylated form of a glycan structure is determined by nuclear magnetic resonance (NMR). In some embodiments, there is provided a method, wherein the afucosylated form of a glycan structure is determined by NMR. In some embodiments, there is provided a method, wherein the fucosylated form of a glycan structure is determined by scintillation, wherein the fucose is a radiolabeled fucose. In some embodiments, there is provided a method, wherein the afucosylated form of a glycan structure is determined by a labeling-based assay, wherein a free reducing end of the glycan structure is labeled with a tag, such as a fluorescent tag.

In some embodiments, there is provided a method, wherein the fucosylated form of a protein is determined at a protein level. In some embodiments, there is provided a method, wherein the afucosylated form of a protein is determined at a protein level. As used herein, "protein level" refers to analysis of fucosylation or afucosylation using a protein bound to a glycan structure (e.g., a glycoprotein). Methods for determining fucosylated and afucosylated forms of a protein at the protein level are well known in the art. See, e.g., Balaguer & Neususs, Anal Chem, 78, 2006, 5384-5393. In some embodiments, the fucosylated form of a protein is determined by mass spectrometry (MS). In some embodiments, there is provided a method, wherein the afucosylated form of a protein is determined by MS. In some embodiments, there is provided a method, wherein the fucosylated form of a protein is determined by top-down MS. In some embodiments, there is provided a method, wherein the afucosylated form of a protein is determined by top-down MS.

In some embodiments, there is provided a method, wherein the fucosylated form of a protein is determined at a glycan structure level and a protein level. In some embodiments, there is provided a method, wherein the afucosylated form of a protein is determined at a glycan structure level and a protein level.

Culture Medium and Methods of Culturing

The host cells used to produce a desired protein described in the embodiments herein may be cultured in a variety of culture media. Generally, the fucose content of said media will be known. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth Enz, 58, 1979, Barnes et al., Anal Biochem, 102, 1980, U.S. Pat. Nos. 4,767,704; 4,657,866; 4,927,762; 4,560,655; or 5,122,469; International Patent Application Nos. WO 90/03430 or WO 87/00195; or U.S. Pat. Reissue No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. In some embodiments, the culture medium further comprises a glucose source. In some embodiments, the culture medium further comprises a mannose source. Any other necessary supplements may also be included at appropriate concentrations that would be known to those skilled in the art.

In some embodiments, the culture medium is free of a fucose source. In some embodiments, the culture medium comprises a fucose source. As used herein, "fucose source" refers to a moiety comprising fucose involved in the fucosylation pathway. In some embodiments, the fucose source is a fucose. In some embodiments, the fucose is L-fucose. In some embodiments, the fucose is L-fucose-1-phosphate. In some embodiments, the fucose source is GDP-fucose. In some embodiments, the culture medium comprises a fucose source, wherein the amount of the fucose source in the culture medium is between about 0.01 mM and about 1 mM. In some embodiments, the fucose source is between about 0.01 mM and about 1 mM. In some embodiments, the fucose source is between about 0.01 mM and about 0.1 mM, about 0.01 mM and about 0.09 mM, about 0.01 mM and about 0.08 mM, about 0.01 mM and about 0.07 mM, about 0.01 mM and about 0.06 mM, about 0.01 mM and about 0.05 mM, about 0.01 mM and about 0.04 mM, about 0.01 mM and about 0.03 mM, about 0.01 mM and about 0.02 mM, about 0.02 mM and about 0.1 mM, about 0.02 mM and about 0.09 mM, about 0.02 mM and about 0.08 mM, about 0.02 mM and about 0.08 mM, about 0.02 mM and about 0.07 mM, about 0.02 mM and about 0.06 mM, about 0.02 mM and about 0.05 mM, about 0.02 mM and about 0.04 mM, about 0.02 mM and about 0.03 mM, about 0.03 mM and about 0.1 mM, about 0.03 mM and about 0.09 mM, about 0.03 mM and about 0.08 mM, about 0.03 mM and about 0.07 mM, about 0.03 mM and about 0.06 mM, about 0.03 mM and about 0.05 mM, about 0.03 mM and about 0.04 mM, about 0.04 mM and about 0.1 mM, about 0.04 mM and about 0.09 mM, about 0.04 mM and about 0.08 mM, about 0.04 mM and about 0.07 mM, about 0.04 mM and about 0.6 mM, about 0.04 mM and about 0.05 mM, about 0.05 mM and about 0.1 mM, about 0.05 mM and about 0.09 mM, about 0.05 mM and about 0.08 mM, about 0.05 mM and about 0.07 mM, about 0.05 mM and about 0.06 mM, about 0.06 mM and about 0.1 mM, about 0.06 mM and about 0.09 mM, about 0.06 mM and about 0.08 mM, about 0.06 mM and about 0.07 mM, about 0.07 mM and about 0.1 mM, about 0.07 mM and about 0.09 mM, about 0.07 mM and about 0.08 mM, about 0.08 mM and about 0.1 mM, about 0.08 mM and about 0.9 mM, or about 0.09 mM and about 0.1 mM. In some embodiments, the fucose source is about 0.01 mM, about 0.02 mM, about 0.03 mM, about 0.04 mM, about 0.05 mM, about 0.06 mM, about 0.07 mM, about 0.08 mM, about 0.09 mM, about 0.1 mM, about 0.11 mM, about 0.12 mM, about 0.13 mM, about 0.14 mM, about 0.15 mM, about 0.16 mM, about 0.17 mM, about 0.18 mM, about 0.19 mM, about 0.2 mM, about 0.3 mM, about 0.4 mM, about 0.5 mM, about 0.6 mM, about 0.7 mM, about 0.8 mM, about 0.9 mM, or about 1 mM.

Methods of culturing a host cell in a culture medium are well known to those in the art. See, e.g., Li et al., MAbs, 2, 2010. In some embodiments, culturing a host cell comprises culturing the host cell in a culture medium free of the fucose source prior to culturing the host cell in the culture medium comprising the fucose source. In some embodiments, the fucose source is present in the culture medium at the beginning of the culturing step. In some embodiments, the fucose source is added to the culture medium during the culturing step. In some embodiments, the fucose source is added at a cell density of, for example, at least $2\times10^5$ cells/mL. In some embodiments, the fucose source is added at an oxygen level of, for example, 50% dissolved $O_2$. In some embodiments, the fucose source is added at a glucose level of, for example, 6 g/L. In some embodiments, the fucose source is present in the culture medium at the beginning of the culturing step, and wherein a fucose source is added during the culturing step. In some embodiments, the fucose source is added to the culture medium during the culturing step via bolus addition. In some embodiments, the fucose source is added to the culture medium during the culturing step via continuous feeding. In some embodiments, the fucose source is added to the culture medium via bolus addition. In some embodiments, the fucose source is added to the culture medium via continuous feeding. In some embodiments, the fucose source is a fucose. In some embodiments, the fucose is L-fucose. In some embodiments, the fucose is L-fucose-1-phosphate. In some embodiments, the fucose source is GDP-fucose.

The culture conditions, such as temperature, pH, and the like, can be those previously used with the host cell selected for expression, and will be apparent to the ordinarily skilled artisan. In some embodiments, the culturing step is carried out at lower than about 37° C., 36° C., 35° C., 34° C., 33° C., 32° C., 31° C., or 30° C. In some embodiments, the culturing step is carried out at lower than about 37° C. In some embodiments, the culturing step is carried out at lower than about 34° C. In some embodiments, the culturing step is carried out at about 37° C. In some embodiments, the culturing step is carried out at about 34° C. In some embodiment, the culturing step is carried out at an initial temperature and then shifted to a second temperature. In some embodiments, the initial temperature is about 37° C. and the second temperature is about 34° C. In some embodiments, the initial temperature is about 34° C. and the second temperature is about 37° C.

Generally, the production of proteins is done on a large scale (such as a commercial scale). To achieve a population of a host cell suitable for commercial scale production, one of ordinary skill in the art will recognize the utility using a stepwise approach to expanding a host cell population. For example, the process involves growing a desired host cell on a smaller scale to allow for an increase in the host cell population, such as a seed train. To further increase the population of the host cell, methods generally involved using the seed train to inoculate a larger culture tank, such as an inoculum tank. Often, a series of inoculum tanks of increasing size are used to expand the population of a host cell, such as an inoculum train. This process will provide a suitable population of a host cell for culture in a production culture. In some embodiments, the production culture is a 1000 L culture tank.

In some embodiments, there is provided a method of making a protein comprising culturing the host cell using a batch feed method. In some embodiments, there is provided a method of making a protein comprising culturing the host cell using a continuous feed method. In some embodiments, there is provided a method of making a Fc-containing protein comprising culturing the host cell using a feed method comprising a batch feed method and a continuous feed method.

The present application, in other aspects, provides a cell culture comprising any host cell described in the embodiments herein and a culture medium comprising a low level of a fucose source. In some embodiments, the cell culture can further comprise afucosylated and fucosylated forms of a protein. In some embodiments, the cell culture can further comprise afucosylated and fucosylated forms of a protein at a specific ratio. In some embodiments, there is provided a cell culture comprising a host cell engineered to express a protein, wherein the host cell comprises substantially no FX activity or substantially no GMD activity, and a culture medium comprising a fucose source at about 0.01 mM to about 1 mM. In some embodiments, there is provided a cell culture comprising a host cell engineered to express a protein, wherein the host cell comprises substantially no FX activity or substantially no GMD activity, and wherein the host cell is a knockout host cell, and a culture medium comprising a fucose source at about 0.01 mM to about 1 mM. In some embodiments, there is provided a cell culture comprising a host cell engineered to express a protein, wherein the host cell comprises substantially no FX activity or substantially no GMD activity, and a culture medium comprising a fucose source at about 0.01 mM to about 1 mM, wherein the protein is a Fc-containing protein. In some embodiments, there is provided a cell culture comprising a host cell engineered to express a protein, wherein the host cell comprises substantially no FX activity or substantially no GMD activity, and wherein the host cell is a knockout host cell, and a culture medium comprising a fucose source at about 0.01 mM to about 1 mM, wherein the protein is a Fc-containing protein. In some embodiments, there is provided a cell culture comprising a host cell engineered to express a protein, wherein the host cell comprises substantially no FX activity or substantially no GMD activity, and a culture medium comprising a fucose source at about 0.01 mM to about 1 mM, wherein the protein is an antibody. In some embodiments, there is provided a cell culture comprising a host cell engineered to express a protein, wherein the host cell comprises substantially no FX activity or substantially no GMD activity, and wherein the host cell is a knockout host cell, and a culture medium comprising a fucose source at about 0.01 mM to about 1 mM, wherein the protein is an antibody. In some embodiments, there is provided a cell culture comprising a host cell that expresses fucosylated and afucosylated forms of a protein at a predetermined ratio. In some embodiments, the host cell comprises substantially no FX activity. In some embodiments, the host cell comprises substantially no GMD activity. In some embodiments, the host cell comprises substantially no FX and GMD activity. In some embodiments, the host cell is a mammalian cell. In some embodiments, the host cell is a CHO cell. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, the cell culture maintains a host cell in an environment for growth. In some embodiments, the cell culture maintains a host cell in an environment for the production of a protein. In some embodiments, the protein is produced in fucosylated and afucosylated forms at a predetermined ratio.

In some embodiments, the culture medium comprises a fucose source at about 0.01 mM to about 1 mM. In some embodiments, the culture medium comprises a fucose source at about 0.01 mM to about 0.1 mM. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, the cell culture is a seed culture. In some embodiments, the cell culture is an inoculum culture. In some embodiments, the inoculum culture is a primary inoculum culture. In some embodiments, the inoculum culture is a secondary inoculum. In some embodiments, the cell culture system comprises a production culture.

In some embodiments, the cell culture is maintained at a specified temperature. In some embodiments, the specified temperature is about 15° C. to about 45° C. In some embodiments, the specified temperature is about 30° C. In some embodiments, the specified temperature is less than about 37° C. In some embodiments, the specified temperature is less than about 35° C. In some embodiments, the specified temperature is less than about 34° C.

In some embodiments, the cell culture is maintained at a specified pH. In some embodiments, the cell culture is maintained at a specified dissolved oxygen concentration. In some embodiments, the cell culture is maintained at a specified nutrient level.

In some embodiments, the cell culture system comprises a protein as described in the embodiments herein. In some embodiments, the cell culture comprises a plurality of proteins as described in the embodiments herein. In some embodiments, the cell culture comprises a composition comprising a protein as described in the embodiments herein.

Host Cells

The present application provides, in some aspects, a host cell for expression of a protein, wherein the host cell comprises substantially no FX activity or substantially no GMD activity.

Among the host cells that may be employed are eukaryotic cells, such as yeast or higher eukaryotic cells. Higher eukaryotic cells include insect cells and established cell lines of mammalian origin.

Examples of suitable mammalian host cell include the COS-7 line of monkey kidney cells (ATCC CRL 1651) (Gluzman et al., Cell, 23, 1981), L cells, 293 cells, C127 cells, 3T3 cells (ATCC CCL 163), Chinese hamster ovary (CHO) cells, or their derivatives such as Veggie CHO and related cell lines which grow in serum-free media (Rasmussen et al., *Cytotechnology*, 28, 1998), HeLa cells, BHK (ATCC CRL10) cell lines, and the CVI/EBNA cell line derived from the African green monkey kidney cell line CVI (ATCC CCL 70) as described by McMahan et al., *EMBO J*, 10, 1991, human embryonic kidney cells such as 293, 293 EBNA, or MSR 293, human epidermal A431 cells, human Colo205 cells, other transformed primate cell lines, normal diploid cells, cell strains derived from in vitro culture of primary tissue, primary explants, HL-60, U937, HaK, or Jurkat cells. Optionally, for example, mammalian cell lines such as HepG2/3B, KB, NIH 3T3 or S49, can be used as host cells.

In some embodiments, the host cell is a CHO cell. CHO cells are well known in the art. See, e.g., Xu et al., *Nat Biotechnol*, 29, 2011. In some embodiments, the host cell is a DP12 host cell. In some embodiments, the host cell is a DUXB-11 derived DHFR-deficient DP12 host cell. In some embodiments, the host cell is a CHO-K1 host cell. In some embodiments, the host cell is a DHFR-positive CHO-K1 host cell. In some embodiments, the host cell is a CHOK1M host cell.

In some embodiments, the host cell is a mouse host cell. In some embodiments, the host cell is a Sp2/0 host cell. In some embodiments, the host cell is a NS0 host cell.

In some embodiments, the host cell is a hybridoma. In some embodiments, the hybridoma is an antibody-producing cell, wherein the antibody-producing cell is collected from a host following immunization of the host with an antigen. In some embodiments, the antibody-producing cell is fused with a myeloma cell. In some embodiments, the host cell is a mouse myeloma-derived cell line.

Alternatively, the host cell can be a lower eukaryote such as yeast. Suitable yeasts include *Saccharomyces cerevisiae, Schizosaccharomyces pombe, Kluyveromyces strains, Candida*, or any yeast strain capable of expressing heterologous polypeptides.

As used herein, "substantially no FX activity or substantially no GMD activity," refers to a host cell comprising no more than 40% FX or GMD activity as compared to a host cell comprising a wild type FX or GMD gene, respectively, without inactivation. In some embodiments, the host cell comprises no more than 40%, 35%, 30%, 25%, 20%, 15%, 10%, or 5% FX or GMD activity as compared to a host cell comprising a wild type FX or GMD gene, respectively, without inactivation. In some embodiments, the host cell comprises no more than 20%, 15%, 10%, or 5% FX activity as compared to a host cell comprising a wild type FX gene without inactivation. In some embodiments, the host cell comprises no FX activity as compared to a host cell comprising a wild type FX gene without inactivation. In some embodiments, the host cell comprises no more than 20%, 15%, 10%, or 5% GMD activity as compared to a host cell comprising a wild type GMD gene without inactivation. In some embodiments, the host cell comprises no GMD activity as compared to a host cell comprising a wild type GMD gene without inactivation. In some embodiments, the host cell comprises no more than 20%, 15%, 10%, or 5% FX and GMD activity as compared to a host cell comprising a wild type FX and GMD gene without inactivation. In some embodiments, the host cell comprises no FX and GMD activity as compared to a host cell comprising a wild type FX and GMD gene without inactivation.

FX and GMD are enzymes that belong to the salvage pathway and produce GPD-fucose from L-fucose. See, Becker and Lowe, et al., *Biochim Biophys Acta*, 1455, 1999, 193-204. In the cytosol, FX converts L-fucose to L-fucose-1-phosphate and GMD converts L-fucose-1-phosphate to GPD-fucose. GPD-fucose is then transported to the Golgi lumen where is serves as a substrate used to fucosylate glycan structure.

In some embodiments, the FX or GMD gene in a host cell is inactivated. As used herein, "inactivated" refers to inhibiting the translation, or potential future translation, of a functional gene (i.e., expression of a functional enzyme). Inactivation can occur at any stage or process of gene expression, including, but not limited to, transcription, translation, and protein expression, and inactivation can affect any gene or gene product including, but not limited to, DNA, RNA, such as mRNA, and polypeptides.

In some embodiments, the FX or GMD gene in the host cell is inactivated, wherein FX or GMD activity is based on a DNA level. In some embodiments, the FX or GMD gene in the host cell is inactivated, wherein FX or GMD activity is based on a RNA level. In some embodiments, the FX or GMD gene in the host cell is inactivated, wherein FX or GMD activity is based on a polypeptide level.

Provided in the present application are also methods of producing a knockout host cell. For example, methods include, but are not limited to use of CRISPR, TALEN, ZFN, and meganuclease systems. In some embodiments, the host cell comprises a gene deletion or gene addition or substitution.

Generally, the methods of producing a host cell comprising substantially no FX activity or substantially no GMD activity comprise inactivating the FX or GMD gene of the host cell. Methods and techniques for inactivating the FX or GMD gene in a host cell include, but are not limited to, small interfering RNA (siRNA), small hairpin RNA (shRNA; also referred to as a short hairpin RNA), clustered, regularly interspaced, short palindromic repeats (CRISPR), transcription activator-like effector nuclease (TALEN), zinc-finger nuclease (ZFN), homologous recombination, non-homologous end-joining, meganuclease, and enzyme inhibition. See, e.g., O'Keefe, Mater Methods, 3, 2013; Doench et al., Nat Biotechnol, 32, 2014; Gaj et al., Trends Biotechnol, 31, 2014; and Silva et al., Curr Gene Ther, 11, 2011.

Generally, the CRISPR system used herein can comprise a caspase protein, such as Cas9, and an RNA sequence comprising a nucleotide sequence, referred to as a guide sequence, that is complementary to a sequence of interest. The caspase and RNA sequence form a complex that identify a DNA sequence of a host cell, and subsequently the nuclease activity of the caspase allows for cleavage of the DNA strand. Caspases isotypes have single-stranded DNA or double-stranded DNA nuclease activity. Design of guide RNA sequences and number of guide RNA sequences used in a CRISPR system allow for removal of a specific stretch of a gene and/or addition of a DNA sequence.

In some embodiments, there is provided a method of producing a host cell, wherein the host cell comprises substantially no FX activity or substantially no GMD activity, comprising inactivating the FX or GMD gene using a CRISPR system. In some embodiments, there is provided a method of producing a host cell comprising inactivating the FX or GMD gene using a CRISPR system comprising a coding vector. In some embodiments, there is provided a method of producing a host cell comprising inactivating the FX or GMD gene using a CRISPR system comprising a coding vector comprising a DNA endonuclease gene. In some embodiments, there is provided a method of producing a host cell comprising inactivating the FX or GMD gene using a CRISPR system comprising a coding vector comprising a CAS gene. In some embodiments, there is provided a method of producing a host cell comprising inactivating the FX or GMD gene using a CRISPR system comprising a coding vector comprising a CAS9 gene. In some embodiments, there is provided a method of producing a host cell comprising inactivating the FX or GMD gene using a CRISPR system comprising a coding vector encoding a CAS9 gene. In some embodiments, there is provided a method of producing a host cell comprising inactivating the FX or GMD gene using a CRISPR system comprising a Cas protein. In some embodiments, there is provided a method of producing a host cell comprising inactivating the FX or GMD gene using a CRISPR system comprising a Cas9 protein. In some embodiments, there is provided a method of producing a host cell comprising inactivating a FX or GMD gene using a CRISPR system comprising a coding vector encoding a RNA molecule capable of interacting with the Cas9 protein. In some embodiments, there is provided a method of producing a host cell comprising inactivating the FX or GMD gene using a CRISPR system comprising a coding vector encoding a RNA molecule comprising a guide RNA (gRNA) unit, wherein the gRNA unit comprises a nucleotide sequence that is complementary to a portion of a FX or GMD gene sequence. In some embodiments, there is provided a method of producing a host cell comprising inactivating the FX or GMD gene using a CRISPR system comprising a RNA molecule comprising a gRNA unit, wherein the gRNA unit comprises a nucleotide sequence that is complementary to a portion of a FX or GMD gene sequence. In some embodiments, there is provided a method of producing a host cell comprising inactivating the FX or GMD gene using a CRISPR system comprising a coding vector encoding a RNA molecule comprising a trans-activating crRNA (tracrRNA) unit. In some embodiments, there is provided a method of producing a host cell comprising inactivating the FX or GMD gene using a CRISPR system comprising a RNA molecule comprising a tracrRNA unit. In some embodiments, there is provided a method of producing a host cell comprising inactivating the FX or GMD gene using a CRISPR system comprising a coding vector encoding a RNA molecule comprising a gRNA unit and a tracrRNA unit, wherein the gRNA unit comprises a nucleotide sequence that is complementary to a portion of a gene sequence. In some embodiments, there is provided a method of producing a host cell comprising inactivating the FX or GMD gene using a CRISPR system comprising a RNA molecule comprising a gRNA unit and a tracrRNA unit, wherein the gRNA unit comprises a nucleotide sequence that is complementary to a portion of a FX or GMD gene sequence. In some embodiments, there is provided a method of producing a host cell comprising inactivating the FX or GMD gene using a CRISPR system comprising: a) a first RNA molecule comprising a gRNA unit, wherein the gRNA unit comprises a first nucleotide sequence that is complementary to a portion of a FX or GMD gene sequence; and b) a second RNA molecule comprising a gRNA unit, wherein the gRNA unit comprises a second nucleotide sequence that is complementary to a portion of a FX or GMD gene sequence. In some embodiments, the first nucleotide sequence and second nucleotide sequence are different. In some embodiments, the first nucleotide sequence is complementary to a portion of a FX or GMD gene sequence that is in a different location than the region of the portion of the FX or GMD gene that is complementary to the second nucleotide sequence.

In some embodiments, there is provided a method of producing a host cell comprising delivering a CRISPR system to the host cell. In some embodiments, there is provided a method of producing a host cell comprising delivering a vector comprising a CRISPR system using a delivery vector. In some embodiments, the delivery vector is a virus vector. In some embodiments, the delivery vector is a lentivirus. In some embodiments, the delivery vector is an adenovirus. In some embodiments, the vector comprises a promoter.

Generally, the TALEN system used herein can comprise one or more restriction nucleases and two or more protein complexes that allow for recognition of a DNA sequence and subsequent double-stranded DNA cleavage. A protein complex of the TALEN system comprises a number of transcription activator-like effectors (TALEs), each recognizing a specific nucleotide, and a domain of a restriction nuclease. Generally, a TALEN system is designed so that two protein complexes, each comprising TALEs and a domain of a restriction nuclease, will individually bind to DNA sequences in a manner to allow for the two domains (one from each protein complex) of a restriction nuclease to form an active nuclease and cleave a specific DNA sequence. Design of number of protein complexes and sequences to be cleaved in a TALEN system allows for removal of a specific stretch of a gene and/or addition of a DNA sequence.

In some embodiments, there is provided a method of producing a host cell, wherein the host cell has a reduced level of FX or GMD activity, comprising inactivating the FX or GMD gene using a TALEN system. In some embodiments, there is provided a method of producing a host cell comprising inactivating the FX or GMD gene using a TALEN system comprising a first TALEN unit. In some embodiments, the first TALEN unit comprises a first TALEN binding unit. In some embodiments, the first TALEN binding unit comprises at least one transcription activator-like effector (TALE) and a first nuclease domain. In some embodiments, the first TALEN binding unit comprises at least 3, 4, 5, 6, 7, 8, 9, 10, 11, 12, 13, 14, or 15 TALEs and a first nuclease domain, wherein the TALEs are linked together, and wherein the linked TALEs recognize a portion of a FX or GMD nucleotide sequence. In some embodiments, the first TALEN binding unit comprises at least 3, 4, 5, 6, 7, 8, 9, 10, 11, 12, 13, 14, or 15 TALEs and a first nuclease domain, wherein the TALEs are linked together, wherein the linked TALEs recognize a portion of a FX or GMD nucleotide sequence, and wherein the linked TALEs are further linked to the first nuclease domain. In some embodiments, the first TALEN unit further comprises a second TALEN binding unit. In some embodiments, the second TALEN binding unit comprises at least one transcription activator-like effector (TALE) and a second nuclease domain. In some embodiments, the second TALEN binding unit comprises at least 3, 4, 5, 6, 7, 8, 9, 10, 11, 12, 13, 14, or 15 TALEs and a second nuclease domain, wherein the TALEs are linked together, and wherein the linked TALEs recognize a portion of a FX or GMD nucleotide sequence. In some embodiments, the second TALEN binding unit comprises at least 3, 4, 5, 6, 7, 8, 9, 10, 11, 12, 13, 14, or 15 TALEs and a second nuclease domain, wherein the TALEs are linked together, wherein the linked TALEs recognize a portion of a FX or GMD nucleotide sequence, and wherein the linked TALEs are further linked to the second nuclease domain. In some embodiments, the first TALEN binding unit and second TALEN binding unit bind to different sequences of the FX or GMD gene. In some embodiments, the first nuclease domain is a domain of an endonuclease. In some embodiments, the first nuclease domain is a domain of a restriction endonuclease. In some embodiments, the first nuclease domain is a domain of Fok1. In some embodiments, the second nuclease domain is a domain of an endonuclease. In some embodiments, the second nuclease domain is a domain of a restriction endonuclease. In some embodiments, the second nuclease domain is a domain of Fok1. In some embodiments, the first nuclease domain and second nuclease domain associate to comprise an active restriction endonuclease. In some embodiments, the first nuclease domain and second nuclease domain associate to comprise an active Fok1 enzyme.

In some embodiments, there is provided a method of producing a host cell comprising inactivating the FX or GMD gene using a TALEN system further comprising a second TALEN unit. In some embodiments, the second TALEN unit comprises a third TALEN binding unit. In some embodiments, the third TALEN binding unit comprises at least one transcription activator-like effector (TALE) and a third nuclease domain. In some embodiments, the third TALEN binding unit comprises at least 3, 4, 5, 6, 7, 8, 9, 10, 11, 12, 13, 14, or 15 TALEs and a third nuclease domain, wherein the TALEs are linked together, and wherein the linked TALEs recognize a portion of a FX or GMD nucleotide sequence. In some embodiments, the third TALEN binding unit comprises at least 3, 4, 5, 6, 7, 8, 9, 10, 11, 12, 13, 14, or 15 TALEs and a third nuclease domain, wherein the TALEs are linked together, wherein the linked TALEs recognize a portion of a FX or GMD nucleotide sequence, and wherein the linked TALEs are further linked to the third nuclease domain. In some embodiments, the second TALEN unit further comprises a fourth TALEN binding unit. In some embodiments, the fourth TALEN binding unit comprises at least one transcription activator-like effector (TALE) and a fourth nuclease domain. In some embodiments, the fourth TALEN binding unit comprises at least 3, 4, 5, 6, 7, 8, 9, 10, 11, 12, 13, 14, or 15 TALEs and a fourth nuclease domain, wherein the TALEs are linked together, and wherein the linked TALEs recognize a portion of a FX or GMD nucleotide sequence. In some embodiments, the fourth TALEN binding unit comprises at least 3, 4, 5, 6, 7, 8, 9, 10, 11, 12, 13, 14, or 15 TALEs and a fourth nuclease domain, wherein the TALEs are linked together, wherein the linked TALEs recognize a portion of a FX or GMD nucleotide sequence, and wherein the linked TALEs are further linked to the fourth nuclease domain. In some embodiments, the third TALEN binding unit and fourth TALEN binding unit bind to different sequences of the FX or GMD gene. In some embodiments, the third nuclease domain is a domain of an endonuclease. In some embodiments, the third nuclease domain is a domain of a restriction endonuclease. In some embodiments, the third nuclease domain is a domain of Fok1. In some embodiments, the fourth nuclease domain is a domain of an endonuclease. In some embodiments, the fourth nuclease domain is a domain of a restriction endonuclease. In some embodiments, the fourth nuclease domain is a domain of Fok1. In some embodiments, the third nuclease domain and fourth nuclease domain associate to comprise an active restriction endonuclease. In some embodiments, the third nuclease domain and fourth nuclease domain associate to comprise an active Fok1 enzyme.

In some embodiments, there is provided a method of producing a host cell, wherein the host cell has substantially no FX activity or substantially no GMD activity, comprising inactivating the FX or GMD gene using a TALEN system, wherein the TALEN system comprises a first TALEN unit and a second TALEN unit that bind to different, non-overlapping portions of a FX or GMD gene sequence.

In some embodiments, there is provided a method of producing a host cell, wherein the host cell has substantially no FX activity or substantially no GMD activity, comprising inactivating the FX or GMD gene using a TALEN system, wherein the TALEN system comprises a coding vector encoding a first TALEN unit. In some embodiments, there is provided a method of producing a host cell, wherein the host cell has substantially no FX activity or substantially no GMD activity, comprising inactivating the FX or GMD gene using a TALEN system, wherein the TALEN system comprises a coding vector encoding a first TALEN unit, wherein the TALEN system comprises a coding vector encoding a second TALEN unit. In some embodiments, there is provided a method of producing a host cell, wherein the host cell has substantially no FX activity or substantially no GMD activity, comprising inactivating the FX or GMD gene using a TALEN system, wherein the TALEN system comprises a coding vector encoding a first TALEN unit, wherein the TALEN system comprises a coding vector encoding a first TALEN unit and a second TALEN unit.

In some embodiments, there is provided a method of producing a host cell, wherein the host cell has substantially no FX activity or substantially no GMD activity, comprising inactivating the FX or GMD gene using a TALEN system, wherein the TALEN system comprises a first TALEN unit. In some embodiments, there is provided a method of producing a host cell, wherein the host cell has substantially no FX activity or substantially no GMD activity, comprising inactivating the FX or GMD gene using a TALEN system, wherein the TALEN system comprises a second TALEN unit. In some embodiments, there is provided a method of producing a host cell, wherein the host cell has substantially no FX activity or substantially no GMD activity, comprising inactivating the FX or GMD gene using a TALEN system, wherein the TALEN system comprises a first TALEN unit and a second TALEN unit.

In some embodiments, the first TALEN binding unit comprises a group of linked TALEs, wherein the group of TALEs recognize a nucleotide sequence. In some embodiments, the nucleotide sequence is a sequence comprising a portion of a FX or GMD gene. In some embodiments, the nucleotide sequence is a sequence comprising a portion of a FX or GMD gene promoter. In some embodiments, the nucleotide sequence is a sequence comprising a portion of a sequence flanking a FX or GMD gene. In some embodiments, the sequence is at least about 80%, at least about 85%, at least about 90%, at least about 95%, or 100% homologous to a portion of a FX or GMD gene. In some embodiments, the sequence is at least about 80%, at least about 85%, at least about 90%, at least about 95%, or 100% homologous to a portion of a FX or GMD gene promoter. In some embodiments, the sequence is at least about 80%, at least about 85%, at least about 90%, at least about 95%, or 100% homologous to a portion of a sequence flanking a FX or GMD gene.

In some embodiments, there is provided a method of producing a host cell comprising delivering a TALEN system to the host cell. In some embodiments, there is provided a method of producing a host cell comprising delivering a vector comprising a TALEN system using a delivery vector. In some embodiments, the delivery vector is a virus vector. In some embodiments, the delivery vector is a lentivirus. In some embodiments, the delivery vector is an adenovirus.

Generally, the ZFN system used herein can comprise one or more restriction nucleases and two or more protein complexes that allow for recognition of a DNA sequence and subsequent double-stranded DNA cleavage. A protein complex of the ZFN system comprises a number of zinc fingers, each recognizing a specific nucleotide codon, and a domain of a restriction nuclease. Generally, a ZFN system is designed so that two protein complexes, each comprising zinc fingers and a domain of a restriction nuclease, will individually bind to DNA sequences in a manner to allow for the two domains (one from each protein complex) of a restriction nuclease to form an active nuclease and cleave a specific DNA sequence. Design of number of protein complexes and sequences to be cleaved in a ZFN system allows for removal of a specific stretch of a gene and/or addition of a DNA sequence.

In some embodiments, there is provided a method of producing a host cell, wherein the host cell has substantially no FX activity or substantially no GMD activity, comprising inactivating the FX or GMD gene using a ZFN system. In some embodiments, there is provided a method of producing a host cell comprising inactivating the FX or GMD gene using a ZFN system comprising a first ZFN unit. In some embodiments, the first ZFN unit comprises a first ZFN binding unit. In some embodiments, the first ZFN binding unit comprises at least one zinc finger and a first nuclease domain. In some embodiments, the first ZFN binding unit comprises at least 2, 3, 4, 5, 6, 7, 8, 9, or 10 zinc fingers and a first nuclease domain, wherein the zinc fingers are linked together, and wherein the linked zinc fingers recognize a portion of a FX or GMD nucleotide sequence. In some embodiments, the first ZFN binding unit comprises at least 2, 3, 4, 5, 6, 7, 8, 9, or 10 zinc fingers and a first nuclease domain, wherein the zinc fingers are linked together, wherein the linked zinc fingers recognize a portion of a FX or GMD nucleotide sequence, and wherein the linked zinc fingers are further linked to the first nuclease domain. In some embodiments, the first ZFN unit further comprises a second ZFN binding unit. In some embodiments, the second ZFN binding unit comprises at least one zinc finger and a second nuclease domain. In some embodiments, the second ZFN binding unit comprises at least 2, 3, 4, 5, 6, 7, 8, 9, or 10 zinc fingers and a second nuclease domain, wherein the zinc fingers are linked together, and wherein the linked zinc fingers recognize a portion of a FX or GMD nucleotide sequence. In some embodiments, the second ZFN binding unit comprises at least 2, 3, 4, 5, 6, 7, 8, 9, or 10 zinc fingers and a second nuclease domain, wherein the zinc fingers are linked together, wherein the linked zinc fingers recognize a portion of a FX or GMD nucleotide sequence, and wherein the linked zinc fingers are further linked to the second nuclease domain. In some embodiments, the first ZFN binding unit and second ZFN binding unit bind to different sequences of the FX or GMD gene. In some embodiments, the first nuclease domain is a domain of an endonuclease. In some embodiments, the first nuclease domain is a domain of a restriction endonuclease. In some embodiments, the first nuclease domain is a domain of Fok1. In some embodiments, the second nuclease domain is a domain of an endonuclease. In some embodiments, the second nuclease domain is a domain of a restriction endonuclease. In some embodiments, the second nuclease domain is a domain of Fok1. In some embodiments, the first nuclease domain and second nuclease domain associate to comprise an active restriction endonuclease. In some embodiments, the first nuclease domain and second nuclease domain associate to comprise an active Fok1 enzyme.

In some embodiments, there is provided a method of producing a host cell comprising inactivating the FX or GMD gene using a ZFN system further comprising a second ZFN unit. In some embodiments, the second ZFN unit comprises a third ZFN binding unit. In some embodiments, the third ZFN binding unit comprises at least one zinc finger and a third nuclease domain. In some embodiments, the third ZFN binding unit comprises at least 2, 3, 4, 5, 6, 7, 8, 9, or 10 zinc fingers and a third nuclease domain, wherein the zinc fingers are linked together, and wherein the linked zinc fingers recognize a portion of a FX or GMD nucleotide sequence. In some embodiments, the third ZFN binding unit comprises at least 2, 3, 4, 5, 6, 7, 8, 9, or 10 zinc fingers and a third nuclease domain, wherein the zinc fingers are linked together, wherein the linked zinc fingers recognize a portion of a FX or GMD nucleotide sequence, and wherein the linked zinc fingers are further linked to the third nuclease domain. In some embodiments, the second ZFN unit further comprises a fourth ZFN binding unit. In some embodiments, the fourth ZFN binding unit comprises at least one zinc finger and a fourth nuclease domain. In some embodiments, the fourth ZFN binding unit comprises at least 2, 3, 4, 5, 6, 7, 8, 9, or 10 zinc fingers and a fourth nuclease domain, wherein the zinc fingers are linked together, and wherein the linked zinc fingers recognize a portion of a FX or GMD nucleotide sequence. In some embodiments, the fourth ZFN binding unit comprises at least 2, 3, 4, 5, 6, 7, 8, 9, or 10 zinc fingers and a fourth nuclease domain, wherein the zinc fingers are linked together, wherein the linked zinc fingers recognize a portion of a FX or GMD nucleotide sequence, and wherein the linked zinger fingers are further linked to the fourth nuclease domain. In some embodiments, the third ZFN binding unit and fourth ZFN binding unit bind to different sequences of the FX or GMD gene. In some embodiments, the third nuclease domain is a domain of an endonuclease. In some embodiments, the third nuclease domain is a domain of a restriction endonuclease. In some embodiments, the third nuclease domain is a domain of Fok1. In some embodiments, the fourth nuclease domain is a domain of an endonuclease. In some embodiments, the fourth nuclease domain is a domain of a restriction endonuclease. In some embodiments, the fourth nuclease domain is a domain of Fok1. In some embodiments, the third nuclease domain and fourth nuclease domain associate to comprise an active restriction endonuclease. In some embodiments, the third nuclease domain and fourth nuclease domain associate to comprise an active Fok1 enzyme.

In some embodiments, there is provided a method of producing a host cell, wherein the host cell has substantially no FX activity or substantially no GMD activity, comprising inactivating the FX or GMD gene using a ZFN system, wherein the ZFN system comprises a first ZFN unit and a second TALEN unit that bind to different, non-overlapping portions of a FX or GMD gene sequence.

In some embodiments, there is provided a method of producing a host cell, wherein the host cell has substantially no FX activity or substantially no GMD activity, comprising inactivating the FX or GMD gene using a ZFN system, wherein the ZFN system comprises a coding vector encoding a first ZFN unit. In some embodiments, there is provided a method of producing a host cell, wherein the host cell has substantially no FX activity or substantially no GMD activity, comprises inactivating the FX or GMD gene using a ZFN system, wherein the ZFN system comprises a coding vector encoding a first ZFN unit, wherein the ZFN system comprises a coding vector encoding a second ZFN unit. In some embodiments, there is provided a method of producing a host cell, wherein the host cell has substantially no FX activity or substantially no GMD activity, comprising inactivating the FX or GMD gene using a ZFN system, wherein the ZFN system comprises a coding vector encoding a first ZFN unit, wherein the ZFN system comprises a coding vector encoding a first ZFN unit and a second ZFN unit.

In some embodiments, there is provided a method of producing a host cell, wherein the host cell has substantially no FX activity or substantially no GMD activity, comprising inactivating the FX or GMD gene using a ZFN system, wherein the ZFN system comprises a first ZFN unit. In some embodiments, there is provided a method of producing a host cell, wherein the host cell has substantially no FX activity or substantially no GMD activity, comprising inactivating the FX or GMD gene using a ZFN system, wherein the ZFN system comprises a second ZFN unit. In some embodiments, there is provided a method of producing a host cell, wherein the host cell has substantially no FX activity or substantially no GMD activity, comprising inactivating the FX or GMD gene using a ZFN system, wherein the ZFN system comprises a first ZFN unit and a second ZFN unit.

In some embodiments, the first ZFN binding unit comprises a group of linked zinc fingers, wherein the group of zinc fingers recognize a nucleotide sequence. In some embodiments, the nucleotide sequence is a sequence comprising a portion of a FX or GMD gene. In some embodiments, the nucleotide sequence is a sequence comprising a portion of a FX or GMD gene promoter. In some embodiments, the nucleotide sequence is a sequence comprising a portion of a sequence flanking a FX or GMD gene. In some embodiments, the sequence is at least about 80%, at least about 85%, at least about 90%, at least about 95%, or 100% homologous to a portion of a FX or GMD gene. In some embodiments, the sequence is at least about 80%, at least about 85%, at least about 90%, at least about 95%, or 100% homologous to a portion of a FX or GMD gene promoter. In some embodiments, the sequence is at least about 80%, at least about 85%, at least about 90%, at least about 95%, or 100% homologous to a portion of a sequence flanking a FX or GMD gene.

In some embodiments, there is provided a method of producing a host cell comprising delivering a ZFN system to the host cell. In some embodiments, there is provided a method of producing a host cell comprising delivering a vector comprising a ZFN system using a delivery vector. In some embodiments, the delivery vector is a virus vector. In some embodiments, the delivery vector is a lentivirus. In some embodiments, the delivery vector is an adenovirus.

Generally, the meganuclease system used herein can comprise one or more meganucleases that allow for recognition of a DNA sequence and subsequent double-stranded DNA cleavage.

In some embodiments, there is provided a method of producing a host cell, wherein the host cell has a substantially no FX activity or substantially no GMD activity, comprising inactivating the FX of GMD gene using a meganuclease system. In some embodiments, the meganuclease has a DNA recognition sequence that is about 8 to about 35 nucleotide base pairs in length. In some embodiments, the meganuclease has a DNA recognition sequence that is about 12 to about 30 nucleotide base pairs in length. In some embodiments, the DNA recognition sequence is a sequence comprising a portion of a FX or GMD gene. In some embodiments, the DNA recognition sequence is a sequence comprising a portion of a FX or GMD gene promoter. In some embodiments, the DNA recognition sequence is a sequence comprising a portion of a sequence flanking a FX or GMD gene.

In some embodiments, there is provided a method of producing a host cell comprising delivering a meganuclease system to the host cell. In some embodiments, there is provided a method of producing a host cell comprising delivering a vector comprising a meganuclease system using a delivery vector. In some embodiments, the delivery vector is a virus vector. In some embodiments, the delivery vector is a lentivirus. In some embodiments, the delivery vector is an adenovirus.

In some embodiments, there is provided a method of producing a host cell, wherein the host cell has a substantially no FX activity or substantially no GMD activity, further comprising determining a level of FX or GMD activity. In some embodiments, there is provided a method of producing a host cell comprising determining the level of FX or GMD activity, wherein a FX or GMD gene deletion is detected. In some embodiments, there is provided a method of producing a host cell comprising determining the level of FX or GMD activity, wherein a FX or GMD gene addition or substitution is detected. In some embodiments, there is provided a method of producing a host cell comprising determining the level of FX or GMD activity, wherein a level of FX or GMD expression is determined prior to inactivating a gene in a host cell. In some embodiments, there is provided a method of producing a host cell comprising determining the level of FX or GMD activity, wherein a level of FX or GMD activity is determined after using a CRISPR system to inactive the FX or GMD gene in a host cell. In some embodiments, there is provided a method of producing a host cell comprising determining the level of FX of GMD activity, wherein a level of FX or GMD activity is determined after using a TALEN system to inactive the FX or GMD gene in a host cell. In some embodiments, there is provided a method of producing a host cell comprising determining the level of FX or GMD activity, wherein a level of FX or GMD activity is determined after using a ZFN system to inactive the FX or GMD gene in a host cell. In some embodiments, there is provided a method of producing a host cell comprising determining the level of FX or GMD gene inactivation, wherein a level of FX or GMD activity is determined after using a meganuclease system to inactive the FX or GMD gene in a host cell.

In some of the methods disclosed herein, the FX or GMD activity level is determined at the DNA level. In some embodiments, the FX or GMD activity level is determined at the RNA level. In some embodiments, there is provided a method of producing a host cell comprising determining the FX or GMD activity level using PCR. In some embodiments, there is provided a method of producing a host cell comprising determining the FX or GMD activity level using PCR, wherein a variant sequence is detected. In some embodiments, there is provided a method of producing a host cell comprising determining the FX or GMD activity level using qPCR. In some embodiments, there is provided a method of producing a host cell comprising determining the FX or GMD activity level using qPCR.

In some of the methods disclosed herein, the FX or GMD activity level can be determined at the protein level. In some embodiments, there is provided a method of producing a host cell comprising determining the FX or GMD activity level using immunohistochemistry. In some embodiments, there is provided a method of producing a host cell comprising determining the FX or GMD activity level using Western blot. In some embodiments, there is provided a method of producing a host cell comprising determining the FX or GMD activity level using flow cytometry.

In some embodiments, the level of FX or GMD gene inactivation is determined by comparing the level of FX or GMD activity after FX or GMD gene inactivation to a control value. In some embodiments, the level of FX or GMD gene inactivation is determined by comparing a level of FX or GMD activity after FX or GMD gene inactivation to a level of FX or GMD activity prior to FX or GMD gene inactivation.

In some embodiments, the FX or GMD gene is inactivated by a small interfering RNA (siRNA) system, wherein a host cell will comprise the siRNA system.

In some embodiments, the siRNA system comprises a siRNA nucleotide sequence that is about 10 to 200 nucleotides in length, or about 10 to 100 nucleotides in length, or about 15 to 100 nucleotides in length, or about 10 to 60 nucleotides in length, or about 15 to 60 nucleotides in length, or about 10 to 50 nucleotides in length, or about 15 to 50 nucleotides in length, or about 10 to 30 nucleotides in length, or about 15 to 30 nucleotides in length. In some embodiments, the siRNA nucleotide sequence is approximately 10-25 nucleotides in length. In some embodiments, the siRNA nucleotide sequence is approximately 15-25 nucleotides in length. In some embodiments, the siRNA nucleotide sequence is at least about 10, at least about 15, at least about 20, or at least about 25 nucleotides in length. In some embodiments, the siRNA system comprises a nucleotide sequence that is at least about 80%, at least about 85%, at least about 90%, at least about 95%, or 100% complementary to a region of a FX or GMD mRNA molecule. In some embodiments, the siRNA system comprises a nucleotide sequence that is at least at least about 80%, at least about 85%, at least about 90%, at least about 95%, or 100% complementary to a region of a FX or GMD pro-mRNA molecule. In some, embodiments, the siRNA system comprises a double stranded RNA molecule. In some embodiments, the siRNA system comprises a single stranded RNA molecule. In some embodiments, the host cell comprises a siRNA system as described in the any of the embodiments herein. In some embodiments, the host cell comprises a pro-siRNA nucleotide sequence that is processed into an active siRNA molecule as described in the any of the embodiments herein. In some embodiments, the host cell comprises a siRNA nucleotide sequence that is at least about 80%, at least about 85%, at least about 90%, at least about 95%, or 100% complementary to a region of a FX or GMD mRNA molecule. In some embodiments, the host cell comprises an expression vector encoding a siRNA molecule as described in the any of the embodiments herein. In some embodiments, the host cell comprises an expression vector encoding a pro-siRNA molecule as described in the any of the embodiments herein.

In some embodiments, the siRNA system comprises a delivery vector. In some embodiments, the host cell comprises a delivery vector. In some embodiments, the delivery vector comprises the pro-siRNA and/or siRNA molecule.

In some embodiments, the FX or GMD gene is inactivated by a small hairpin RNA (shRNA; also referred to as a short hairpin RNA) system, wherein a host cell will comprise the shRNA system. Gene inactivation by shRNA systems are well known in the art. In some embodiments, the shRNA system comprises a nucleotide sequence that is about 10 to 200 nucleotides in length, or about 10 to 100 nucleotides in length, or about 15 to 100 nucleotides in length, or about 10 to 60 nucleotides in length, or about 15 to 60 nucleotides in length, or about 10 to 50 nucleotides in length, or about 15 to 50 nucleotides in length, or about 10 to 30 nucleotides in length, or about 15 to 30 nucleotides in length. In some embodiments, the shRNA nucleotide sequence is approximately 10-25 nucleotides in length. In some embodiments, the shRNA nucleotide sequence is approximately 15-25 nucleotides in length. In some embodiments, the shRNA nucleotide sequence is at least about 10, at least about 15, at least about 20, or at least about 25 nucleotides in length. In some embodiments, the shRNA system comprises a nucleotide sequence that is at least about 80%, at least about 85%, at least about 90%, at least about 95%, or 100% complementary to a region of a FX or GMD mRNA molecule. In some embodiments, the shRNA system comprises a nucleotide sequence that is at least about 80%, at least about 85%, at least about 90%, at least about 95%, or 100% complementary to a region of a FX or GMD pro-mRNA molecule. In some, embodiments, the shRNA system comprises a double stranded RNA molecule. In some embodiments, the shRNA system comprises a single stranded RNA molecule. In some embodiments, the host cell comprises a shRNA system as described in the any of the embodiments herein. In some embodiments, the host cell comprises a pre-shRNA nucleotide sequence that is processed in an active shRNA nucleotide sequence as described in any of the embodiments herein. In some embodiments, the pro-shRNA molecule composed of DNA. In some embodiments, the pro-shRNA molecule is a DNA construct. In some embodiments, the host cell comprises a shRNA nucleotide sequence that is at least about 80%, at least about 85%, at least about 90%, at least about 95%, or 100% complementary to a region of a FX or GMD mRNA molecule. In some embodiments, the host cell comprises an expression vector encoding a shRNA molecule as described in the any of the embodiments herein. In some embodiments, the host cell comprises an expression vector encoding a pro-shRNA molecule as described in the any of the embodiments herein.

In some embodiments, the shRNA system comprises a delivery vector. In some embodiments, the host comprises a delivery vector. In some embodiments, the delivery vector comprises the pro-shRNA and/or shRNA molecule.

In some embodiments, the FX or GMD gene is inactivated, wherein a host cell comprises a gene deletion. As used herein, "gene deletion" refers to removal of at least a portion of a DNA sequence, such as a single nucleic acid, from, or in proximity to, a gene. In some embodiments, the sequence subjected to gene deletion comprises an exonic sequence of a gene. In some embodiments, the sequence subjected to gene deletion comprises a promoter sequence of a gene. In some embodiments, the sequence subjected to gene deletion comprises a flanking sequence of a gene. In some embodiments, a portion of a gene sequence is removed from a gene. In some embodiments, a portion of the FX or GMD gene sequence is removed from, or in proximity to, the FX or GMD gene. In some embodiments, the complete gene sequence is removed from a chromosome. In some embodiments, the complete FX or GMD sequence is removed from a chromosome. In some embodiments, the host cell comprises a gene deletion as described in the any of the embodiments herein. In some embodiments, the host cell comprises a gene deletion in the FX or GMD gene. In some embodiments, the host cell comprises a gene deletion in proximity to the FX or GMD gene.

In some embodiments, the FX or GMD gene is inactivated, wherein a host cell comprises a gene addition or substitution. As used herein, "gene addition" or "gene substitution" refers to an alteration of a gene sequence, including insertion or substitution of one or more nucleotides or nucleotide base pairs. In some embodiments, the intronic sequence of the gene is altered. In some embodiments, the exonic sequence of the gene is altered. In some embodiments, the promoter sequence of the gene is altered. In some embodiments, the flanking sequence of the gene is altered. In some embodiments, one nucleotide or nucleotide base pair is added to a gene sequence. In some embodiments, at least one consecutive nucleotide or nucleotide base pair is added to a gene sequence. In some embodiments, the host cell comprises a gene addition or substitution as described in the any of the embodiments herein. In some embodiments, the host cell comprises a gene addition or gene substitution in the FX or GMD gene. In some embodiments, the host cell comprises a gene addition or gene substitution in the FX and GMD gene.

In some embodiments, the FX or GMD gene is inactivated by a gene deletion, wherein deletion of at least one nucleotide or nucleotide base pair in a gene sequence results in a non-functional gene product. In some embodiments, the FX or GMD gene is inactivated by a gene deletion, wherein deletion of at least one nucleotide to a gene sequence results in a gene product that no longer has the original gene product function or activity. In some embodiments, the FX or GMD gene is inactivated by a gene deletion, wherein deletion of at least one nucleotide to a gene sequence results in a dysfunctional gene product.

In some embodiments, the FX or GMD gene is inactivated by a gene addition or substitution, wherein addition or substitution of at least one nucleotide or nucleotide base pair into the FX or GMD gene sequence results in a non-functional gene product. In some embodiments, the FX or GMD gene is inactivated by a gene inactivation, wherein incorporation or substitution of at least one nucleotide to the FX or GMD gene sequence results in a gene product that no longer has the original gene product function or activity. In some embodiments, the FX or GMD gene is inactivated by a gene addition or substitution, wherein incorporation or substitution of at least one nucleotide into the FX or GMD gene sequence results in a dysfunctional gene product.

In some embodiments, the host cell comprises a non-functional FX or GMD gene product. In some embodiments, the host cell comprises a FX or GMD gene product that does not have the original FX or GMD gene product function or activity, respectively. In some embodiments, the host cell comprises a dysfunctional FX or GMD gene product.

In some embodiments, the host cell comprises an inactivated FX or GMD gene, wherein the inactivated FX or GMD gene will not express a full length, and functional, FX or GMD gene product (e.g., a full length FX or GMD polypeptide sequence), respectively. In some embodiments, the host cell comprises an inactivated FX or GMD gene, wherein the inactivated FX or GMD gene will not express an endogenous FX or GMD gene product sequence, respectively. In some embodiments, the host cell comprises an inactivated FX or GMD gene, wherein the inactivated FX or GMD gene will express a variant FX or GMD gene product, respectively. In some embodiments, the host cell comprises a variant FX or GMD gene product.

In some embodiments, the host cell comprises a delivery vector. In some embodiments, the delivery vector is a virus vector. In some embodiments, the delivery vector is a lentivirus. In some embodiments, the delivery vector is an adenovirus. In some embodiments, the vector comprises a promoter.

In some embodiments, the host cell is a stable knockdown host cell. In some embodiments, the host cell is a stable FX or GMD knockdown cell line. In some embodiments, the host cell is a transient knockdown cell line. In some embodiments, the host cell is a transient FX or GMD knockdown cell line.

In some embodiments, the FX or GMD gene is inactivated by a small interfering RNA (siRNA) system. Methods for identifying siRNA sequences suitable for FX or GMD gene inactivation are well known in the art. For example, general consideration for developing and identifying siRNA to target the FX or GMD gene include: a) first search sequences that are preferably 21-23 nucleotides in length (followed by reduction of sequence length as necessary), b) avoid regions within 50-100 base pairs of the start codon and the termination codon, c) avoid intron regions, d) avoid stretches of four or more bases, e.g., AAAA, e) avoid regions with GC content that is less than 30% or greater than 60%, f) avoid repeats and low sequence complexity, g) avoid single nucleotide polymorphism sites, and h) avoid sequences that are complementary to sequences in other off-target genes. See, e.g., Rules of siRNA design for RNA interference, Protocol Online, May 29, 2004; and Reynolds et al., Nat Biotechnol, 22, 2004.

In some embodiments, there is provided a method of producing a host cell, wherein the host cell comprises substantially no FX activity or substantially no GMD activity, comprising inactivating the FX or GMG gene using a siRNA system. In some embodiments, there is provided a method of producing a host cell comprising inactivating the FX or GMD gene using a siRNA system comprising a siRNA nucleotide sequence that is about 10 to 200 nucleotides in length, or about 10 to 100 nucleotides in length, or about 15 to 100 nucleotides in length, or about 10 to 60 nucleotides in length, or about 15 to 60 nucleotides in length, or about 10 to 50 nucleotides in length, or about 15 to 50 nucleotides in length, or about 10 to 30 nucleotides in length, or about 15 to 30 nucleotides in length. In some embodiments, there is provided a method of producing a host cell comprising inactivating the FX or GMD gene using a siRNA system comprising a siRNA nucleotide sequence that is approximately 10-25 nucleotides in length. In some embodiments, there is provided a method of producing a host cell comprising inactivating the FX or GMD gene using a siRNA system comprising a siRNA nucleotide sequence that is approximately 15-25 nucleotides in length. In some embodiments, there is provided a method of producing a host cell comprising inactivating the FX or GMD gene using a siRNA system comprising a siRNA nucleotide sequence that is at least about 10, at least about 15, at least about 20, or at least about 25 nucleotides in length. In some embodiments, there is provided a method of producing a host cell comprising inactivating the FX or GMD gene using a siRNA system comprising a nucleotide sequence that is at least about 80%, at least about 85%, at least about 90%, at least about 95%, or 100% complementary to a region of a FX or GMD mRNA molecule. In some embodiments, there is provided a method of producing a host cell comprising inactivating the FX or GMD gene using a siRNA system comprising a siRNA nucleotide sequence that is at least at least about 80%, at least about 85%, at least about 90%, at least about 95%, or 100% complementary to a region of a FX or GMD pro-mRNA molecule. In some embodiments, there is provided a method of producing a host cell comprising inactivating the FX or GMD gene using a siRNA system comprising a double stranded RNA molecule. In some embodiments, there is provided a method of producing a host cell comprising inactivating the FX or GMD gene using a siRNA system comprising a single stranded RNA molecule.

In some embodiments, there is provided a method of producing a host cell comprising delivering a siRNA system to a host cell. In some embodiments, there is provided a method of producing a host cell comprising delivering a siRNA system to a host cell, wherein the siRNA system comprises a siRNA nucleotide sequence. In some embodiments, there is provided a method of producing a host cell comprising delivering a siRNA system to the host cell using electroporation. In some embodiments, there is provided a method of producing a host cell comprising delivering a siRNA system to the host cell using transfection techniques. In some embodiments, there is provided a method of producing a host cell comprising delivering a siRNA system to the host cell using a virus.

In some embodiments, there is provided a method of producing a host cell, wherein the host cell comprises substantially no FX activity or substantially no GMD activity, further comprising determining the level of FX or GMD activity in the host cell. In some embodiments, determining the level of FX or GMD activity comprises determining a level of FX or GMD activity prior to delivering a siRNA nucleotide sequence to a host cell. In some embodiments, determining the level of FX or GMD activity comprises determining a level of FX or GMD activity after delivering a siRNA nucleotide sequence to a host cell. In some embodiments, the level of FX or GMD activity is determined at the RNA level. In some embodiments, there is provided a method of determining a level of FX or GMD activity comprising determining the level of FX or GMD activity using PCR. In some embodiments, the level of FX or GMD activity is determined at the protein level. In some embodiments, there is provided a method of determining a level of FX or GMD activity comprising determining the FX or GMD activity level using immunohistochemistry. In some embodiments, there is provided a method of determining a level of FX or GMD activity comprising determining the FX or GMD activity level using Western blot. In some embodiments, there is provided a method of determining a level of FX or GMD activity comprising determining the FX or GMD activity level using flow cytometry. In some embodiments, the level of FX or GMD activity is determined by comparing a level of FX or GMD activity after delivery of a siRNA to a control value. In some embodiments, the level of FX or GMD activity is determined by comparing a level of FX or GMD activity after delivery of a siRNA to a wild type value. In some embodiments, the level of FX or GMD activity is determined by comparing a level of FX or GMD activity after delivery of a siRNA to a level of FX or GMD activity prior to delivery of a FX or GMD siRNA, respectively. In some embodiments, the FX or GMD activity level is based on an expression level of a FX or GMD gene, such as expression of FX or GMD RNA and/or protein. In some embodiments, the FX or GMD activity level is based on an expression level of a FX or GMD protein.

In some embodiments, there is provided a method of producing a host cell, wherein the host cell comprises substantially no FX activity or substantially no GMD activity, comprising inactivating the FX or GMD gene using a shRNA system. In some embodiments, there is provided a method of producing a host cell comprising inactivating the FX or GMD gene using a shRNA system comprising a shRNA nucleotide sequence that is about 10 to 200 nucleotides in length, or about 10 to 100 nucleotides in length, or about 15 to 100 nucleotides in length, or about 10 to 60 nucleotides in length, or about 15 to 60 nucleotides in length, or about 10 to 50 nucleotides in length, or about 15 to 50 nucleotides in length, or about 10 to 30 nucleotides in length, or about 15 to 30 nucleotides in length. In some embodiments, there is provided a method of producing a host cell comprising inactivating the FX or GMD gene using a shRNA system comprising a shRNA nucleotide sequence that is approximately 10-25 nucleotides in length. In some embodiments, there is provided a method of producing a host cell comprising inactivating the FX or GMD gene using a shRNA system comprising a shRNA nucleotide sequence that is approximately 15-25 nucleotides in length. In some embodiments, there is provided a method of producing a host cell comprising inactivating the FX or GMD gene using a shRNA system comprising a shRNA nucleotide sequence that is at least about 10, at least about 15, at least about 20, or at least about 25 nucleotides in length. In some embodiments, there is provided a method of producing a host cell comprising inactivating the FX or GMD gene using a shRNA system comprising a nucleotide sequence that is at least about 80%, at least about 85%, at least about 90%, at least about 95%, or 100% complementary to a region of a FX or GMD mRNA molecule. In some embodiments, there is provided a method of producing a host cell comprising inactivating the FX or GMD gene using a shRNA system comprising a shRNA nucleotide sequence that is at least at least about 80%, at least about 85%, at least about 90%, at least about 95%, or 100% complementary to a region of a FX or GMD pro-mRNA molecule. In some embodiments, there is provided a method of producing a host cell comprising inactivating the FX or GMD gene using a shRNA system comprising a double stranded RNA molecule. In some embodiments, there is provided a method of producing a host cell comprising inactivating the FX or GMD gene using a shRNA system comprising a single stranded RNA molecule.

In some embodiments, there is provided a method of producing a host cell comprising delivering a shRNA system to a host cell. In some embodiments, there is provided a method of producing a host cell comprising delivering a shRNA system to a host cell, wherein the shRNA system comprises a shRNA nucleotide sequence. In some embodiments, there is provided a method of producing a host cell comprising delivering a shRNA system to the host cell using electroporation. In some embodiments, there is provided a method of producing a host cell comprising delivering a shRNA system to the host cell using transfection techniques. In some embodiments, there is provided a method of producing a host cell comprising delivering a shRNA system to the host cell using a virus.

In some embodiments, there is provided a method of producing a host cell, wherein the host cell comprises substantially no FX activity or substantially no GMD activity, further comprising determining a level of FX or GMD activity in the host cell. In some embodiments, determining a level of FX or GMD activity comprises determining the level of FX or GMD activity prior to delivering a shRNA nucleotide sequence to a host cell. In some embodiments, determining a level of FX or GMD activity comprises determining the level of FX or GMD activity after delivering a shRNA nucleotide sequence to a host cell. In some embodiments, the level of FX or GMD activity is determined at the RNA level. In some embodiments, there is provided a method of determining a level of FX or GMD activity comprising determining the level of FX or GMD activity using PCR. In some embodiments, the level of FX or GMD activity is determined at a protein level. In some embodiments, there is provided a method of determining a level of FX or GMD activity comprising determining the FX or GMD activity level using immunohistochemistry. In some embodiments, there is provided a method of determining a level of FX or GMD activity comprising determining the FX or GMD activity level using Western blot. In some embodiments, there is provided a method of determining a level of FX or GMD activity comprising determining the FX or GMD activity level using flow cytometry. In some embodiments, the level of FX or GMD activity is determined by comparing a level of FX or GMD activity after delivery of a shRNA to a control value. In some embodiments, the level of FX or GMD activity is determined by comparing a level of FX or GMD activity after delivery of a shRNA to a wild type value. In some embodiments, the level of FX or GMD activity is determined by comparing a level of FX or GMD activity after delivery of a shRNA to a level of FX or GMD expression prior to delivery of a FX or GMD shRNA, respectively. In some embodiments, the FX or GMD activity level is based on an expression level of a FX or GMD gene, such as expression of FX or GMD RNA and/or protein. In some embodiments, the FX or GMD activity level is based on an expression level of a FX or GMD protein.

In some embodiments, the host cell further comprises an inactivated gene other than FX or GMD.

In general, host cells are transformed with a recombinant expression vector that comprises DNA encoding a desired protein. Additionally, the host cells of the present application can be a blank host cell. As used herein, "blank host" refers to a cell that does not contain an expression vector encoding a protein. In some embodiments, the blank host cell is a CHO cell. In some embodiments, the blank host cell is a mouse cell.

Also provided by the present application are host cells comprising nucleic acids encoding a protein described herein. Nucleic acid molecules provided by the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids provided herein are preferentially derived from human sources.

In certain embodiments, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or intrans, that are typically present in eukaryotic genes. Sequences of nontranslated DNA can be present 5' or 3' from an open reading frame, where the same do not interfere with manipulation or expression of the coding region.

In some embodiments, the host cell is capable of expressing a protein. In some embodiments, the host cell is capable of expressing a Fc-containing protein. In some embodiments, the host cell comprises a protein. In some embodiments, the host cell comprises a Fc-containing protein. In some embodiments, the host cell is capable of secreting a protein. In some embodiments, the host cell is capable of secreting a Fc-containing protein.

In some embodiments, the host cell is capable of expressing a protein at a similar output rate of the host cell prior to FX or GMD gene inactivation. In some embodiments, the host cell is capable of expressing a protein at the same output rate of the host cell prior to FX or GMD gene inactivation. In some embodiments, the host cell is capable of expressing a protein at about 70%, 75%, 80%, 85%, 90%, 95%, or 100% of the output rate of the host cell prior to FX or GMD gene inactivation.

In some embodiments, the host cell further comprises a gene modification. Optimization of a host cell for the purposes of producing a protein via gene modification is well known in the art and includes considerations pertaining to, for example, vector selection properties for integration methods and any other cellular property that would be desirable to manipulate for the production of a protein. In some embodiments, the gene modification is a targeted gene modification. In some embodiments, the gene modification is a knockout gene modification. In some embodiments, the gene modification is a knock-in gene modification.

Also provided are methods of evaluating a host cell for suitability of expression of proteins comprising determining FX or GMD activity, wherein a reduced level of FX or GMD activity is indicative of suitability.

Cells Engineered to Produce a Protein

The present application, in some aspects, provides a host cell engineered to produce a protein as described in the embodiments herein. The present application, in other aspects, provides methods for making a host cells as described in the embodiments herein.

In some embodiments, the host cell is engineered to produce a protein.

In some embodiments, there is provided a method for making a host cell engineered to produce a protein comprising: a) transforming the host cell with an expression vector comprising a nucleic acid encoding the protein.

Methods for transforming a host cell using an expression vector are well known in the art. See, for example. Kim et al., *Anal Bioanal Chem*, 397, 2010. Method for transfecting a host cell including, but are not limited to, transfection, infection, calcium phosphate co-precipitation, electroporation, microinjection, lipofection. DEAE-dextran mediated transfection, or other known techniques. The method selected will in part be a function of the type of host cell to be used. These methods and other suitable methods are well known to the skilled artisan.

Expression systems and constructs in the form of plasmids, expression vectors, transcription or expression cassettes which comprise at least one protein described herein are also provided. In certain embodiments, a plasmid, expression vector, transcription or expression cassette provided herein comprises a polynucleotide encoding at least one protein.

In some embodiments, expression vectors used in the host cells will contain sequences for plasmid maintenance and for cloning and expression of exogenous nucleotide sequences. Such sequences, collectively referred to as "flanking sequences," in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the protein to be expressed, and a selectable marker element. Each of these sequences is discussed below.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part expression vectors purchased commercially, and the origin aids in the amplification of the vector in a host cell. If the vector of choice does not contain an origin of replication site, one may be chemically synthesized based on a known sequence, and ligated into the vector. For example, various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thyrnidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody light or heavy chain. As a result, increased quantities of a polypeptide are synthesized from the amplified DNA.

A ribosome-binding site is usually necessary for translation initiation of mRNA and is characterized by, for example, a Kozak sequence. The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

Expression and cloning vectors of the invention will typically contain a promoter that is recognized by the host organism and operably linked to the molecule encoding the polypeptide. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding e.g., heavy chain or light chain, by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovinis (such as Adenovinis 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-310); CMV promoter (Thomsen et al., 1984, Proc. Natl. Acad. U.S.A. 81:659-663); the promoter contained in the 3' long terminal repeat of Rous sarcoma virus (Yamamoto et al., 1980, Cell 22:787-797); herpes thymidine kinase promoter (Wagner et al., 1981, Proc. Natl. Acad. Sci. U.S.A. 78:1444-1445); promoter and regulatory sequences from the metallothionine gene Prinster et al., 1982, Nature 296:39-42; or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Omitz et al., 1986, Cold Spring Harbor Symp. Quant. Biol. 50:399-409; MacDonald, 1987, Hepatology 7:425-515); the insulin gene control region that is active in pancreatic beta cells (Hanahan, 1985, Nature 315: 115-122); the immunoglobulin gene control region that is active in lymphoid cells (Grosschedl et al., 1984, Cell 38:647-658; Adames et al., 1985, Nature 318: 533-538; Alexander et al., 1987, Mol. Cell. Biol. 7:1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-feta-protein gene control region that is active in liver (Krumlauf et al., 1985, Mol. Cell. Biol. 5:1639-1648; Hammer et al., 1987, Science 253:53-58); the alpha 1-antitrypsin gene control region that is active in liver (Kelsey et al., 1987, Genes and Devel. 1: 161-171); the beta-globin gene control region that is active in myeloid cells (Mogram et al., 1985, Nature 315:338-340; Kollias et al., 1986, Cell 46:89-94); the myelin basic protein gene control region that is active in oligodendrocyte cells in the brain (Readhead et al., 1987, Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234: 1372-1378).

An enhancer sequence may be inserted into the vector to increase transcription of DNA encoding light chain or heavy chain of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alphafeto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-I receptor signal peptide described in U.S. Pat. No. 4,968,607; the type II interleukin-I receptor signal peptide described in EP Patent No. 0 460 846.

The vector may contain one or more elements that facilitate expression when the vector is integrated into the host cell genome. Examples include an EASE element (Aldrich et al. 2003 Biotechnol Prog. 19: 1433-38) and a matrix attachment region (MAR). MARs mediate structural organization of the chromatin and may insulate the integrated vector from "position" effect. Thus, MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

Expression vectors provided by the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding a protein sequence has been inserted into the proper site of the vector, the completed vector may be inserted into a suitable host cell for amplification and/or polypeptide expression.

Methods for making a vector comprising a nucleic acid encoding a protein, such as an Fc-containing protein, are well known in the art. See, e.g., U.S. Pat. No. 7,923,221.

Construction of suitable vectors comprising a protein and the desired coding and control sequences employ standard ligation techniques. Isolated plasmids or DNA fragments are cleaved, tailored, and religated in the form desired to form the plasmids required. The methods employed are not dependent on the DNA source, or intended host.

In some embodiments, there is provided a method of making a protein further comprising determining an optimal ratio of the polynucleotide for introduction into a host cell. In some embodiments, mass spectrometry is used to determine protein yield, and the ratio is adjusted to maximize protein yield. In some embodiments, dual antigen ELISA is used to determine protein yield, such as a Fc-containing protein, and the ratio is adjusted to maximize protein yield.

Purification

Methods described herein, in some aspects, further comprise methods for isolating a protein produced by the methods described herein.

Methods for obtaining a protein are well known in the art. See, e.g., Huse et al., *J Biochem Bioph Meth,* 51, 2002. Proteins can be produced intracellularly or directly secreted into the medium. If the proteins are produced intracellularly, as a first step, the particulate debris, either host cells or lysed fragments, are removed, for example, by centrifugation or ultrafiltration. If the proteins are secreted into the medium, supernatants from such expression systems are generally first concentrated using a commercially available protein concentration filter, for example, an Amicon or Millipore Pellicon ultrafiltration unit. In some embodiments, a protease inhibitor may be included in any of the foregoing steps to inhibit proteolysis and antibiotics may be included to prevent the growth of adventitious contaminants.

The composition prepared from the cells can be purified using, for example, hydroxylapatite chromatography, gel electrophoresis, dialysis, and affinity chromatography, with affinity chromatography being the preferred purification technique. For Fc-containing proteins, the suitability of protein A as an affinity ligand depends on the species and isotype of any immunoglobulin Fc domain that is present in the Fc-containing protein. Protein A can be used to purify Fc-containing proteins that are based on human immunoglobulins containing 1, 2, or 4 heavy chains (See, e.g., Lindmark et al., *J Immunol Meth,* 62, 1983). Protein G is recommended for all mouse isotypes and for human 3 (See, e.g., Guss et al., *EMBO,* 5, 1986). The matrix to which the affinity ligand is attached is often agarose, but other matrices are available. Mechanically stable matrices such as controlled pore glass or poly(styrene-divinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

In some embodiments, there is provided a method of purifying a protein comprising using a filter. In some embodiments, the filter is a diafiltration system. In some embodiments, the filter is an ultrafiltration system. In some embodiments, the filter is a viral filtration system. In some embodiments, the purifying a protein comprises using a series of filtration steps. In some embodiments, the series of filtration steps is selected from at least one of the following: diafiltration, ultrafiltration, and viral filtration.

In some embodiments, there is provided a method of purifying a protein comprising using a series of protein purification techniques selected from filtration, protein A purification, cation exchange purification, strong cation exchange purification, anion exchange purification, reverse phase purification, and multimodal purification.

Compositions

The present application, in some aspects, provides a protein comprising a glycan structure, wherein the protein is in a predetermined ratio of fucosylated and afucosylated forms of the protein, produced by any of the methods disclosed herein.

In some embodiments, the protein is a Fc-containing protein. In some embodiments, the Fc-containing protein comprises a Fc domain. In some embodiments, the Fc-containing protein comprises one or more Fc domains. In some embodiments, the Fc-containing protein comprises two Fc domains.

In some embodiments, the Fc-containing protein comprises a heavy chain or a fragment thereof. In some embodiments, the Fc-containing protein comprises at least one heavy chain. In some embodiments, the Fc-containing protein comprises one or more heavy chains. In some embodiments, the Fc-containing protein comprises two heavy chains.

In some embodiments, the Fc-containing protein is a full length antibody. In some embodiments, the full length antibody is a human antibody. In some embodiments, the full length antibody is a humanized antibody. In some embodiments, the full length antibody is a monoclonal antibody. In some embodiments, the full length antibody is a chimeric antibody. In some embodiments, the full length antibody is a bispecific antibody. In some embodiments, the full length antibody is a multispecific antibody.

In some embodiments, the Fc-containing protein is a Fc-containing fusion protein. In some embodiments, the Fc-containing fusion protein comprises one or more Fc domains.

In some embodiments, the Fc domain of the Fc-containing fusion protein prolongs a plasma half-life of the Fc-containing fusion protein. In some embodiments, the Fc domain of the Fc-containing fusion protein prolongs the biological activity of the Fc-containing fusion protein. In some embodiments, the Fc domain of the Fc-containing fusion protein decreases the rate of renal clearance of the Fc-containing fusion protein. In some embodiments, the Fc domain of the Fc-containing fusion protein increases the solubility of the Fc-containing fusion protein. In some embodiments, the Fc domain of the Fc-containing fusion protein increases the stability of the Fc-containing fusion protein.

Fc-containing fusion proteins are well known in the art. See, e.g., Czajkowsky et al., EMBO Mol Med, 4, 2012, 1015-1028. In some embodiments, the Fc-containing fusion protein is an immunoadhesin. In some embodiments, the Fc-containing fusion protein is a cytokine-Fc fusion protein.

In some embodiments, the protein is a multimeric protein. In some embodiments, the Fc-containing protein is a multimeric protein. In some embodiments, the Fc-containing fusion protein is a multimeric protein.

In some embodiments, the protein is conjugated to an agent. In some embodiments, the protein is conjugated to at least about 2, 3, 4, 5, 6, 7, 8, 9, or 10 molecules of an agent. In some embodiments, the protein is conjugated to about 2-10, about 4-10, about 6-10, or about 8-10 molecules of an agent. In some embodiments, the Fc-containing protein is conjugated to an agent, wherein the agent is conjugated to the Fc domain of the Fc-containing protein. In some embodiments, the agent is a therapeutic agent. In some embodiments, the therapeutic agent is a small molecule therapeutic agent. In some embodiments, the therapeutic agent is a chemotherapeutic agent. In some embodiments, the agent is a detection agent. In some embodiments, the detection agent is a radiolabel. In some embodiments, the detection agent is a fluorescent label. In some embodiments, the detection agent is an immunolabel. In some embodiments, the protein is a companion diagnostic. In some embodiments, the Fc-containing protein is a companion diagnostic.

In some embodiments, the protein comprises a post-translational modification. In some embodiments, the post-translational modification is non-enzymatically produced. In some embodiments, the post-translational modification is enzymatically produced. In some embodiments, the post-translational modification is selected from the group consisting of a disulfide pairing, a deamidation, an oxidation, and a N-terminal glutamine cyclization.

In some embodiments, the protein, such as an Fc-containing protein, may bind to, or interact with, any protein, including, without limitation, a member of the HER receptor family, such as HER1 (EGFR), HER2, HER3 and HER4; CD proteins such as CD3, CD4, CD8, CD19, CD20, CD21, CD22, and CD34; cell adhesion molecules such as LFA-1, Mo1, p150,95, VLA-4, ICAM-1, VCAM and αv/p3 integrin including either α or β or subunits thereof (e.g. anti-CD11a, anti-CD18 or anti-CD11b antibodies); macrophage receptor such as CRIg, tumor necrosis factors such as TRAIL/Apo-2, growth factors such as vascular endothelial growth factor (VEGF); IgE; blood group antigens; flk2/flt3 receptor; obesity (OB) receptor; and protein C. Other exemplary proteins include growth hormone (GH), including human growth hormone (hGH) and bovine growth hormone (bGH); growth hormone releasing factor; parathyroid hormone; thyroid stimulating hormone; lipoproteins; α-1-antitrypsin; insulin A-chain; insulin B-chain; proinsulin; follicle stimulating hormone; calcitonin; luteinizing hormone; glucagon; clotting factors such as factor VIIIC, tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; tumor necrosis factor-α and -β; enkephalinase; RANTES (regulated on activation normally T-cell expressed and secreted); human macrophage inflammatory protein (MIP-1-α); serum albumin such as human serum albumin (HSA); mullerian-inhibiting substance; relaxin A-chain; relaxin B-chain; prorelaxin; mouse gonadotropin-associated peptide; DNase; inhibin; activin; receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins (IGFBPs); erythropoietin (EPO); thrombopoietin (TPO); osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor (DAF); a viral antigen such as, for example, a portion of the AIDS envelope; transport proteins; homing receptors; addressins; regulatory proteins; immunoadhesins; antibodies; and biologically active fragments or variants of any of the above-listed polypeptides. Many other antibodies and/or other proteins may be used in accordance with the instant invention, and the above lists are not meant to be limiting.

The present application, in some aspects, provides compositions comprising a protein made by any of the methods described herein. The present application, in another aspect, provides composition comprising a protein having an enhanced ADCC function mediated by NK cells and PMN cells, wherein the composition comprises afucosylated and fucosylated forms of the protein at a ratio that provides the enhanced ADCC function.

In some embodiments, the fucosylated form of the protein comprises fucose at the reducing end of a glycan structure. In some embodiments, the fucosylated form of the protein comprises fucose at the reducing end of a glycan structure, wherein the fucose is covalently attached to a first N-acetylglucosamine (GlcNAc) moiety of the reducing end of the glycan structure. In some embodiments, the glycan structure comprises a fucose moiety at the reducing end of the glycan structure. In some embodiments, the fucose moiety is a single fucose molecule covalently bound to the glycan structure. In some embodiments, the glycan structure comprises an L-fucose. In some embodiments, the protein, comprises two or more glycan structures.

In some embodiments, the composition is a pharmaceutical composition. In some embodiments, the pharmaceutical composition is in a form for storage. In some embodiments, the pharmaceutical composition is in a form for product transportation. In some embodiments, the pharmaceutical composition is frozen. In some embodiments, the pharmaceutical composition is lyophilized. In some embodiments, the pharmaceutical composition is reconstituted. In some embodiments, the pharmaceutical composition is an administration composition. In some embodiments, the pharmaceutical composition is in a form for administration to an individual in need thereof.

In some embodiments, the pharmaceutical composition is a sterile pharmaceutical composition. Sterile pharmaceutical formulations are compounded or manufactured according to pharmaceutical-grade sterilization standards (e.g., United States Pharmacopeia Chapters 797, 1072, and 1211; California Business & Professions Code 4127.7; 16 California Code of Regulations 1751, 21 Code of Federal Regulations 21, or ex-U.S. counterparts to such regulations) known to those of skill in the art.

In some embodiments, the pharmaceutical composition is a stable formulation. As used herein, "stable" formulation is one in which the proteins therein essentially retain physical and chemical stability and integrity upon storage. Various analytical techniques for measuring protein stability are available in the art and are reviewed in, for example, Jones, *Adv Drug Delivery Rev,* 10, 1993. Stability can be assessed at a selected temperature for a selected time period. For example, the extent of aggregation during storage can be used as an indicator of protein stability. Thus, a "stable" formulation may be one wherein less than about 10% and preferably less than about 5% of the protein are present as an aggregate in the formulation.

In some embodiments, the pharmaceutical composition is a reconstituted formulation. As used herein, a "reconstituted" formulation is one which has been prepared by dissolving a lyophilized protein formulation in a diluent such that the protein is dispersed throughout. The reconstituted formulation is suitable for administration (e.g. intravenous or subcutaneous administration) to an individual in need there.

In some embodiments, the pharmaceutical composition is an isotonic formulation. As used herein, an "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood.

In some embodiments, the pharmaceutical composition is at a specified pH. In some embodiments, the pharmaceutical composition is at a pH of about 5-7, about 5-6, or about 5-5.5. In some embodiments, the pharmaceutical composition is at a pH of about 5.3. In some embodiments, the pharmaceutical composition is at a pH of about 5.4. In some embodiments, the pharmaceutical composition is pH adjusted.

In some embodiments, the pharmaceutical composition further comprises a pharmaceutically acceptable carrier. As used herein, a "pharmaceutically acceptable carrier" refers to an ingredient in a pharmaceutical composition, other than an active ingredient. A pharmaceutically acceptable carrier includes, but is not limited to, a buffer, excipient, stabilizer, or preservative. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). In some embodiments, the pharmaceutically acceptable carrier is selected from the group consisting of sodium acetate, sucrose, polysorbate (e.g., polysorbate 20), sodium succinate, histidine HCl, and sodium chloride.

In some embodiments, the pharmaceutical composition further comprises a pharmaceutically acceptable acid. As used herein, a "pharmaceutically acceptable acid" includes inorganic and organic acids which are non-toxic at the concentration and manner in which they are formulated. For example, suitable inorganic acids include hydrochloric, perchloric, hydrobromic, hydroiodic, nitric, sulfuric, sulfonic, sulfinic, sulfanilic, phosphoric, carbonic, etc. Suitable organic acids include straight and branched-chain alkyl, aromatic, cyclic, cycloaliphatic, arylaliphatic, heterocyclic, saturated, unsaturated, mono, di- and tri-carboxylic, including for example, formic, acetic, 2-hydroxyacetic, trifluoroacetic, phenylacetic, trimethylacetic, t-butyl acetic, anthranilic, propanoic, 2-hydroxypropanoic, 2-oxopropanoic, propandioic, cyclopentanepropionic, cyclopentane propionic, 3-phenylpropionic, butanoic, butandioic, benzoic, 3-(4-hydroxybenzoyl)benzoic, 2-acetoxy-benzoic, ascorbic, cinnamic, lauryl sulfuric, stearic, muconic, mandelic, succinic, embonic, fumaric, malic, maleic, hydroxymaleic, malonic, lactic, citric, tartaric, glycolic, glyconic, gluconic, pyruvic, glyoxalic, oxalic, mesylic, succinic, salicylic, phthalic, palmoic, palmeic, thiocyanic, methanesulphonic, ethanesulphonic, 1,2-ethanedisulfonic, 2-hydroxyethanesulfonic, benzenesulphonic, 4-chorobenzenesulfonic, napthalene-2-sulphonic, p-toluenesulphonic, camphorsulphonic, 4-methylbicyclo [2,2,2]-oct-2-ene-1-carboxylic, glucoheptonic, 4,4'-methylenebis-3-(hydroxy-2-ene-1-carboxylic acid), hydroxynapthoic.

In some embodiments, the pharmaceutical composition further comprises a pharmaceutically acceptable base. As used herein, a "pharmaceutically acceptable base" includes inorganic and organic bases which are non-toxic at the concentration and manner in which they are formulated. For example, suitable bases include those formed from inorganic base forming metals such as lithium, sodium, potassium, magnesium, calcium, ammonium, iron, zinc, copper, manganese, aluminum, N-methylglucamine, morpholine, piperidine and organic nontoxic bases including, primary, secondary and tertiary amines, substituted amines, cyclic amines and basic ion exchange resins, for example, isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Additional pharmaceutically acceptable acids and bases useable with the present invention include those which are derived from the amino acids, for example, histidine, glycine, phenylalanine, aspartic acid, glutamic acid, lysine and asparagine.

In some embodiments, the pharmaceutical composition further comprises a pharmaceutically acceptable buffer or salt, for example, those derived from both acid and base addition salts of the above indicated acids and bases. Specific buffers and/or salts include histidine, succinate and acetate.

In some embodiments, the pharmaceutical composition further comprises a pharmaceutically acceptable sugar. As used herein, a "pharmaceutically acceptable sugar" is a molecule which, when combined with a protein, significantly prevents or reduces chemical and/or physical instability of the protein upon storage. When the formulation is intended to be lyophilized and then reconstituted, "pharmaceutically acceptable sugars" may also be known as a "lyoprotectant". Exemplary sugars and their corresponding sugar alcohols include: an amino acid such as monosodium glutamate or histidine; a methylamine such as betaine; a lyotropic salt such as magnesium sulfate; a polyol such as trihydric or higher molecular weight sugar alcohols, e.g. glycerin, dextran, erythritol, glycerol, arabitol, xylitol, sorbitol, and mannitol; propylene glycol; polyethylene glycol; PLURONICS®; and combinations thereof. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Preferred sugar alcohols are monoglycosides, especially those compounds obtained by reduction of disaccharides such as lactose, maltose, lactulose and maltulose. The glycosidic side group can be either glucosidic or galactosidic. Additional examples of sugar alcohols are glucitol, maltitol, lactitol and iso-maltulose. The preferred pharmaceutically-acceptable sugars are the non-reducing sugars trehalose or sucrose. Pharmaceutically acceptable sugars are added to the formulation in a "protecting amount" (e.g. pre-lyophilization) which means that the protein essentially retains its physical and chemical stability and integrity during storage (e.g., after reconstitution and storage).

In some embodiments, the pharmaceutical composition further comprises a pharmaceutically acceptable preservative. As used herein, a "pharmaceutically acceptable preservative" is a compound which can be added to the formulations herein to reduce bacterial activity. Examples of potential preservatives include, but are not limited to, octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

In some embodiments, the composition comprising a plurality of proteins is a cell culture medium. In some embodiments, the cell culture medium is a nutrient media. Nutrient media contains all elements needed for host cell growth. In some embodiments, the cell culture medium is a minimal medium. Minimal media contains the minimum nutrients possible for host cell growth, for example, generally without the presence of amino acids. In some embodiments, the cell culture medium is a selective medium. Selective media comprises an agent that inhibits growth of a select organism.

In some embodiments, the cell culture medium further comprises a cell culture medium nutrient for cell support and/or growth. In some embodiments, the cell culture medium nutrient is selected from, for example: proteins; peptides; amino acids; carbohydrates; metals and minerals, for example calcium, magnesium, iron; trace metals, for example, phosphates and sulphates; buffers; pH indicators, for example, phenol red, bromo-cresol purple; and antimicrobial agents.

In some embodiments, the cell culture medium further comprises a host cell. In some embodiment, the culture medium is substantially devoid of a host cell.

In some embodiments, the cell culture medium comprises a fucose source. In some embodiments, the fucose source is a fucose. In some embodiments, the fucose is L-fucose. In some embodiments, the fucose is L-fucose-1-phosphate. In some embodiments, the fucose source is GDP-fucose.

In some embodiments, the composition is a cell lysate. In some embodiments, the cell lysate comprises a plurality of proteins and host cell components. In some embodiments, the cell lysate is a centrifuged cell lysate. In some embodiments, the cell lysate comprises a precipitated portion of the cell lysate and a supernatant portion of the cell lysate. In some embodiments, the cell lysate comprises a pelleted portion of the cell lysate and a supernatant portion of the cell lysate.

In some embodiments, the composition is an eluate from a protein purification column. As used herein, "eluate" refers to any fluid that passes through a protein purification column. In some embodiments, the eluate comprises a fluid that is isolated from a flow-through fluid. In some embodiments, the eluate comprises a fluid that is isolated from a wash fluid. In some embodiments, the eluate comprises a fluid that is isolated from one or more wash fluids. In some embodiments, the eluate comprises a fluid that is isolated from an elution fluid.

In some embodiments, the composition is a library of proteins, wherein at least two of the proteins of the plurality of proteins are different. In some embodiments, the library comprises at least two proteins that bind to different antigens. In some embodiments, the library comprises at least two proteins that hind to different epitopes. In some embodiments, the different proteins are contained in different vessels. In some embodiments, the present invention provides libraries comprising at least 2, 3, 4, 5, 10, 30, 100, 250, 500, 750, 1000, 2500, 5000, 7500, 10000, 25000, 50000, 75000, 100000, 250000, 500000, 750000, 1000000, 2500000, 5000000, 7500000, 10000000, or more than 10000000 different proteins.

The present application provides large-scale batches (e.g., commercial batches or batches at manufacture scale) of any of the compositions described in the embodiments herein. For example, in some embodiments, the hatch comprises fucosylated and afucosylated forms of a protein at a predetermined ratio. In some embodiments, the batch comprises a protein with an enhanced ADCC function mediated both by NK cells and PMN cells. In some embodiments, the batch comprises fucosylated and afucosylated forms of an antibody at a predetermined ratio. In some embodiments, the batch comprises an antibody with an enhanced ADCC function mediated both by NK cells and PMN cells.

In some embodiments, the batch comprises at least about 5 g, 10 g, 50 g, 100 g, 200 g, 300 g, 400 g, 500 g, 600 g, 700 g, 800 g, 900 g, 1,000 g, 1,500 g, 2,000 g, 2,500 g, 3,000 g, 3,500 g, 4,000 g, 4,500 g, or 5,000 g of a protein, wherein the fucosylated and afucosylated forms of the protein are at a predetermined ratio. In some embodiments, the batch comprises at least about 5-5,000 g, 50-4,000 g, or about 100-1,000 g of a protein, wherein the fucosylated and afucosylated forms of the protein are at a predetermined ratio.

In some embodiments, the batch is in a form for drug storage. In some embodiments, the batch is in a form for product transportation. In some embodiments, the batch is in a form for administration to an individual in need thereof. In some embodiments, the batch is lyophilized. In some embodiments, the batch is not conjugated to an agent. In some embodiments, the batch is conjugated to an agent. In some embodiments, the batch further comprises a formulation component.

In some embodiments, the batch is a cell culture medium. In some embodiments the batch is a cell lysate.

In some embodiments, the batch, or a portion thereof, is in a vessel. In some embodiments, the batch, or portion thereof, is in a vial. In some embodiments, the batch, or portion thereof, is in a plurality of vials. In some embodiments, the batch, or portion thereof, is in a syringe.

In some embodiments, the hatch, or a portion thereof, is in a plurality of vials, wherein each vial comprises a protein, wherein the fucosylated and afucosylated forms of the protein are at a predetermined ratio. In some embodiments, the batch, or a portion thereof, is in a plurality of vials, wherein at least about 50%, 55%, 60%, 65%, 70%, 75%, 80%, 85%, 90%, 95%, or 100% of the vials comprise fucosylated and afucosylated forms of a protein are at a predetermined ratio.

In some embodiments, the batch is aliquoted into a unit dosage. As used herein, a "unit dosage" is the amount of protein intended for administration as a single unit dose. In some embodiments, the single unit dose is about 1 to about 500 mg of a protein. In some embodiments, the unit dosage is packaged in a container. In some embodiments, the unit dosage is packaged in a vial.

In some embodiments, the size of the commercial batch is no greater than about 1, 2, 3, 4, 5, 6, 7, 8, 9, or 10 times the size of the clinical batch. As used herein, "commercial batch" refers to an amount of protein produced during one or more production runs completed for purposes of commercial production and/or distribution. As used herein, "clinical batch" refers to an amount of protein produced during one or more production runs completed for purposes of clinical testing. In some embodiments, the size of the commercial batch is no greater than 10 times the size of the clinical batch.

In some embodiments, the vessel comprises an aliquot of a commercial batch as described herein, wherein the commercial batch comprises a composition comprising a protein, wherein the fucosylated and afucosylated forms of the protein are at a predetermined ratio. In some embodiments, the vial comprises an aliquot of a commercial batch as described herein, wherein the commercial batch comprises a composition comprising a protein, wherein the fucosylated and afucosylated forms of the protein are at a predetermined ratio. In some embodiments, the syringe comprises an aliquot of a commercial batch as described herein, wherein the commercial batch comprises a composition comprising a protein, wherein the fucosylated and afucosylated forms of the protein are at a predetermined ratio.

Methods of Treatment

The present application provides, in some aspects, methods of treating a disease in an individual in need thereof comprising administering to the individual a pharmaceutical composition described in the embodiments herein.

In some embodiments, the effective amount of a pharmaceutical composition is administered to an individual in need thereof, wherein the pharmaceutical composition comprises afucosylated and fucosylated forms of a protein in a predetermined ratio.

In some embodiments, the effective amount of a pharmaceutical composition is administered to an individual in need thereof, wherein the pharmaceutical composition comprises a protein having an enhance ADCC function mediated both by NK cells and PMN cells. In some embodiments, the effective amount of a pharmaceutical composition is administered to an individual in need thereof, wherein the pharmaceutical composition comprises a protein having an enhance ADCC function mediated both by NK cells and PMN cells, wherein the pharmaceutical composition comprises afucosylated and fucosylated forms of the protein at a ratio that provides the enhanced ADCC function.

The pharmaceutical composition described herein can be administered via various routes, such as parenterally, including intravenous, intra-arterial, intraperitoneal, intrapulmonary, oral, inhalation, intravesicular, intramuscular, intratracheal, subcutaneous, intraocular, intrathecal, or transdermal. In some embodiments, pharmaceutical composition described herein can be administered parenterally. In some embodiments, pharmaceutical composition described herein can be administered intravenously. In some embodiments, pharmaceutical composition described herein can be administered subcutaneously. In some embodiments, pharmaceutical composition described herein can be administered locally. In some embodiments, pharmaceutical composition described herein can be administered topically.

The diseases that can be treated by the methods herein are any disease that can be treated with a protein. In some embodiments, the disease a cancer. In some embodiments, the disease is an autoimmune disease. In some embodiments, the disease is an infection.

In some embodiments, the pharmaceutical composition described herein is used in combination with another administration modality or treatment.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1

Development of FX Knockout CHO Cell Lines Each Capable of Expressing an Antibody with a Fucosylation: Afucosylation Ratio that can be Adjusted by Fucose Titration To assess the changes in biological function of an afucosylated form of an antibody, it is necessary to produce both the wild type (fucosylated) and afucosylated forms of the antibody. Previously, FUT8 knockout hosts (FUT8-KO) have been used to develop CHO cell lines capable of expressing the afucosylated form of an antibody with relatively reasonable titers (Malphettes et al., *Biotechnol Bioeng*, 106, 2010, 774-783). However, FUT8-KO cell lines have been observed to have slower growth and adaptation rates of clones. Furthermore, to also produce the antibody in a wild type form (i.e., a fucosylated form) requires an additional and separate cell line development (CLD). To accomplish this, it is necessary to produce and screen large numbers of clones, a daunting and cumbersome task, to obtain clones that produce wild type and afucosylated forms of the antibody with matching product qualities. Even more challenging is obtaining wild type and FUT8-KO clones that produce antibodies with similar enough product quality attributes to ensure that any observed difference with the wild type and afucosylated form of the antibody can be strictly attributed to afucosylation.

A single cell line capable of producing the wild type and afucosylated form of the antibody would allow for the production of an antibody with the same product quality attributes. Here, it was hypothesized that by inactivating the de novo pathway and controlling the level of fucose it may be possible to produce a cell line capable of producing wild type fucosylated and afucosylated forms of an antibody. Generation and characterization of a GMD knockout CHO host line has been previously reported, however, the achieved specific productivities (Qp) were low, about 16 pg/cell-d (Kanda et al., *J Biotechnol*, 130, 2007, 300-310). Here, we explore knocking out the FX gene in our CHO-K1 host line via CRISPR/Cas9 system and evaluate growth, expression, and fucosylation status of antibodies in such host(s).

Results:
Targeting FX Locus Using a CRISPR/Cas9 System

Figure 2A:
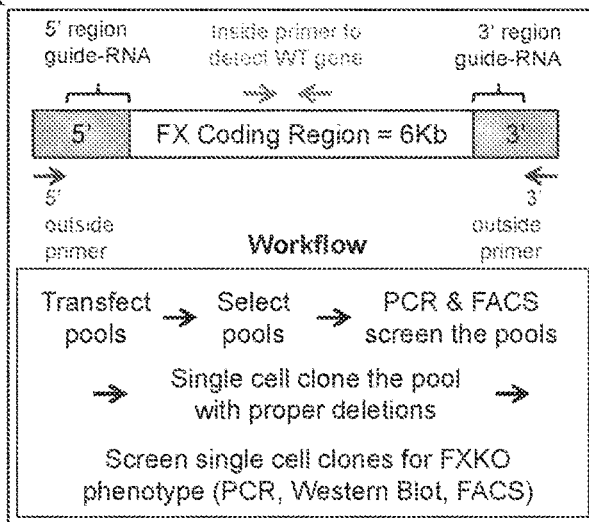
FIGS. 2A-2B show a workflow for inactivating FX and the PCR analysis of cells with an inactivated FX gene.

To target the FX locus, the 5' and 3' coding regions of the CHO-K1 FX gene was sequenced. Using the sequence, guide-RNA (gRNA) constructs that were complementary to the sequence were designed for use with a CRISPR/Cas system (Le Cong et al., *Science*, 339, 2013, 819-823; Mali et al., *Nat Methods*, 10, 2013, 957-963). gRNA sequences were designed flanking the 5' and 3' regions of the FX gene and were co-transfected along with a Cas9 expressing vector at an equimolar ratio to delete the entire 6 Kb FX gene. Individual gRNAs were cloned and expressed under the control of the human U6 promoter of the pLKO.5 vector (Cat #SHC-201, Sigma). Seventy-two hours after transfection, pools of transfected cells were selected in media containing 200 μg/ml LCA (to select out cells with fucosylated surface glycoproteins). QIAGEN Blood and Tissue Extraction Kit (Cat #69506) and Roche HiFi Taq Polymerase (Cat #11732650001) were used for DNA extraction and PCR analysis, respectively. External and internal PCR primers relative to the gRNAs were designed to distinguish between alleles with complete FX deletion versus those with wild type or small-deletions, respectively (FIG. 2A). CHO-K1 cells were transfected with gRNA and Cas9 expressing vectors and selected as pools in presence of lens culinaris agglutinin (LCA). Fluorescein (FITC) conjugated LCA (LCA-FITC) reagent was used to confirm reduction of fucosylated glycoprotein on the cell surface by a flow sorter.

Figure 2B:
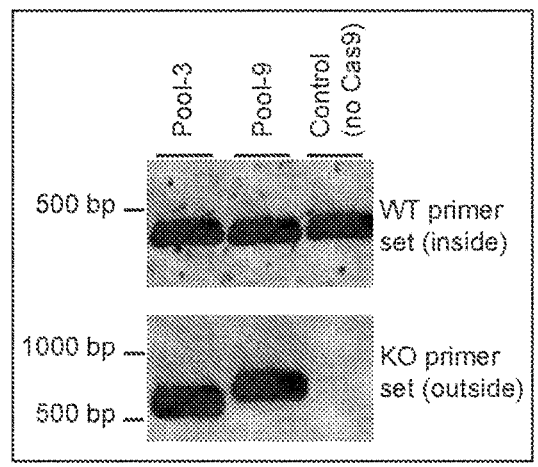

FX gene deletion was confirmed via PCR analysis (FIG. 2B). Primers internal to the gRNAs were used to detect wild type alleles or alleles with small deletions, while the external primers were used to detect alleles with full deletion of FX gene.

Figure 3:
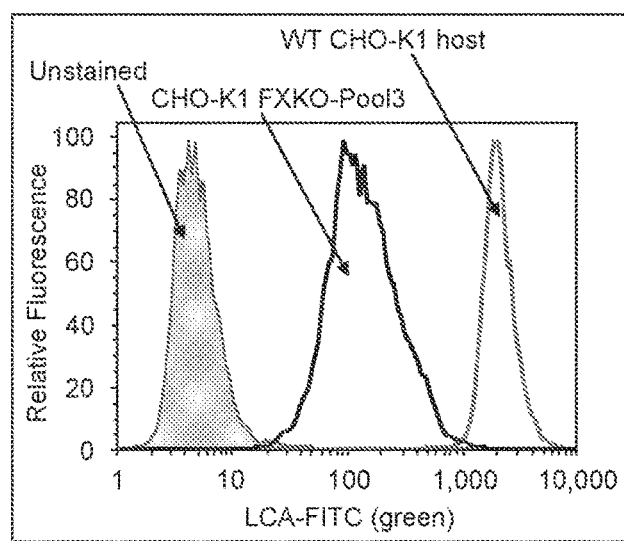
FIG. 3 shows FACS analysis of unstained CHO-K1 cells (unstained), LCA-FITC stained CHO-K1 cells with FX inactivation (CHO-K1 FXKO-Pool-3), and LCA-FITC stained wild type CHO-K1 cells (WT CHO-K1 host).

Pools with FX deletion were single cell cloned via limited dilution and screened by PCR, fluorescence-activated cell sorting (FACS), and western blot for deletion of FX gene. Flow cytometer analysis of FXKO Pool-3, stained with LCA-FITC, confirmed the absence/reduction in levels of fucosylated glycolproteins at the cell surface (FIG. 3).

Isolating Single Cell Clones and Confirming FX Gene Knockout

Figure 4A:
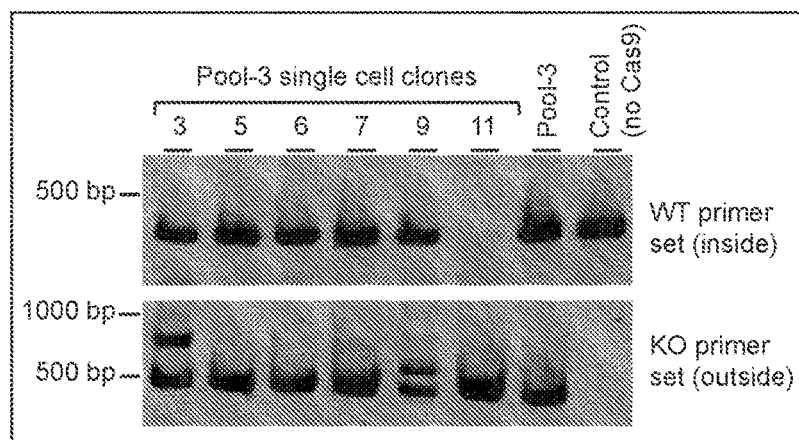
FIGS. 4A-4B show FX gene and protein analysis of single cell clones obtained from Pool-3.
Figure 4B:
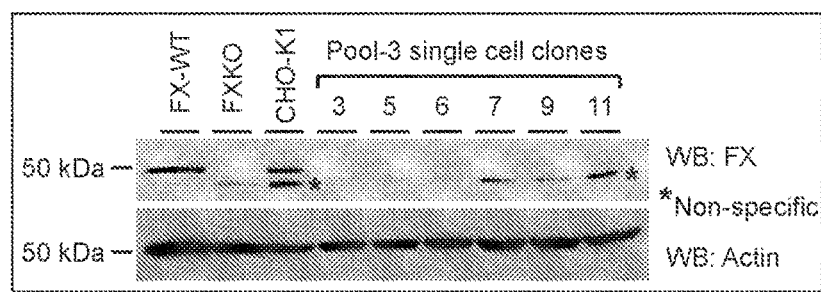
Figure 5A:
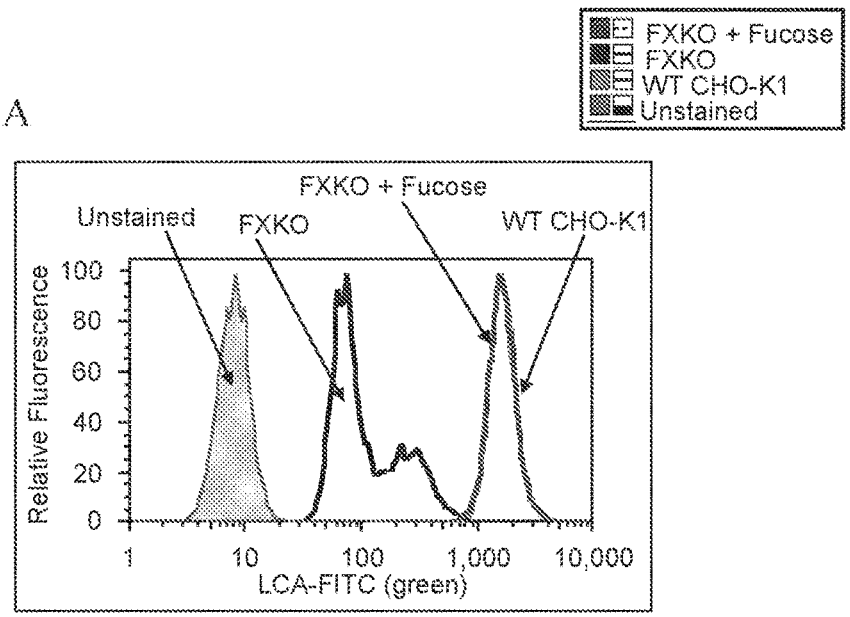
FIGS. 5A-5F show FACS analysis of single cell clones obtained from Pool-3. Each FACS analysis shows unstained CHO-K1 cells (unstained), LCA-FITC stained CHO-K1 cells with FX inactivation grown in media comprising fucose (FXKO+Fucose), LCA-FITC stained CHO-K1 cells with FX inactivation grown in media lacking fucose (FXKO), and LCA-FITC stained wild type CHO-K1 cells (WT CHO-K1).
Figure 5B:
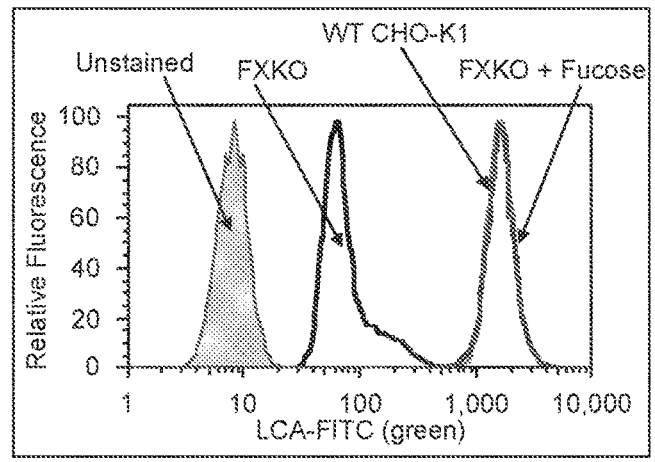
Figure 5C:
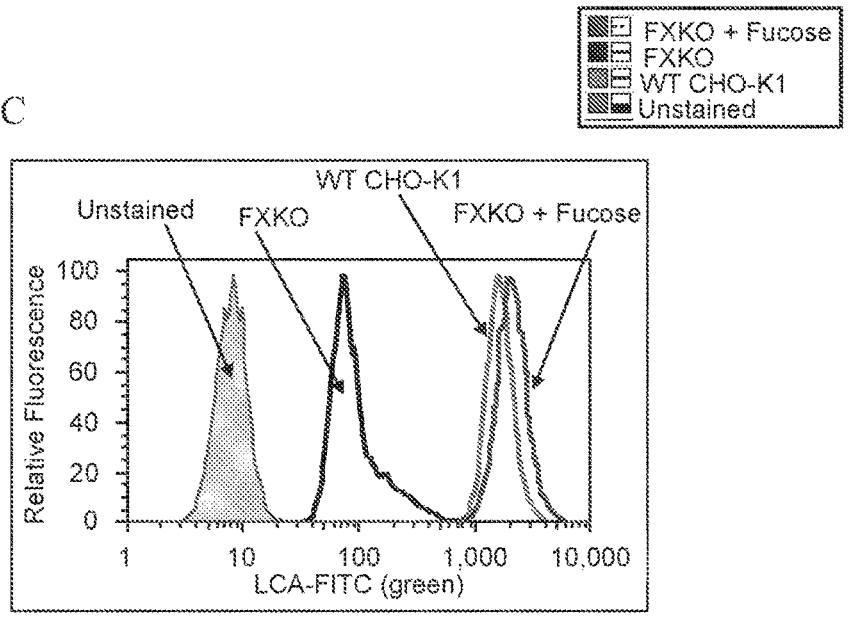
Figure 5D:
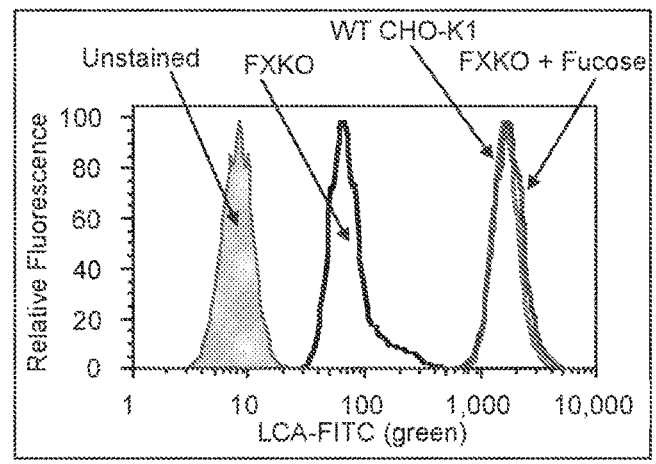
Figure 5E:
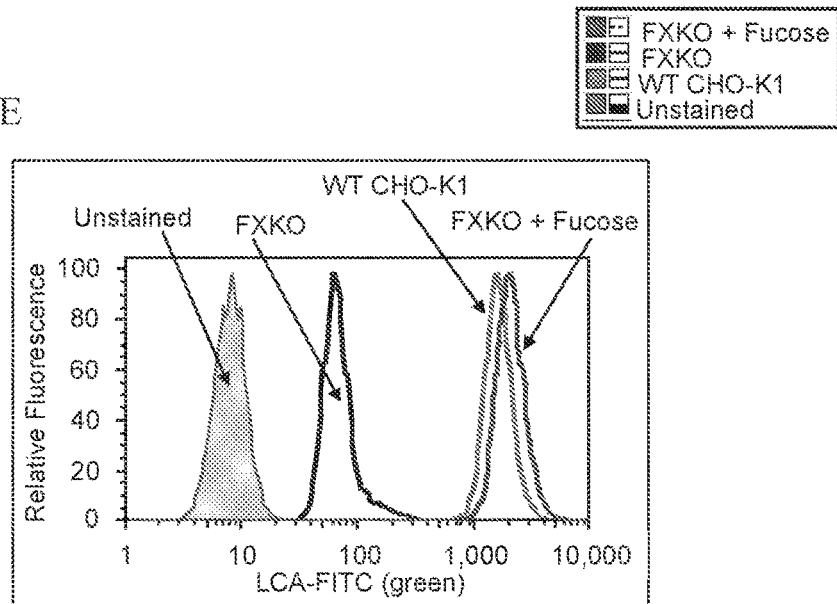
Figure 5F:
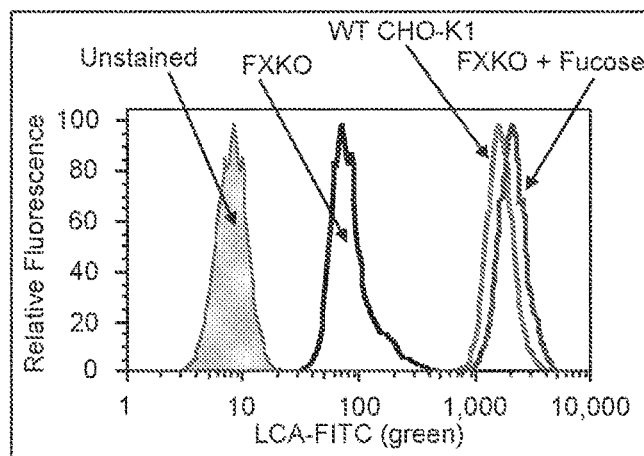

To obtain single clones where FX gene is knocked out in all alleles, cells from Pool-3 were single cell cloned by limited dilution and screened by PCR for deletions in FX gene (FIG. 4A). Among clones screened, 5 clones possessed at least one deleted and one wild type allele, and one clone (clone-11) displayed complete FX deletion in all of its alleles (FIG. 4A). Note that while presence of the PCR product(s) detected by the KO primer set is indicative of the FX gene deletion, presence of a PCR band amplified by the wild type primer set does not necessarily imply that the FX gene is capable of expressing a functional protein (FIG. 2A and FIG. 4A). The screening approach designed for the wild type primers does not discriminate against point mutations and small deletions, which may result in expression of a nonfunctional or truncated FX protein, or even deficiency in FX protein expression all together. To confirm lack of FX protein expression, the top 6 clones were analyzed by immunoblotting assay and confirmed that all of clones lacked FX protein expression (FIG. 4B). This suggesting that the FX gene is knocked out either via complete allele deletion or a combination of deletion and frame shift. LCA-FITC staining and flow cytometry was also used to confirm that depending on the absence or presence of fucose in the media, these clones are capable of expressing afucosylated or fucosylated glycoproteins, respectively (FIGS. 5A-5F).

Evaluating FXKO Clones to Express Wild Type or Afucosylated Antibodies

Figure 6A:
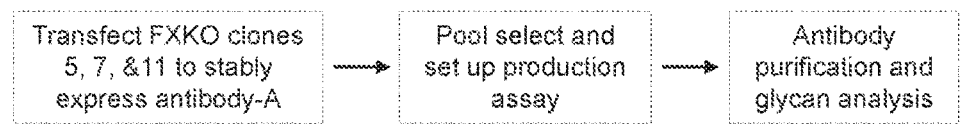
Figure 6B:
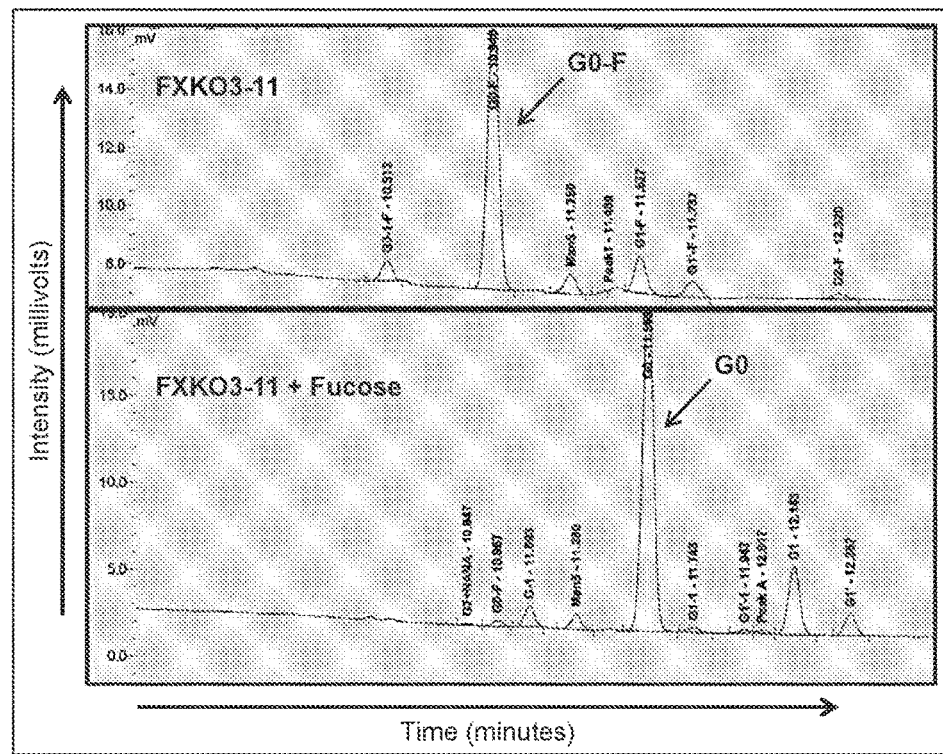

FXKO hosts 3-5, 3-7, and 3-11 were chosen based on growth and viability profiles for further evaluation, specifically to ensure that they are capable of expressing afucosylated antibodies. To this end, these FXKO hosts were transfected with a construct expressing antibody-A and pool selected for 3 weeks (FIG. 6A). Parental CHO-K1 host was used as control and antibody expression for all the pools were confirmed using HTRF assay (data not shown). These pools were then used to set up 14-day fed-batch production cultures in the presence or absence of fucose. The expressed antibody-A molecules from each culture were then purified from culture media using protein-A columns and their various glycan species were analyzed by capillary electrophoresis post PNGase F treatment (FIG. 6B). A major peak representing G0-F glycan species (afucosylated) was present in all FXKO hosts in the absence of fucose, while in the presence of fucose G0 species formed the major peak in the electropherogram charts (FIG. 6B). Analysis of more than 98% of all antibody glycan species of each FXKO host showed that they all express only afucosylated antibodies in the absence of fucose while when fucose is present, less than 2% of antibodies are afucosylated (FIG. 6C). Therefore, while deficient for fucosylation in the absence of fucose, process of antibody fucosylation was fully restored in all of the FXKO clones when fucose was present (FIG. 6C). Since FX gene is fully deleted in all alleles of FXKO3-11 host (FIG. 4A), we chose this host for further studies.

FXKO Host Assessment in CLD Process

Figure 7A:
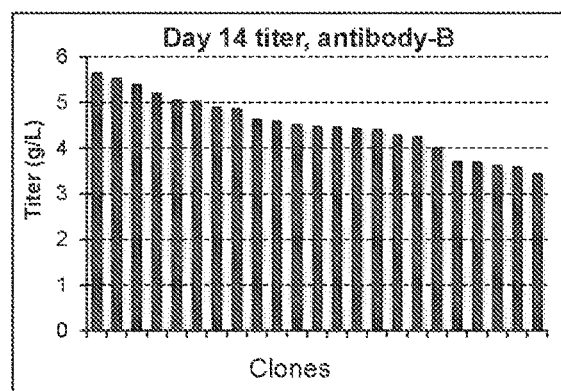
FIGS. 7A-7F show analyses of an antibody produced by 24 clones of the FXKO3-11 host following a standard CLD process.
Figure 7B:
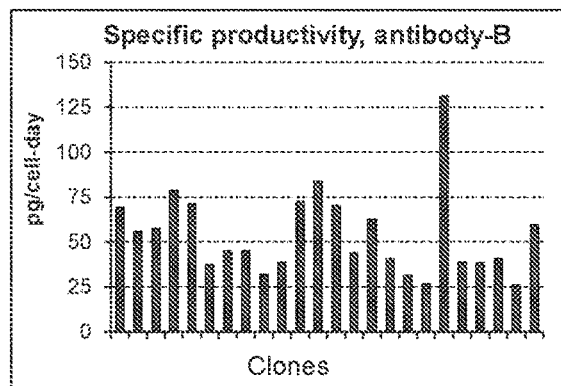
Figures 7C, 7D:
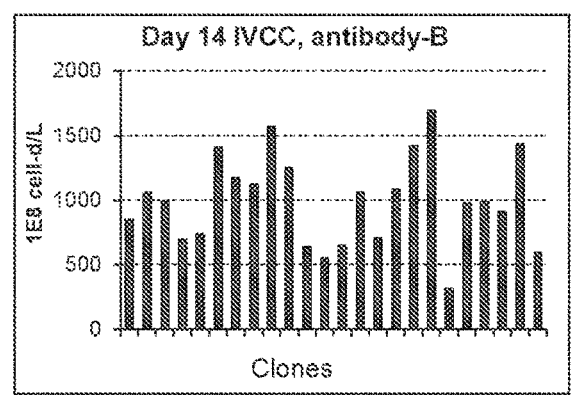
Figure 7E:
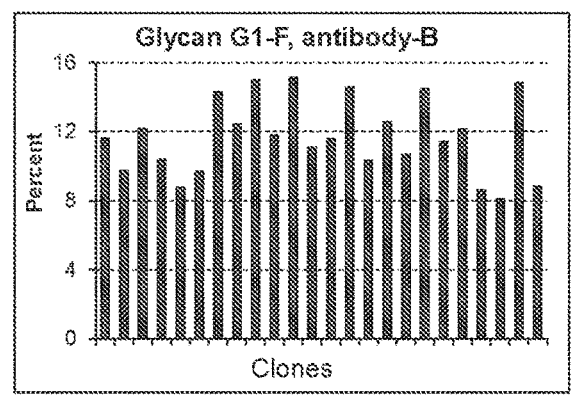
Figure 7F:
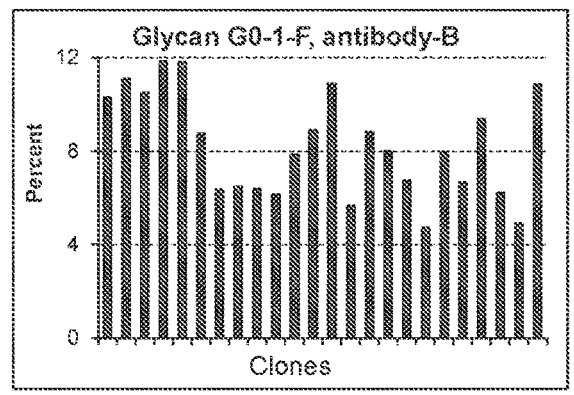

To evaluate performance of FXKO3-11 host during CLD, this host was transfected with a vector expressing antibody-B and glutamine synthase (GS) as selection marker and performed a full CLD. The top 24 clones were evaluated in a production assay and showed to have titers of 3.5-5.5 g/L (FIG. 7A). Unlike the previously reported GMD knockout lines which had highest Qp of 16 pg/cell-day (Kanda et al., *J Biotechnol*, 130, 2007, 300-310), FXKO3-11 clones had Qp ranging from 25-130 pg/cell-day, with majority of the clones having Qp of 40-70 pg/cell-day (FIG. 7B). Antibody-B expressing FXKO3-11 clones displayed a wide range of growth (4-18 million cells/ml) and day 14 viability (40-95%), and as expected, clones with higher Qp grew slower compared to the ones with lower Qp (FIG. 7C) (additional data not shown). Additionally, all FXKO3-11 clones expressed completely afucosylated antibody-B molecules, with majority of the glycoforms as G0-F (FIG. 7D), G1-F (FIG. 7E), and G0-1-F (FIG. 7F), in order of abundance, respectively. Expression of antibody-B was also evaluated independently in a FUT8-KO DP12 host, following an identical CLD protocol, with top clones expressing afucosylated antibody-B at 30-40% lower titers compared to that of top FXKO3-11 clones (data not shown). These findings indicate that FXKO hosts can express a given antibody molecule at comparable or higher titers relative to that of the FUT8-KO host and with potential of expressing both wild type or afucosylated versions of the antibody.

Figure 8A:
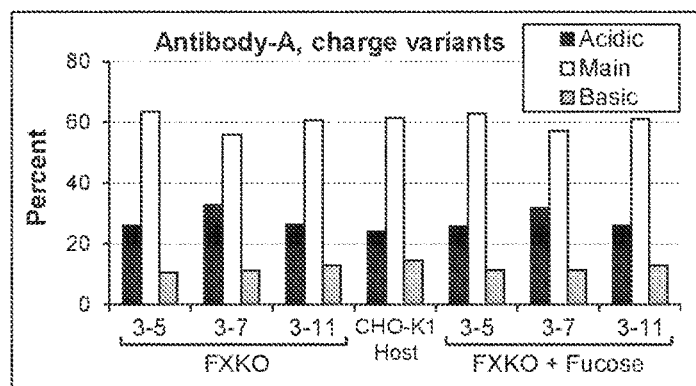
FIGS. 8A-8F show analyses of wild type and afucosylated forms of antibody-A and antibody-B produced by FXKO clones cultured in either the absence of fucose of the presence of 1 mM fucose.
Figure 8B:
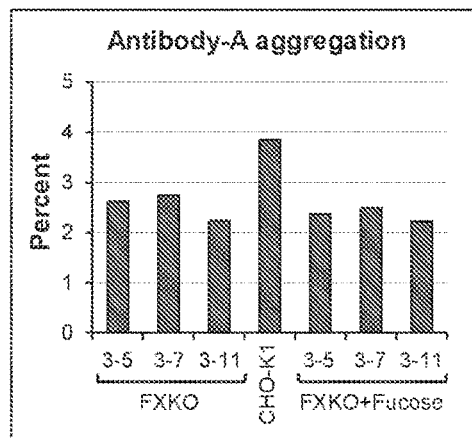
Figure 8C:
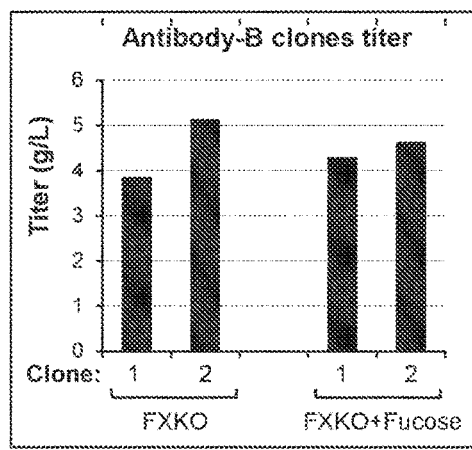
Figure 8D:
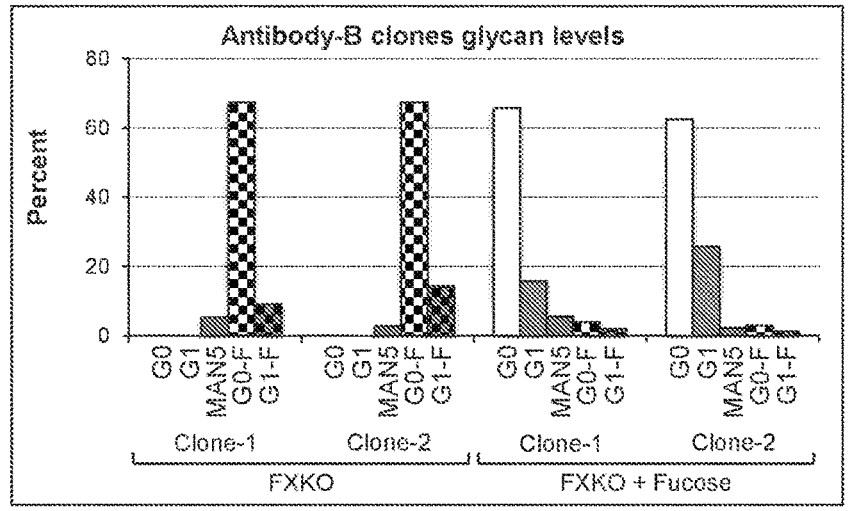

FXKO Host Expresses Both WT or Afucosylated Versions of an Antibody with Similar Product Qualities To assess whether antibody-expressing FXKO clones can express both wild type and afucosylated versions of the same antibody with comparable product qualities, FXKO clones expressing antibody-A (FIGS. 6A-6C) were used in a production assay with or without 1 mM fucose in the media. Percent charge variants and aggregation levels of antibody-A were similar for each clone in the presence or absence of fucose in the media (FIGS. 8A-8B). A similar production assay was performed for two FXKO clones expressing antibody-B (FIGS. 7A-7F) in the presence or absence of 1 mM fucose and both clones had comparable titers regardless of fucose levels (FIG. 8C). In the absence of fucose, all the glycan species of antibody-B were afucosylated however by addition of fucose to the production media both clones expressed antibody-B with the normal and expected distribution of WT glycan species (FIG. 8D).

Figure 8E:
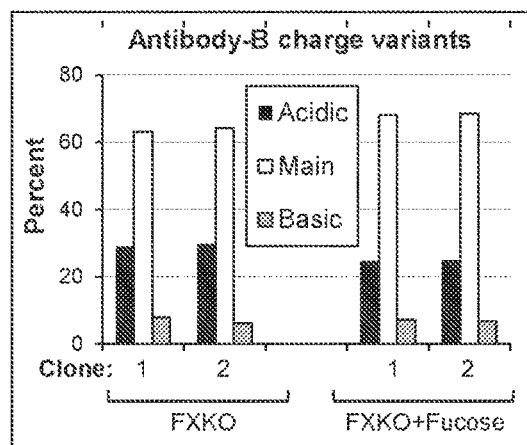
Figure 8F:
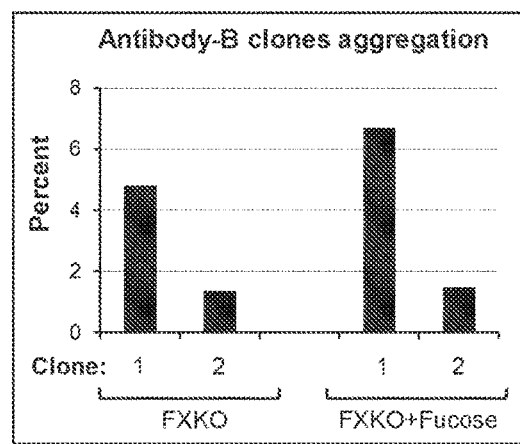
Figure 9A:
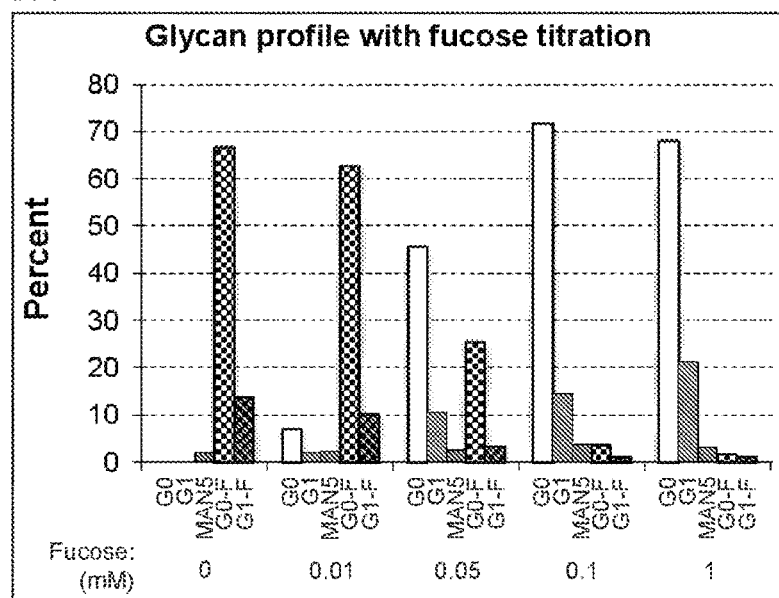
FIGS. 9A-9E show analyses of antibody-B produced by FXKO clones cultured in a range of fucose concentrations.
Figure 9B:
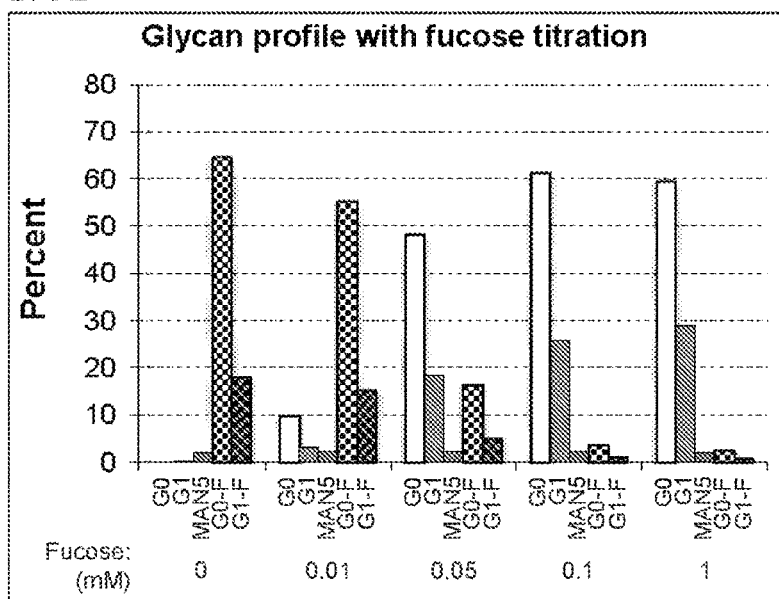
Figure 9C:
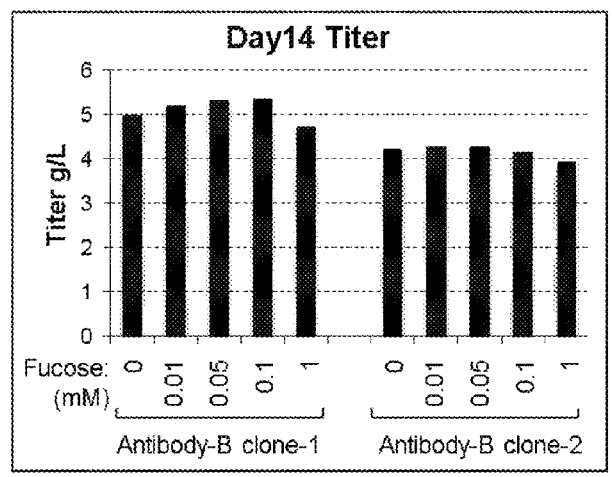
Figure 9D:
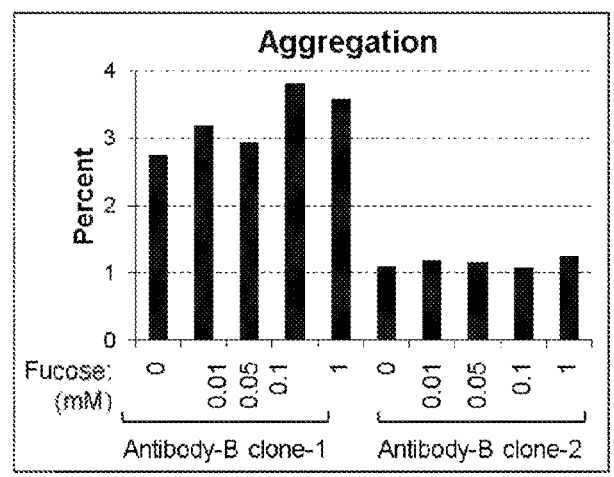
Figure 9E:
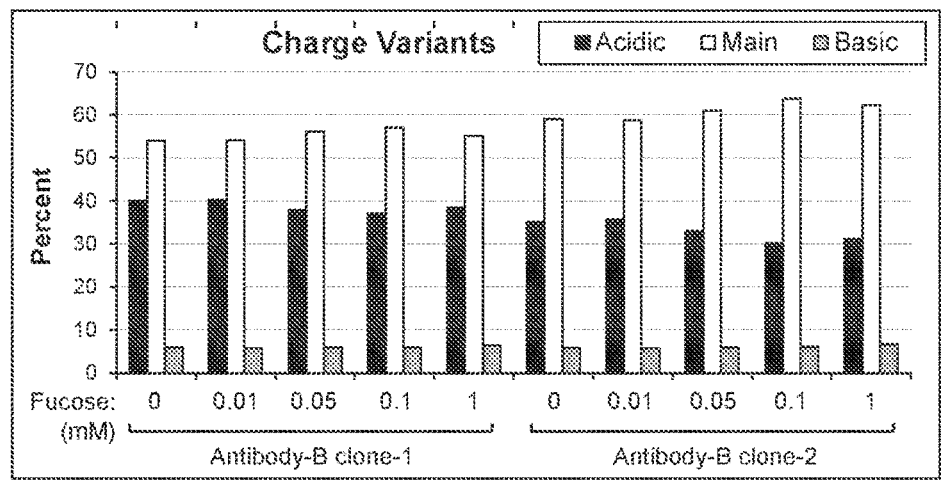

While the percent charge variant species were comparable between the two clones in the presence or absence of fucose (FIG. 8E), we noticed that the percent main peak is somewhat higher (4%) and percent acidic peak is somewhat lower (4%) when fucose is added to the production media (FIG. 8E). Note that it was not observed that such a behavior for the antibody-A production pools (FIG. 8A). Percent aggregate levels remained comparable for antibody-B expressing clones in the presence or absence of fucose (FIG. 8F).

Since FXKO host offers the option of expressing both wild type and afucosylated antibodies with nearly identical product qualities, it is suitable for evaluating the role of afucosylation in enhancing ADCC of an antibody in vitro and in vivo. Such trait ensures that the outcome of the effector function or toxicity studies could be directly linked to the levels of wild type and afucosylated antibody species, and not the product quality differences that are inadvertently present when different clones express these antibodies.

FXKO Host May be Used to Express an Antibody with the Desired Ratios of WT to Afucosylated Glycoforms In cases where having completely afucosylated antibody species is unnecessary or undesirable due to toxicity, it may be beneficial to determine the levels of afucosylated antibodies needed to exert the full effect of ADCC, while minimizing toxicity. To assess whether FXKO clones are capable of expressing antibodies with a desired level(s) of afucosylated glycoforms, two antibody-B expressing clones were selected to establish production cultures with increasing levels of fucose in the media (0-1 mM). This experiment was performed a couple of times in order to fine tune the levels of fucose feed that corresponds to a certain percentage of the afucosylated antibody species in culture. FIGS. 6A-6B show that addition of certain concentrations of fucose to the production media and feed may be used to achieve a desired ratio of wild type to afucosylated antibody levels. The bolus feeding approach was used for these experiments. However, it is envisioned that a continuous equilibrium approach can also be used to produce desired wild type to afucosylated antibody ratios.

Since the levels of various glycan species is determined by PNGase F treatment followed by capillary electrophoresis, it is not possible to determine the fraction of antibody molecules with zero, one, or two afucosylated glycans by this method. Regardless, antibody titers (FIG. 6C), aggregation levels (FIG. 6D), and charge variants percentages (FIG. 6E) were comparable irrespective of the fucose concentration in the production media. Overall, these findings show that a FXKO host allowed for expression of antibodies with desired ratios of wild type to afucosylated glycoforms, suitable for gauging the desired ADCC levels while avoiding toxicity. Furthermore, desired ratios of wild type to afucosylated antibodies with comparable product qualities may be achieved by titrating fucose into the production media and feed, in order to assess the levels of afucosylation needed to maximize ADCC while minimizing toxicity.

Methods:

Vector Constructs and Reagents

Constitutive antibody expression was achieved by cloning the heavy and light chain genes under the control of the cytomegalovirus (CMV) promoter in an antibody expression vector that also directs expression of Glutamine Synthase (GS) for selection. The assembly of the final expression vector and selection using this vector has been previously described. See, Hu et al., *Biotechnol Progr*, 29, 2013, 980-985. Mouse anti β-actin (Sigma, Cat. No. A2228, at 1:30000), and rabbit polyclonal antibody against FX (GeneTex, Cat. No. 101663, at 1:2000) were used for immunoblotting. Protease inhibitor cocktail (Roche, Cat. No. 11-836-153-001) was used in lysis buffers. Lens Culinaris Agglutinin (LCA) (Cat. No. L-1040) and FITC conjugated LCA (LCA-FITC) (Cat. No. FL-1041) reagents were purchased from Vector Laboratories. Fucose was purchased from Sigma (Cat. No. F2252). The following primers were used for amplifying the WT or FXKO gene segments:

Forward WT FX primer: GTCACCCAAAGCTCTCCTTG; (SEQ ID NO. 1)

reverse WT FX primer: AAAAGTCCTGCTCTGCTTGC; (SEQ ID NO. 2)

forward FXKO primer: CTAGGCTTCCCTAGGCCATT; (SEQ ID NO. 3)
and reverse FXKO primer: GCTATGCCCTTGAGTCTTGG. (SEQ ID NO. 4)

Immunoblotting

For immunoblot analysis, cells were lysed at 30-50 million cells/ml in NP40 lysis buffer (10 mM Tris, pH8.0, 0.5% NP40, 150 mM NaCl, and 5 mM $MgCl_2$ with protease inhibitor cocktail) for 20 minutes on ice. The lysates were then centrifuged for 10 minutes at 13,000 rpm at 4° C. and supernatant was transferred to a new tube and the protein concentration was determined by BCA assay (Thermo Scientific). 150 µl of each lysate was mixed with 50 µl of 4× reducing loading buffer and boiled for 5 minutes. Equal protein concentrations for each sample were loaded on SDS-PAGE gel (4-20% Tris-Glycine) and transferred to membrane for immunoblotting.

FACS Analysis of LCA-FITC Stained Cells 200,000 cells were spun down and washed once with 0.5 ml PBS and resuspended in 0.3 ml of PBS with 1% BSA. Cells were stained with LCA-FITC at a final concentration of 2 µg/ml for 30 minutes on ice. Cells were then transferred to FACS tubes and analyzed using a FACSCalibur analytic flow cytometer (Becton Dickinson). FlowJo software was used to analyze all the samples.

Cell Culture and Stable Transfection

CHO-K1 host cells were cultured in serum free proprietary Genentech media at 37° C. and 5% $CO_2$. Amaxa nucleofector kit-V (Lonza, Cat. No. VCA-1003) was used to stably transfect CHO-K1 cells following standard transfection protocols. Transfected cells were plated in 384-well plates and selected with Methionine Sulfoximine (MSX). 3-4 weeks later, 1000 growing colonies were picked into 96-well plates in the presence of MSX. After 4-5 days, picked colonies were assayed for antibody expression using Homogenous Time-Resolved FRET (HTRF) assay. Top clones were single cell cloned using limiting dilution into 384-well plates, followed by imaging. 3-4 weeks later about 700 growing clones were picked into 96-well plates and subjected to a HTRF assay (days 4-6). The top 200 and subsequently the top 100 antibody-expressing clones were assayed via HTRF. Top 48 single cell cloned and imaged confirmed clones were adapted to suspension growth and evaluated in production assays as previously described (Misaghi et al., Biotechnol Progr, 30, 2014, 1432-1440). Briefly, cells were seeded at 1×10⁶ cells/ml in a production medium, with the indicated amounts of fucose. Cultures received proprietary feed medium and fucose (at indicated concentrations) on days 3, 7, and 10. Viable cell count (VCC) and % viability of cells in culture was measured on days 0, 3, 7, 10, and 14 using a Vi-Cell XR instrument (Beckman Coulter). Antibody titers were determined on days 7, 10, and 14 of production culture (protein-A purification). Glucose and lactate were measured on days 7, and 14 using a Bioprofile 400 Analyzer (Nova Biomedical). Charge variants were measured via capillary Iso-Electric Focusing (cIEF) and glycan sub-types were identified by PNGaseF digestion followed by capillary electrophoresis. Levels of aggregates were determined by subjecting the protein-A purified antibody to gel filtration (sizing) column.

Example 2

Modulation of Antibody Fucosylation in the FXKO Host can Regulate FcγRIII Binding and ADCC Levels Methods:

ADCC Assay

An engineered NK cell line (Roche) was used to provide effector cells and DELFIA BATDA (Perkin Elmer) labeled WIL2-S cells were used as target cells. A mixture of labeled WIL2-S target cells (2×10⁴) and NK cells (1.0×10⁵) was prepared in assay medium (RPMI 1640 with 10% heat inactivated-FBS, 2 mM L-glutamine, and 20 mM HEPES, pH 7.2) and was added to each well of a round-bottom, 96-well tissue culture plate. Targeted dilutions of antibodies (100 to 0.06 ng/mL) were added to the plates and the plates were incubated for 3 hours. Cell lysis was measured using time-resolved fluorescence in relative fluorescence units (RFU) by excitation at 345 nm and quantification of emission at 615 nm using a microplate reader SPECTRAMAX® 190 (Molecular Devices). Absorbance of wells containing only labeled target cells served as the control for background (Background), whereas wells containing labeled target cells with DELFIA BATDA lysis buffer provided the maximum available signal (Maximum Release). Spontaneous release (SR) was measured from wells containing only target cells, whereas SR+NK was measured from wells containing both target and effector cells without antibody. The percent specific toxicity (% ST) was determined according to the following formula:

% $ST$={[(Specific Release−Background)−(Spontaneous Release−Background)]×100}/[(Maximum Release−Background)−(Spontaneous Release−Background)].

The dose response curves were generated by plotting the mean % ST from triplicates against the concentration of antibody sample in ng/mL using a 4-parameter fit. Data analysis was performed using parallel line analysis curve fitting software (PLA) from SOFTmaxPRO™. See Shatz et al., mAbs, 5, 2013, 872-81.

FcγRIII Binding Assay

Figures 10A, 10B:
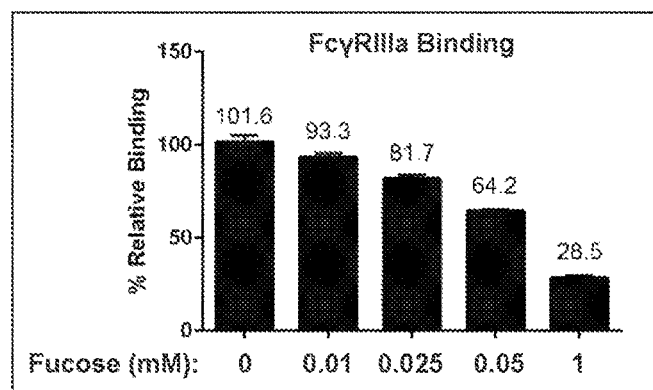
FIGS. 10A-10G show analyses of antibodies produced by FXKO clones cultured in a range of fucose concentrations.
Figures 10C, 10D:
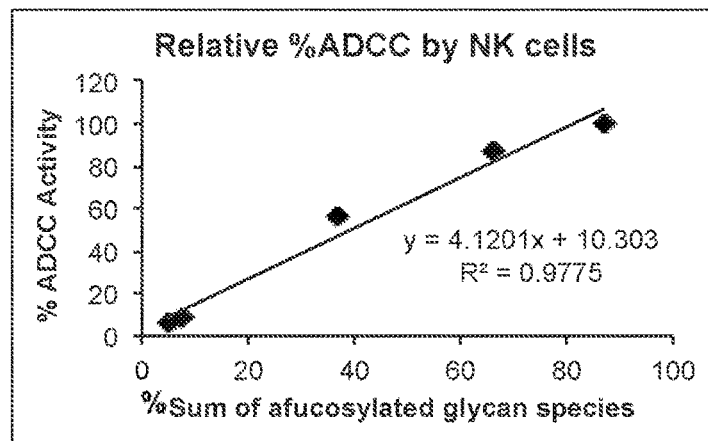

A Biacore T200 instrument (GE healthcare) was used for SPR analysis. Anti-His antibody (R&D Systems) was diluted to 50 µg/mL and immobilized on Biacore Sensor CM5 Chips (GE healthcare) by injecting for 7 minutes at 10 µL/min using amine-coupling kit (GE healthcare). In each cycle, FcγRIIIa-6×His tag protein (Genentech) was captured before sample injection. FcγRIIIa-6×His tag protein was diluted to 0.5 mg/mL in PBS with 0.1% BSA and 0.05% Tween 20 and were captured for 2 minutes at 10 µL/min. Samples prepared at 10 µg/mL antibody concentration in PBS with 0.05% Tween 20 were injected for 5 minutes at 50 µL/min for FcγRIIIa binding. The dissociation phase was achieved by passing the same running buffer through the chamber for 5 minutes. All experiments were performed at 25° C. Triplicate injections of each sample and a buffer blank were flowed over the two surfaces (a reference flow cell and a testing flow cell). Data were collected at a rate of 1 Hz. Readout was the maximum binding response during association phase, five seconds before the end of the sample injection. A reference flow cell was run in conjunction to the testing flow cell to negate the effects of non-specific binding. In addition, injections of blank running buffer were included on experimental flow cells. Signals from the reference flow cell and blank buffer injections were subtracted from the absolute response of sample injections on experimental flow cells (double subtraction method). Data was analyzed using Biacore T200 evaluation software and JMP software.
Results:

To evaluate the function of antibodies with different ratios of afucosylated to fucosylated glycoforms, an antibody-B expressing FXKO clone was used to set up production assays with different levels of fucose feed (FIG. 10A). Increasing concentrations of fucose feed during production resulted in a gradual increase in levels of fucosylated antibody species while levels of afucosylated antibody species decreased accordingly. Antibody-B was then purified from these cultures and subjected to an in vitro FcγRIII binding assay as a surrogate for NK cell binding (FIG. 10B). As illustrated, a decrease in levels of fucosylated antibody species corresponds to a decrease in FcγRIII binding (FIG. 10B). Although at fucose concentrations of 0.025 mM only about 40-50% of glycans are afucosylated, approximately 80% of FcγRIII binding competence remains intact. The FXKO host cells were transfected with a construct that expressed antibody-C(IgG1), for which a functional ADCC assay had been developed. After pool selection, pool production assays were performed with indicated concentrations of fucose feed to obtain antibody-C cultures with varying ratios of afucosylated to fucosylated antibody species (FIG. 10C). Purified antibody-C from these cultures was used in ADCC assays and a linear correlation between % ADCC activity and levels of afucosylated glycan species was observed (FIG. 10D). Mixing of primarily fucosylated (1 mM fucose) and fully afucosylated (0 mM fucose) antibody-C samples could trigger a predictable ADCC response (FIG. 10E) based on levels of afucosylated glycan species and the fucose titration chart (FIG. 10D). This suggests that the fucose-feeding approach is indeed a viable method to generate antibodies with similar product qualities and the desired distribution of fucosylated to afucosylated glycan species for triggering ADCC in a predictable manner. It is noteworthy to mention that fucose-feeding approach eliminates the need for two separate manufacturing campaigns required to generate both fully afucosylated and primarily fucosylated antibodies.

Figures 10E, 10F:
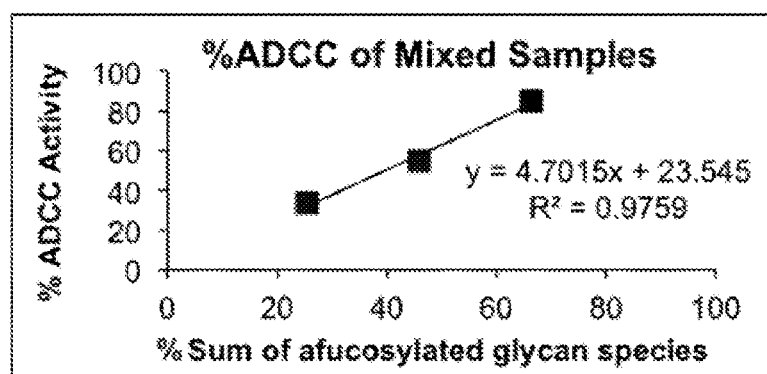
Figure 10G:
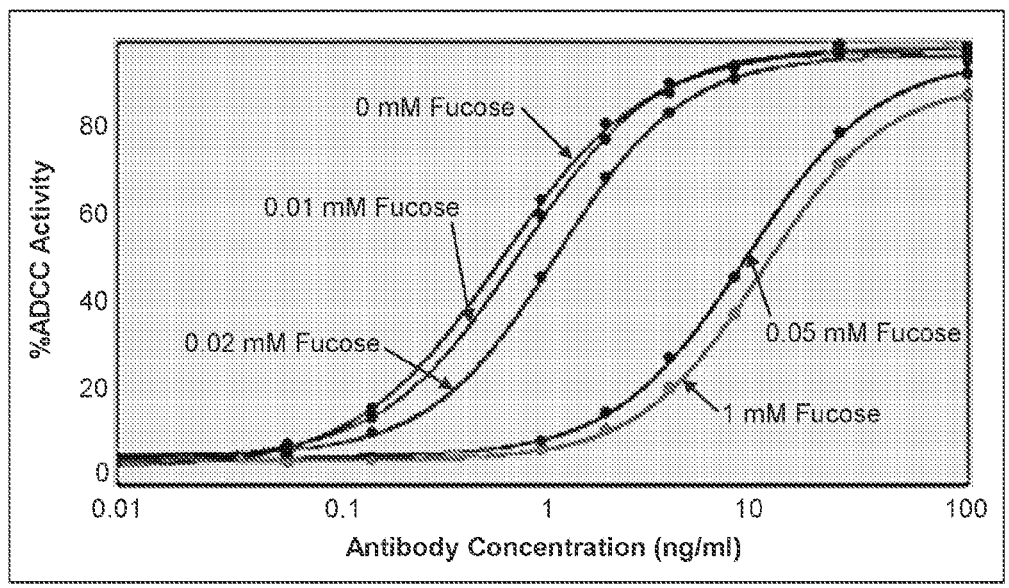

ADCC dose-response analysis showed that fully afucosylated antibody-C molecules could achieve 50% of the maximum ADCC activity at 20 fold lower concentrations compared to their primarily fucosylated counterparts (FIG. 10G). Note that almost 80% of the ADCC activity can be maintained with only 60% of antibody molecules carrying afucosylated glycan species (FIGS. 10D, 10E, and 10F). Additionally, with 0.02 mM fucose feed where less than 40% of glycans are afucosylated, relatively comparable % ADCC activities can be achieved with same antibody-C concentrations as that of fully afucosylated (0 mM fucose) samples (FIG. 10G). Hence, the findings suggest that it is not necessary to have 100% fully afucosylated antibodies in order to achieve nearly maximum levels of ADCC activity.

What is claimed is:

1. A method of producing a Fc-containing protein, wherein the Fc-containing protein is produced in fucosylated and afucosylated forms at a predetermined ratio, the method comprising culturing a host cell engineered to express the Fc-containing protein in a culture medium,
wherein the host cell has no GDP-keto-6-deoxymannose-3,5-epimerase,4-reductase (FX) activity,
wherein the host cell is a FX knockout host cell having FX knocked out in all alleles, and
wherein the culture medium comprises a fucose source in an amount sufficient to produce the fucosylated and afucosylated forms of the Fc-containing protein at the predetermined ratio.

2. The method of claim 1, wherein the predetermined ratio is about 50:1 to about 1:50.

3. A method of producing a Fc-containing protein having an enhanced ADCC function mediated both by NK cells and PMN cells, the method comprising culturing a host cell engineered to express the Fc-containing protein in a culture medium,
wherein the host cell has no FX activity,
wherein the host cell is a FX knockout host cell having FX knocked out in all alleles, and
wherein the culture medium comprises a fucose source in an amount sufficient to produce fucosylated and afucosylated forms of the Fc-containing protein at a ratio that provides the enhanced ADCC function.

4. The method of claim 3, wherein the ADCC function is determined by an ADCC assay or by a FCγRIII binding assay.

5. A method of adjusting a level of fucosylation of a Fc-containing protein produced by a host cell engineered to produce the Fc-containing protein, the method comprising:
(a) culturing the host cell in an initial culture medium,
wherein the host cell has no FX activity,
wherein the host cell is a FX knockout host cell having FX knocked out in all alleles, and
wherein the culture medium comprises a fucose source;
(b) determining the level of fucosylation of the Fc-containing protein; and
(c) adjusting the amount of the fucose source in the culture medium such that the Fc-containing protein is produced at a predetermined level of fucosylation.

6. The method of claim 5, wherein adjusting the amount of the fucose source comprises increasing amount of the fucose source when the level of fucosylation is low.

7. The method of claim 5, wherein adjusting the amount of the fucose source comprises decreasing amount of the fucose source when the level of fucosylation is high.

8. The method of claim 1, wherein the method comprises culturing the host cell in a culture medium free of the fucose source prior to culturing the host cell in the culture medium comprising the fucose source.

9. The method of claim 1, wherein the fucose source is present in the culture medium at the beginning of the culturing step.

10. The method of claim 1, wherein the amount of the fucose source in the culture medium during the culturing step is between about 0.01 mM and about 1 mM.

11. The method of claim 1, wherein the culturing step is carried out at lower than about 37° C.

12. The method of claim 1, wherein the fucose source is selected from the group consisting of L-fucose, L-fucose-1-phosphate, and GDP-fucose.

13. The method of claim 1, wherein the fucose source is GDP-fucose.

14. A method of characterizing a Fc-containing protein in an afucosylated form, the method comprising comparing the biological activity of the afucosylated Fc-containing protein with a fucosyalted form of the Fc-containing protein,
wherein the afucosylated and fucosylated forms of the Fc-containing protein are produced by the same host cell engineered to produce the Fc-containing protein,
wherein the host cell has no FX activity, and
wherein the host cell is a FX knockout host cell having FX knocked out in all alleles.

15. The method of claim 1, wherein the fucosylated form of the Fc-containing protein is determined at a glycan structure level or at a protein level.

16. The method of claim 1, wherein the Fc-containing protein is a full length antibody.

17. The method of claim 1, wherein the host cell is a mammalian cell.

18. The method of claim 17, wherein the mammalian cell is a Chinese hamster ovary (CHO) cell.

19. The method of claim 1, wherein the FX gene in the host cell is inactivated by a sequence deletion or by a sequence addition or substitution.

20. The method of claim 19, wherein the FX gene is inactivated using:
(a) a clustered, regularly interspaced, short palindromic repeats (CRISPR) system;
(b) a transcription activator-like effector nuclease (TALEN) system;
(c) a zinc-finger nuclease (ZFN) system; or
(d) a meganuclease system.

21. A cell culture comprising:
(a) a host cell engineered to express a Fc-containing protein,
wherein the host cell has no FX activity,
wherein the host cell is a FX knockout host cell having FX knocked out in all alleles,
wherein the host cell is capable of producing the Fc-containing protein in fucosylated and afucosylated forms of the Fc-containing protein, and
wherein the host cell comprises a nucleic acid encoding the Fc-containing protein; and
(b) a culture medium comprising a fucose source at about 0.01 mM to about 1 mM.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
gtcacccaaa gctctccttg     20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
aaaagtcctg ctctgcttgc     20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
ctaggcttcc ctaggccatt     20

<210> SEQ ID NO 4
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 4
gctatgccct tgagtcttgg                                               20
```